(12) United States Patent
Imai et al.

(10) Patent No.: US 6,793,917 B1
(45) Date of Patent: Sep. 21, 2004

(54) TYPE CC CHEMOKINE-LIKE PROTEIN

(75) Inventors: Toshio Imai, Kyoto (JP); Tetsuya Yoshida, Osaka (JP); Osamu Yoshie, Nishinomiya (JP)

(73) Assignee: Shionogi & Co., Ltd., Osaka (JP)

( * ) Notice: Subject to any disclaimer, the term of this patent is extended or adjusted under 35 U.S.C. 154(b) by 1826 days.

(21) Appl. No.: 09/043,861

(22) PCT Filed: Sep. 27, 1996

(86) PCT No.: PCT/JP96/02801

§ 371 (c)(1),
(2), (4) Date: Mar. 27, 1998

(87) PCT Pub. No.: WO97/11969

PCT Pub. Date: Mar. 4, 1997

(30) Foreign Application Priority Data

Sep. 27, 1995 (JP) ................................. 7-249457
Mar. 13, 1996 (JP) ............................... 8-056044

(51) Int. Cl.[7] .......................... C12N 5/16; C12N 15/19; C12N 15/63; C07K 14/52; A61K 38/19
(52) U.S. Cl. ..................... 424/85.1; 435/69.5; 435/71.1; 435/243; 435/320.1; 435/325; 435/348; 530/351; 536/23.1

(58) Field of Search ..................... 530/351; 424/85.1; 435/69.5, 252.3, 320.1, 71.1, 243, 325, 348; 536/23.5

(56) References Cited

FOREIGN PATENT DOCUMENTS

| WO | 9729192 | * | 8/1997 |
| WO | 9807862 | * | 2/1998 |

OTHER PUBLICATIONS

Marra et al, EST Accession No. AA863527 Clark–Lewis J. Leukazte 57, 1995, p. 705.*
von Arker et al, Medrathor of Inglam vol. 5, 1996, p. 393.*
Howard et al, TIBE CH 2/91 vol. 14, p.46.*

* cited by examiner

Primary Examiner—Christine J. Saoud
(74) Attorney, Agent, or Firm—Foley & Lardner LLP

(57) ABSTRACT

An isolated novel type CC chemokine-like protein which is expressed from peripheral blood mononuclear cells under an immunological stimulus and has a cell migration activity; a DNA encoding the protein; an expression vector and a transformant containing the DNA; a process for producing a recombinant protein by using the transformant; and a pharmaceutical composition containing the protein.

9 Claims, 29 Drawing Sheets

```
  1                                              CCCTGAGCAGAGGGACCTGCACACAGAGACTCCCTGGGCTCCTGGCACC        52

53   ATG GCC CCA CTG AAG ATG CTG GCC CTG GTC ACC CTC CTG GGG                                            97
  1    M   A   P   L   K   M   L   A   L   V   T   L   L   G                                            15

98   GCT TCT CTG CAG CAC ATC CAC GCA|GCT CGA GGG ACC AAT GTG GGC                                       142
 16    A   S   L   Q   H   I   H   A  | A   R   G   T   N   V   G                                       30

143   CGG GAG TGC TGC CTG GAG TAC TTC AAG GGA GCC ATT CCC CTT AGA                                       187
 31    R   E   C   C   L   E   Y   F   K   G   A   I   P   L   R                                        45

188   AAG CTG AAG ACG TGG TAC CAG ACA TCT GAG GAC TGC TCC AGG GAT                                       232
 46    K   L   K   T   W   Y   Q   T   S   E   D   C   S   R   D                                        60

233   GCC ATC GTT TTT GTA ACT GTG CAG GGC AGG AGG GCC ATC TGT TCG GAC                                   277
 61    A   I   V   F   V   T   V   Q   G   R   R   A   I   C   S   D                                    75

278   CCC AAC AAC AAG AGA GTG AAG AAT GCA GTT AAA TAC CTG CAA AGC                                       322
 76    P   N   N   K   R   V   K   N   A   V   K   Y   L   Q   S                                        90

323   CTT GAG AGG TCT TGA AGCCTCCTCACCCCAGACTCCTGACTGTCTCCCGGGACT                                       376
 91    L   E   R   S   *                                                                                94

377   ACCTGGGACCTCCACCGTTGGTGTTCACCGCCCCCACCCTGAGCGCCTGGGTCCAGGGG                                       435

436   AGGCCTTCCAGGGACGAAGAAGAGCCACAGTGAGGGAGATCCCATCCCCCTTGTCTGAAC                                      494

495   TGGAGCCATGGGCACAAAGGGCCCAGATTAAAGTCTTTATCCTC                                                      538
```

```
TARC    AR-GTNVGRECCLEYFKGAIPLRKLKTWYQ-   TSEDCSR   100%
RANTES  SPYSSDT-TPCCFAYIARPLPRAHIKEYF-    YTSGKCSN   29%
MIP-1A  ASLAADTPTACCFSYTSRQIPQNFIADYF-    ETSSQCSK   26%
MIP-1b  APMGSDPPTACCFSYTARKLPRNFVVDYY-    ETSSLCSQ   28%
I-309   KSMQVPFSR-CCFSFAEQEIPLRAILCY-RN   TSS-ICSN   24%
MCP-1   QPDAINAPVTCCYNFTNRKISVQRLASYRRI   TSSKCPK    24%
MCP-2   QPDSVSIPITCCFNVINRKIPIQRLESYTRI   TNIQCPK    24%
MCP-3   QPVGINTSTTCCYRFINKKIPKQRLESYRRT   TSSHCPR    28%

TARC    DAIVFVTVQGRAICSDPNNKRVKNAVKYLQSLERS
RANTES  PAVVFVTRKNRQVCANPEKKWVREYINSLEMS
MIP-1A  PGVIFLTKRSRQVCADPSEEWVQKYVSDLELSA
MIP-1b  PAVVFQTKRSKQVCADPSESWVQEYVYDLELN
I-309   EGLIFKLKRGKEACALDTVGWVQRHRKMLRHCPSKRK
MCP-1   EAVIFKTIVAKEICADPKQKWVQDSMDHLDKQTPKT
MCP-2   EAVIFKTKRGKEVCADPKERWVRDSMKHLDQIFQNLKP
MCP-3   EAVIEKTKLDKEICADPTQKWVQDFMKHLDKKTQTPKL
```

C

Deduced sequence : MAPLKMLALVTLLLGASLQHIHAARGTNVGRECC...
Determined sequence : ARGTNVGRE**

2   ATG AGG TCA CTT CAG ATG CTG CTC CTG GCT GCT CTG CTT CTG GGG              46
1    M   R   S   L   Q   M   L   L   L   A   A   L   L   L   G              15

47  ACT TTT CTG CAG CAT GCC AGA GCT|GCT CGA GCC ACC AAT GTA GGC              91
15   T   F   L   Q   H   A   R   A   A   R   A   T   N   V   G              30

92  CGA GAG TGC TGC CTG GAT TAC TTC AAA GGG GCC ATT CCT ATC AGG             136
30   R   E   C   C   L   D   Y   F   K   G   A   I   P   I   R              45

137 AAG TTG GTG AGC TGG TAT AAG ACC TCA GTG GAG TGT TCC AGG GAT             181
45   K   L   V   S   W   Y   K   T   S   V   E   C   S   R   D              60

182 GCC ATC GTG TTT CTG ACT GTC CAG GGC AAG CTC ATC TGT GCA GAC             226
60   A   I   V   F   L   T   V   Q   G   K   L   I   C   A   D              75

227 CCC AAA GAC AAA CAT GTG AAG AAG GCC ATC AGA TTG GTG AAA AAC             271
75   P   K   D   K   H   V   K   K   A   I   R   L   V   K   N              90

272 CCA AGG CCG TGA CCTTCCCGCTGAGGCATTTGGAGACGCCAGGGCTGCTGTCCAT             326
91   P   R   P   *                                                          93

327 GGTTTCAACATAAAGCGGCCTGTGACCAGCAGAGCCCAAGAGCAGCCACAGAGCAGAAG             385

386 TCCCTGTTCCCTTTTTTATGACTCTTATGCACTACAGGCGAACACAAAAAAGCAAC                444

445 GGAATAAAGCCTTCCTCCCTC                                                   465
```

Fig. 11

Fig. 12
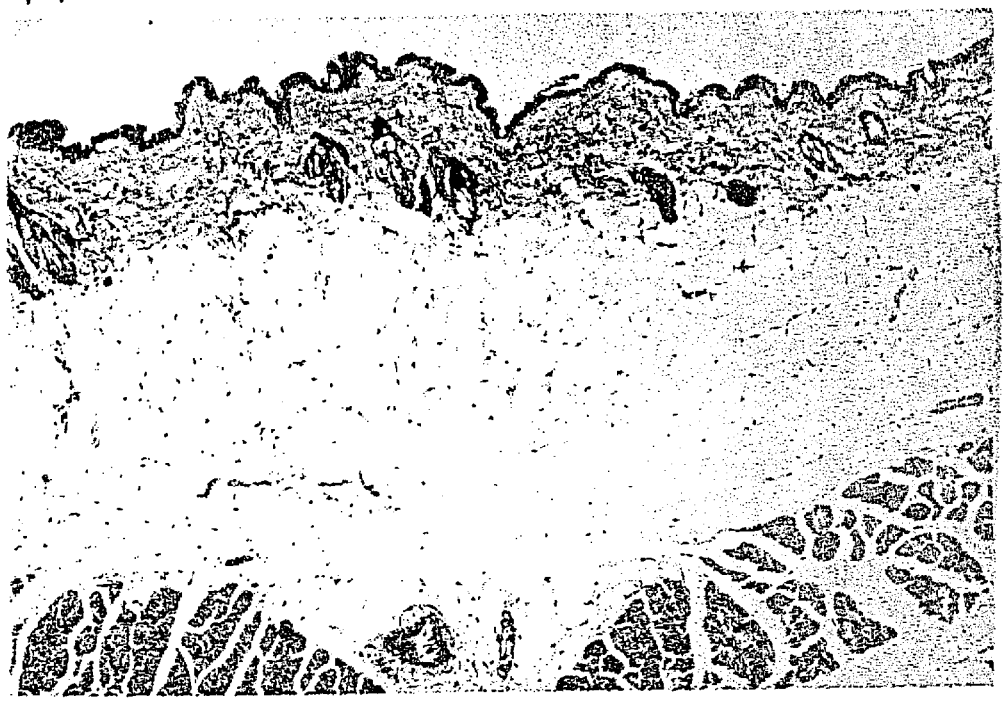
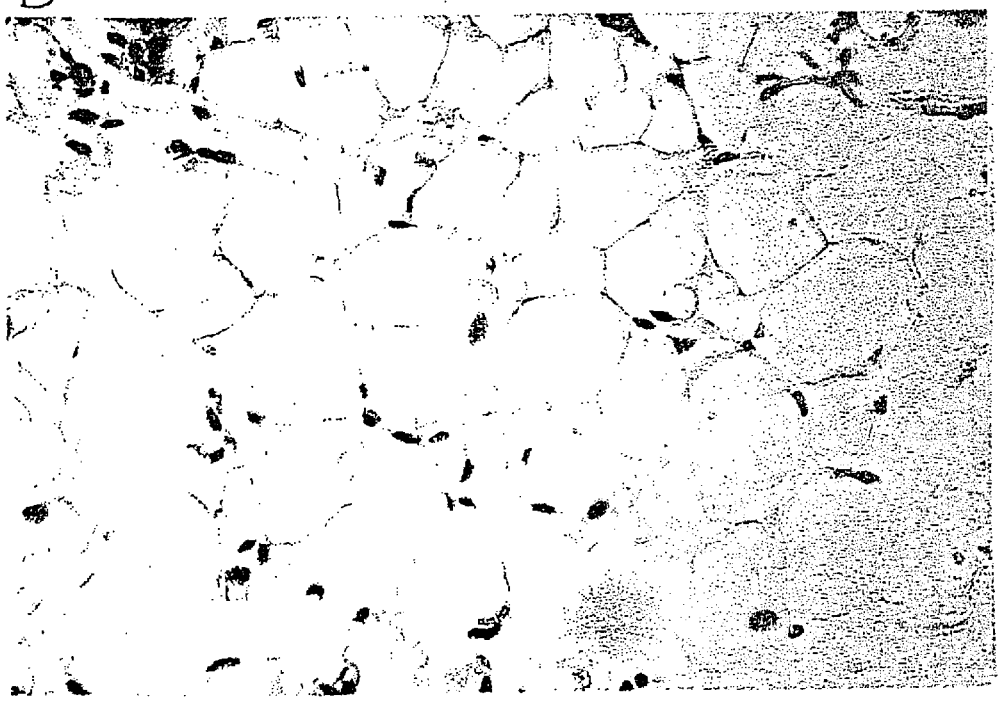

Fig. 14
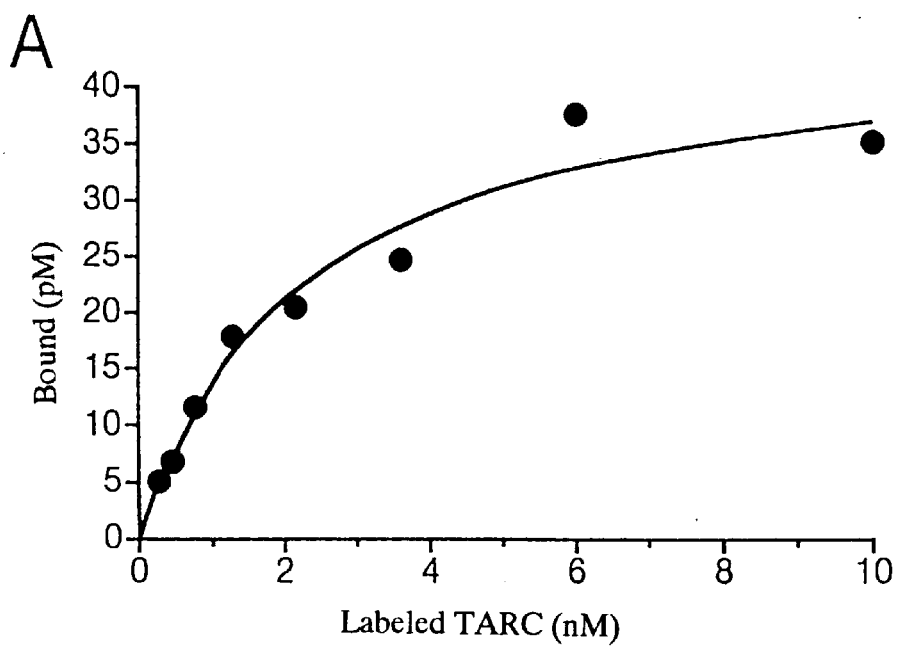
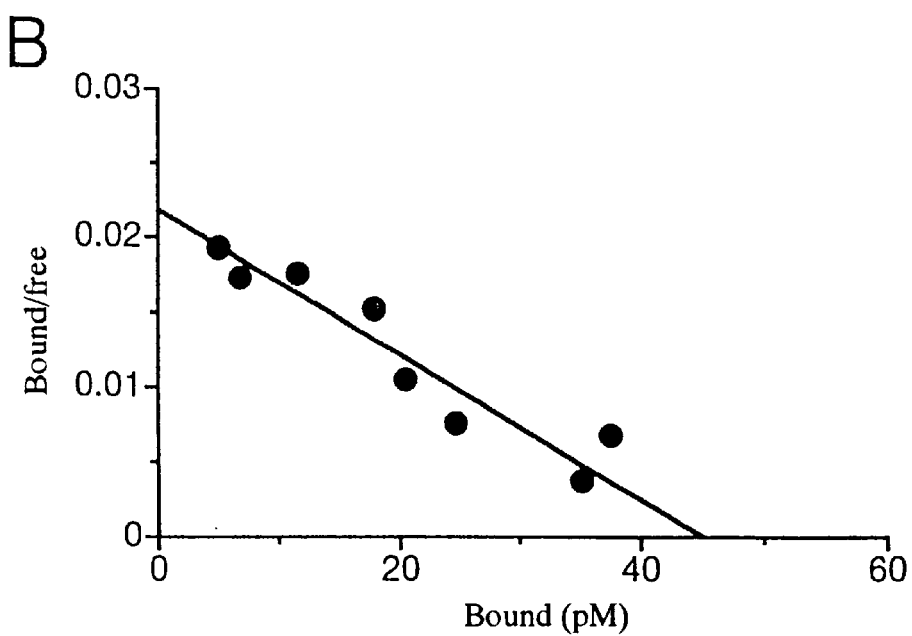

Fig. 23
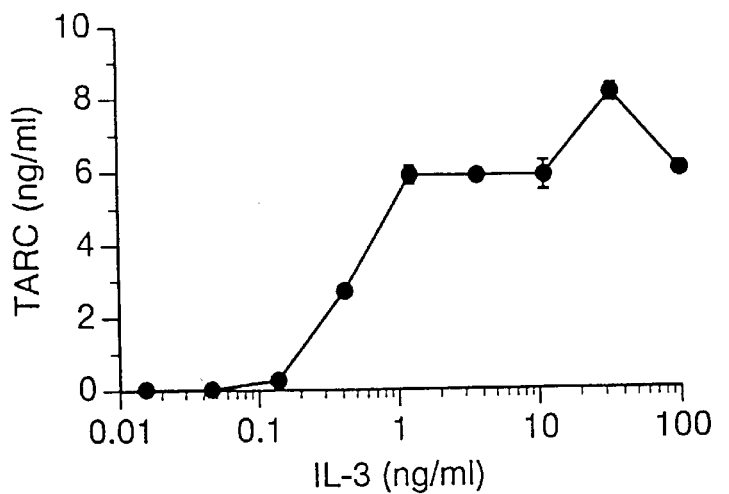
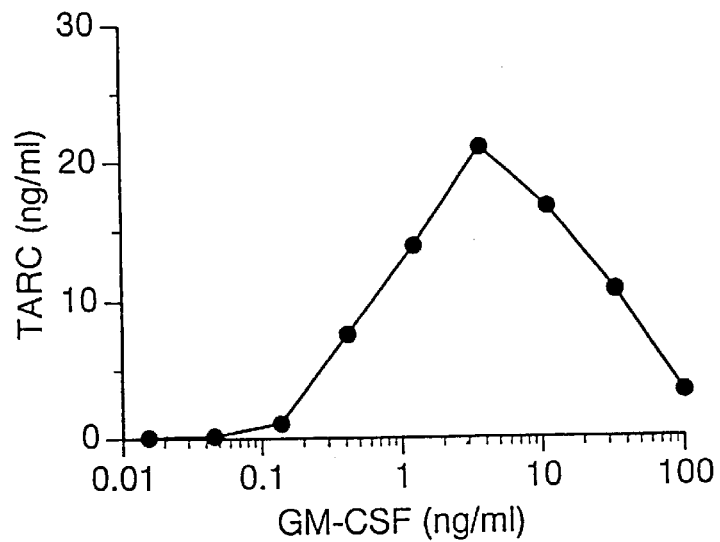
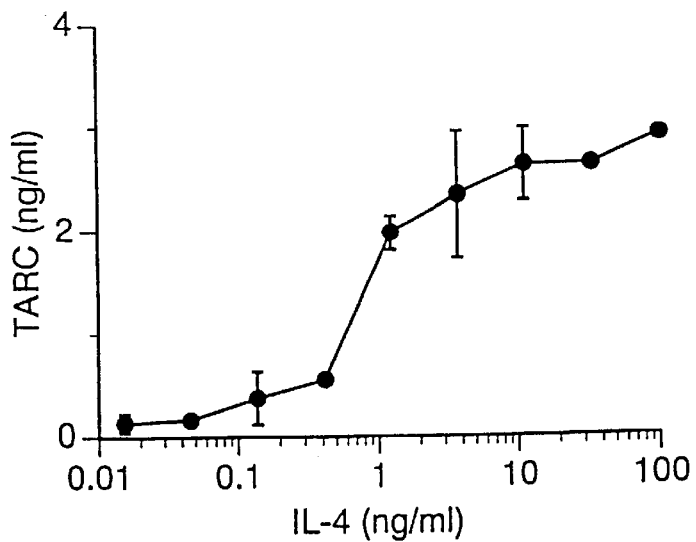

Fig. 26
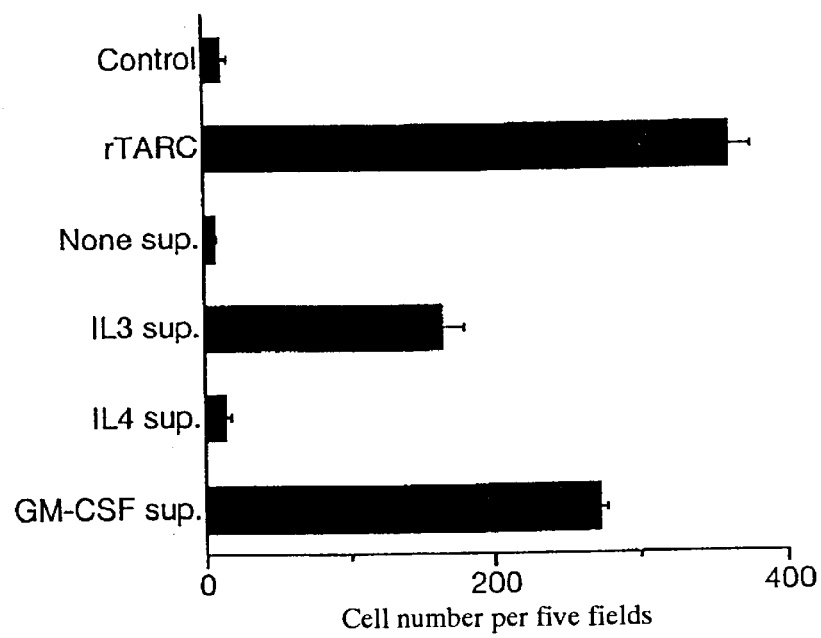
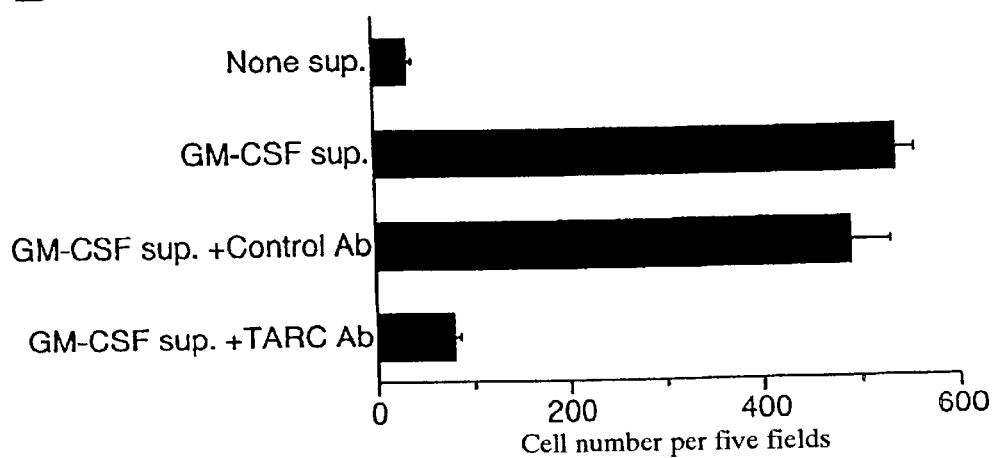

TYPE CC CHEMOKINE-LIKE PROTEIN

TECHNICAL FIELD

The present invention relates to a novel chemokine-like protein of type CC, a DNA encoding said protein, a vector comprising said DNA, and a transformant containing said vector. In addition, the present invention relates to a use of the above novel protein, as well as a pharmaceutical composition comprising the protein, for example, an anti-inflammatory agent, an immune response modifier, or a diagnostic for diseases associated with inflammation and/or immunity. The present invention also relates to a monoclonal antibody raised against said protein and a hybridoma capable of producing said antibody.

BACKGROUND ART

Various exogenous or endogenous tissue impairments, invasions, or exposures to antigens, which are caused by physical, chemical or biological mechanisms, induce strong inflammatory or immune responses. Although these responses are essential biophylactic reactions, they may sometimes bring about acute or chronic diseases. When a substance causative of inflammatory or immune responses attacks a tissue, inflammatory or immune competent cells such as neutrophils, granulocytes, or macrophages, first adsorb to vascular endothelium, and then migrate outside the blood vessel and accumulate at an invaded or impaired tissue, or a tissue where an antigen exists. As substances inducing such sequential cell migration reactions, there exist a group of chemotactic cytokines, so-called "chemokines". Chemokines belong to a cytokine family which induces the migration reactions (chemotactic reactions), and at least 18 kinds of chemokines have been reported in human. Chemokines are known to be closely related to each other in the structure because they have similar amino acid sequences.

Chemokines are generally classified into two groups based on the arrangement of the first two cysteine residues of the four cysteines commonly conserved, that is, type α or CXC in which the two cysteines are intervened by one amino acid, and type β or CC in which the two cysteines are contiguous. Examples of the type CXC chemokines in human include IL-8, β-TG, PF-4, MGSA/GRO, ENA-78, NAP-2, GCP-2 and IP-10, which mainly induce the activation and migration of neutrophils. Examples of the type CC chemokines in human include MIP-1α, MIP-1β, RANTES, MCP-1, MCP-2, MCP-3, and I-309, which mainly induce the activation and migration of monocyte/macrophages. Furthermore, the type CC chemokines also include those capable of inducing the activation and migration of T-cells, basophils, eosinophils, or the like (J. J. Oppenheim et al., Annu. Rev. Immunol. 9: 617–648, 1991; M. Baggiolini & C. A. Dahinden, Immunol. Today 15: 127–133, 1994). In addition, a chemokine SCM-1, which is presumed to be of type γ or C different from the above-mentioned two types, has recently been reported (T. Yoshida et al., FEBS Letters 360: 155–159, 1995).

Since chemokines are profoundly involved in bioprophylactic reactions as described above, the identification of a novel chemokine and the elucidation of its activity would highly contribute not only to the analysis of the immune response in which the chemokine is involved, but also to the development of a method for treating, preventing, or diagnosing the related diseases. A chemokine derived from human is useful for such purpose though, those from animals other than human, preferably mouse, are also needed for conducting requisite tests using experimental animals. It is therefore desirable to obtain a novel chemokine of human origin and its mouse counterpart. As is often the case with many physiologically active substances exhibiting the activity in only a slight amount, a novel chemokine cannot be obtained in ease.

Considering the fact that chemokines are secretory proteins which share the similarity of structure, the present inventors have concentrated their efforts on obtaining a novel chemokine by means of a signal sequence trap method.

Thus, by using a signal sequence trap vector originally constructed (Yoshida et al., FEBS Letters 360:155–159, 1995), a great number of cDNA fragments encoding secretory proteins or type I membrane proteins were separated from mitogen-stimulated normal human peripheral blood mononuclear cells, and their base sequences were compared with existing databases to find a cDNA fragment which potentially encodes a sequence characteristic of type CC chemokines.

A full-length cDNA was then isolated using the cDNA fragment, sequenced and identified. Finally, the inventors have obtained a DNA encoding a protein having a signal sequence which, after cleavage of the signal sequence, affords a secretory protein belonging to the mature type CC chemokines. The novel DNA was inserted into an appropriate expression vector, which was then transformed into an appropriate host cell. The transformants, when cultured, produced a type CC human chemokine-like protein capable of inducing the cell-migration of HUT78, and the like. The present inventors have succeeded in the isolation of mouse genomic DNA and cDNA using the DNA encoding human-derived chemokine-like protein, and, eventually, in the expression thereof in transformants. A base sequence of a DNA encoding a novel type CC chemokine-like protein from human and an amino acid sequence deduced therefrom are shown in SEQ ID NOS: 1 and 2. A base sequence of a DNA encoding a novel type CC chemokine-like protein from mouse and an amino acid sequence deduced therefrom are shown in SEQ ID NOS: 3 and 4.

DISCLOSURE OF INVENTION

The present invention provides a protein having the following characteristics:

1) its expression from peripheral blood mononuclear cells is induced in the presence of an immunological stimulus;

2) it is expressed mainly from thymus not from spleen, in the absence of the stimuli; and 3) it has the two contiguous cysteine residues characteristic of type CC chemokines.

The novel type CC chemokine-like protein of the present invention is expressed from peripheral blood mononuclear cells in the presence of an immunological stimulus, and the expression can be accelerated by phytohemagglutinin (PHA) or under the condition where the humoral immunity is induced. Particularly, the expression from monocytes is induced to higher extent in the presence of a cytokine selected from GM-CSF, IL-3 and IL-4 which participate in the induction of humoral immunity. The protein, as a characteristic, is not induced by TNF-α or IFN-γ which induces the cellular immunity, or LPS.

Based on the characteristics of the novel protein of the present invention that the organ which constitutively expresses it is thymus and that the production thereof is induced in response to an immunological stimulus, the present inventors named the protein "TARC" (Thymus and Activation-Regulated Chemokine). Accordingly, the novel protein and the DNA encoding it are referred herein to as "TARC" or "TARC protein", and "TARC DNA", respectively. The term "TARC" includes those derived from human and mouse; and if necessary, TARC of human origin may be referred as "human TARC" or "hTARC", and that of mouse origin as "mouse TARC" or "mTARC". Similarly, DNAs encoding these proteins are referred as human TARC DNA, hTARC DNA, mouse TARC DNA, or mTARC DNA, respectively. However, human TARC and the DNA encoding it may sometimes be referred simply as TARC and TARC DNA, respectively. In addition, in the present specification, the terms "DNA" and "gene" encoding TARC are used interchangeably. The DNA may be a synthetic or natural DNA.

Once a DNA encoding TARC is disclosed by the present invention, those one ordinary skilled in the art can easily obtain a TARC variant with a function and/or an activity substantially equivalent to that of the TARC having the above amino acid sequence, through the substitution, insertion or deletion of one or more amino acids by a method known in the art. A variant so obtained is, therefore, also included within the scope of TARC of the present invention.

Accordingly, the present invention also provides a human type CC chemokine-like protein comprising an amino acid sequence of the amino acid residues 24–94 in SEQ ID NOS: 1 and 2, and a variant thereof which containes, in said sequence, a substitution, insertion or deletion of an amino acid(s) or an amino acid sequence(s) and which has a function or an activity substantially equivalent to that of the said human type CC chemokine-like protein.

The present invention also provides a human type CC chemokine-like protein comprising an amino acid sequence of the amino acid residues 1–94 in SEQ ID NOS: 1 and 2, and a variant thereof which contains, in said sequence, a substitution, insertion or deletion of an amino acid(s) or an amino acid sequence(s) and which has a function or an activity substantially equivalent to that of the said human type CC chemokine-like protein.

Furthermore, the present invention also provides a mouse type CC chemokine-like protein comprising an amino acid sequence of the amino acid residues 24–93 in SEQ ID NOS: 3 and 4, and a variant thereof which contains, in said sequence, a substitution, insertion or deletion of an amino acid(s) or an amino acid sequence(s) and which has a function or an activity substantially equivalent to that of the said mouse type CC chemokine-like protein.

In addition, the present invention also provides a mouse type CC chemokine-like protein comprising an amino acid sequenced of the amino acid residues 1–93 in SEQ ID NO: 2, and a variant thereof which contains, in that sequence, a substitution, insertion or deletion of an amino acid(s) or an amino acid sequence(s) and which has a function or an activity substantially equivalent to that of the said mouse type CC chemokine-like protein.

A "variant" of TARC described in the present specification may contain chemical or biological alterations, or natural or artificial amino acids, so far as it exhibit a function or an activity substantially equivalent to that of TARC having the amino acid sequence described herein.

BRIEF DESCRIPTION OF DRAWINGS

FIG. 1 shows a base sequence of a cDNA for human TARC and the amino acid sequence deduced therefrom (residues 1–538 of SEQ ID NO: 1).

FIG. 2 is a comparison of amino acid sequence of the human TARC protein (residues 24–94 of SEQ ID NO: 2) of the present invention and those of seven known human type CC chemokines (residues 27–33 of SEQ ID NO: 5).

FIG. 3, panel B is a photograph of Northern blotting showing the expression of hTARC mRNA in various human tissues.

FIG. 8 shows a base sequence of a cDNA for mouse TARC and the amino acid sequence deduced therefrom (residues 1–465 of SEQ ID NO: 3).

FIG. 11 is a photograph showing the morphology of a tissue of Balb/c mouse after 24 hrs from the hypodermal injection of purified mouse TARC produced in insect cells, wherein the cell infiltration profile was observed after staining the tissue with hematoxylin-emosin.

FIG. 12 is a photograph showing the morphology of a tissue of Balb/c mouse after 24 hrs from the hypodermal injection of PBS alone, wherein the cell infiltration was observed after staining the tissue with hematoxylin-eosin.

FIG. 14, panel A is a graph showing the change in the amount of the specific binding of $^{125}$I-labeled TARC to Jurkat cells at various concentrations, and panel B is a Scatchard plot of the results shown in panel A.

FIG. 23 is a graph showing the relationships between the cytokine concentration and the level of TARC expression from normal human peripheral blood mononuclear cells.

FIG. 26-A is a graph showing the migration activity of TARC, which was secreted from normal human peripheral blood monocytes under the stimulation with a cytokine (IL-4, IL-3 or GM-CSF), on a T-cell line HUT78. FIG. 26-B is a graph which shows that the migration activity on HUT78 is disappeared only by anti-TARC antibody.

BEST MODE FOR CARRYING OUT THE INVENTION

Figure 3:
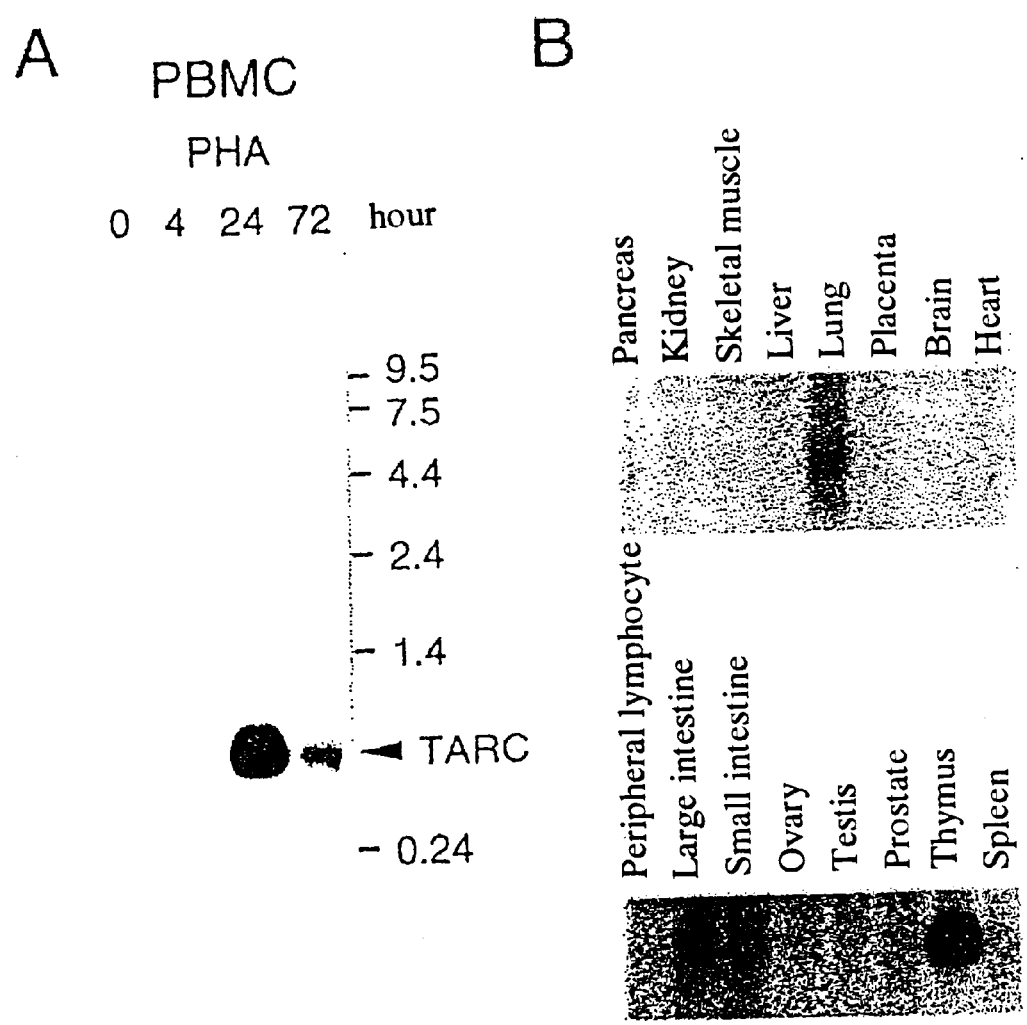
FIG. 3, panel A is a photograph of Northern blotting showing the expression of hTARC mRNA in normal human peripheral blood mononuclear cells at various times after the stimulation with PHA.

As a result of intimate study, the TARC of the present invention has proved to be a novel protein with properties distinct from those of the known type CC chemokines as follows.

(1) A human TARC is a protein of 94 amino acids at the DNA level, which, however, is presumed to give a mature protein which is a basic protein consisting of 71 amino acids with a molecular weight of about 8 kDa after cleavage of the signal sequence between alanines at positions 23 and 24.
(2) The mature TARC exhibits a significant homology to type CC chemokines, and in particular, all of the four cysteines conserved in type CC chemokines are also conserved in this protein (see, FIG. 2).
(3) It shows less than 30% homology to known type CC chemokines, with the highest homology of about 29% to RANTES.
(4) In contrast with known type CC chemokines, the tissue which constitutively expresses the protein is mostly restricted to thymus.
(5) It is expressed in peripheral blood mononuclear cells (PBMC) in the presence of immunological stimulus.
(6) The expression of the protein in PBMC is, for example, characterized by the following matters.
  1) The expression is stimulated more strongly by non-specific phytohemagglutinin (PHA) than anti-CD3 antibody specific to T cells, and is not stimulated by LPS which induces expression of conventional chemokines.
  2) The expression is induced by cytokines (GM-CSF, IL-3, IL-4) at a physiological concentration.
  3) The expression is not induced by TNFα and IFN-γ which induce expression of known chemokines;
  4) The expression of TARC mRNA is also induced by PHA, GM-CSF, IL-3, and IL-4;
  5) It is secreted only from monocytes under the stimulation of GM-CSF, IL-3, or IL-4. To the contrary, it is secreted only from lymphocytes under the stimulation with PHA, or PHA/PMA, and the induction with PHA is remarkably suppressed by PMA.
  6) The expression of mRNA for TARC in human peripheral blood mononuclear cells is hardly observed in the absence of stimulation or in the presence of LPS stimulation. However, the expression is induced by about 400 times under the stimulation with GM-CSF or IL-3, and by about 40 times under the stimulation with IL-4 or PHA.
(7) Mouse TARC has similar characteristics to those of human TARC, and is a protein of 93 amino acids at the DNA level, which is presumed to give a mature protein which is a basic protein consisting of 70 amino acids with a molecular weight of about 8 kDa after cleavage of the signal sequence between alanines at positions 23 and 24.
(8) Human TARC and mouse TARC are highly homologous with a homology of about 64.4%.
(9) It exhibits a leukocyte infiltration effect (chemokine-like activity).
(10) Receptor for TARC is expressed on certain T-cells (Jurkat, Molt3, CEM, Hut78, MT2, MT4, Hut102), peripheral blood lymphocytes, and activated peripheral blood T-cells.
(11) The TARC receptors on cells are independent of other chemokine receptors. The binding between the receptor and TARC is not inhibited by other chemokines.
(12) It binds specifically to DARC, one of the chemokine receptors on erythrocyte.
(13) Culture medium of normal human peripheral blood monocytes stimulated by IL-3 or GM-CSF induces a strong migration of HUT78 cells, but does not induce the migration when it is not stimulated or stimulated by IL-4. The ability of GM-CSF-treated cultured supernatant to induce the migration of Hut78 cell almost disappears when treated with guinea pig anti-TARC antibody.
(14) The expression of TARC in peripheral blood mononuclear cells under the stimulation with GM-CSF, IL-3, or IL-4 is suppressed by IFN-γ, which suppresses the humoral immunity induced by IL-4, and by IL-10, which suppresses the immune response generally.
(15) It specifically binds to CCR4 which has been reported as a receptor for MIP-1α, RANTES, MCP-1 (C. A. Power et al., J. Biol. Chem. vol. 270, No. 33, 19495–19500, 1995; which describes experiments with CCR4 expressed on *Xenopus laevis* ovules).

(16) It exhibits a migration activity on 293/EBNA-1 cells expressing CCR4.

From the above, it is apparent that TARC of the present invention is a novel cytokine belonging to type CC chemokine. Production of TARC is induced by an immunological stimulus, and its constitutive expression is almost restricted to thymus. In periphery, it is expressed from peripheral blood monocytes stimulated by certain cytokines (GM-CSF, IL-3, or IL-4).

Thus, TARC is possibly involved in the migration of immature T-cells into thymus tissue and in the differentiation and maturation of T-cells in that tissue. Further, the fact that production of the protein is induced by an immunological stimulus to peripheral blood mononuclear cells suggests that the protein could play an important role in inflammation and immune responses. Accordingly, TARC is believed to be a medically important protein which induces the migration and activation of leukocytes in the inflammatory reaction and the immune response, and plays an important role in, for example, the differentiation and maturation of T-cells in thymus.

The remarkable differences between TARC and the conventional type CC chemokines in the expression indicate that TARC has a specific physiological function(s). For instance, the fact that expression of TARC is stimulated to higher extent by non-specific phytohemagglutinin (PHA) than T-cell-specific anti-CD3 antibody demonstrates that TARC should be expressed from peripheral blood mononuclear cells (PBMC) under the stimulation with cytokines secreted from T-cells, rather than being secreted directly from T-cells. This is also apparent from the fact that the stimulation with LPS was not resulted in the expression of TARC, which generally induces the expression of most of the known chemokines.

Specifically, the expression of TARC is induced by various cytokines, especially by GM-CSF, IL-3, and IL-4 with strong effect. Since the first two cytokines are involved in maintenance of the homeostatic immune system, and IL-4 in the humoral immunity such as allergy, TARC is supposed to function under the circumstance where a humoral immunity is induced. Further, the fact that the expression of TARC is not induced by TNFα or IFN-γ, which is known to induce the expression of existing chemokines, also indicates that TARC is expressed and functions under a circumstance different from that for other chemokines. These facts, however, do not mean to exclude the possibility that TARC is expressed in lymphocytes besides normal human peripheral blood monocytes.

In addition, the expression of many chemokines is induced more strongly when PMA (phorbol myristate acetate) is added together with PHA, whereas that of TARC was reduced by such a combination. This fact suggests that the expression of TARC is under the similar control to that for expression of IL-4, supporting the supposition that TARC is involved in the humoral immunity as IL-4 is.

Cultured medium obtained by culturing normal human peripheral blood monocytes under the stimulation with GM-CSF or IL-3 exhibits a cell migration activity on HUT78 cells, as a recombinant TARC does. The migration activity of the cultured medium obtained under the GM-CSF stimulation was neutralized by an anti-TARC antibody. This fact suggests that, similar to a recombinant TARC, the TARC secreted from normal human peripheral blood monocytes also has a migration activity on cells expressing TARC-specific receptors.

As described above, in contrast with other chemokines, the expression of TARC from peripheral blood mononuclear cells is inducible under the conditions for the humoral immunity. The humoral immunity is induced by IL-4, and suppressed by IFN-γ, whereas the cellular immunity is induced by IFN-γ, and suppressed by IL-4. IL-10 suppresses the immunity generally. The fact that IFN-γ and IL-10 suppress the expression of TARC from normal human peripheral blood monocytes stimulated by GM-CSF, IL-3, and IL-4 indicates that TARC is expressed under the condition in which immune response, specifically humoral immunity, is induced, and suppressed under the condition in which the cellular immunity is induced. Accordingly, TARC is supposed to be expressed and to function in a situation similar to that for the humoral immunity such as allergy, atopy, and asthma among others.

The elucidation of functions of TARC of the present invention would contribute to the elucidation of, for example, the functions of thymus, the differentiation and maturation of T-cells, control of the inflammatory reaction and immune response, and thereby providing a new mean for inducing or suppressing the inflammatory reaction or immune response.

In addition, an anti-TARC antibody and a gene (DNA) encoding TARC of the present invention can be used to analyze the gene mutations of TARC as well as the expression states of corresponding mRNA and protein, and is useful in providing a new mean for revealing etiology of or diagnosing diseases associated with the blood and immune systems. Accordingly, they are useful for developing a new method of diagnosing and treating such diseases.

Furthermore, a gene (DNA) encoding TARC of the present invention can also be useful in a gene therapy against, for example, hereditary diseases due to an abnormality in the TARC gene, various cancers, and lethal infections such as AIDS, by administrating it into bodies directly or after inserting it into an appropriate vector and introducing it ex vivo into cultured cells.

Besides the above, it would also be possible to diagnose, for example, allergy, atopy, and asthma by measuring the blood concentration of TARC. In addition, it would be possible to treat or prevent allergy, atopy, asthma and the like by suppressing the expression or activity of TARC, and to induce the humoral immune condition while suppressing the cellular immune condition through the stimulation of the expression or activity of TARC.

Accordingly, the present invention also provides a pharmaceutical composition comprising TARC of the present invention or a variant thereof. The pharmaceutical compositions of the present invention includes those for prophylaxis, treatment, and diagnosis, and the doses and administration routes can be determined as appropriate depending on, for example, the purpose and conditions of the subject to be treated, by using conventional methods. It will be easily understood that, since the TARC is a physiologically active substance, its acute toxicity would not be critical within the amount at which it exhibits the activity, that is, within the dosage for pharmaceutical composition of the present invention.

For the various purposes, TARC and a fragment thereof containing the active part, a monoclonal or polyclonal antibody against said TARC or a fragment thereof, and a receptor which specifically binds the TARC are also useful.

Accordingly, the present invention also provides a monoclonal antibody specific to TARC, and a hybridoma producing said antibody. As described in the Examples below, such antibodies and hybridomas can be produced using known methods established in the art.

In the light of the activities of the present TARC protein, the detection of agonists or antagonists for TARC would be useful in the treatment, prophylaxis, or diagnosis of diseases or disorders associated with TARC. A screening of such substances can be achieved by exploiting, for example, the assay method of TARC protein, or the receptor specificity of the TARC protein, as herein disclosed.

Thus, the present invention also provides a method for screening an agonist or antagonist of the TARC protein, which comprises the steps in which a sample suspected to contain said agonist or antagonist, cells secreting said protein, and a cytokine inducing the secretion of said protein are mixed, and the secreted amount of said protein is measured.

The assay of the TARC protein can be achieved, for example, according to the protein assay method described in the Examples below.

The cytokine usable in the above method includes, for example, GM-CSF, IL-3, and IL-4, and the cells secreting TARC includes, for example, peripheral blood mononuclear cells.

In addition, the present invention also provides a method for screening an agonist or antagonist of TARC protein, which comprises the steps in which a sample suspected to contain said agonist or antagonist is reacted with a receptor specific to said protein, and the binding activity and/or reactivity is measured.

The receptor usable in the above method includes, for example, CCR4, and the measurement of the binding activity or reactivity may be achieved by the method described in the Examples below.

A method for producing and identifying TARC of the present invention will be described below. The followings are provided only for illustration purpose and, unless specifically indicated, techniques known to those skilled in the art for gene recombination, transformation of host cells, production of a recombinant protein using transformants, and separation and purification of an expressed protein, and the like, and immunological methods can be used as appropriate.

I. Sequencing of a DNA Encoding TARC Protein

A DNA fragment containing a DNA encoding the TARC protein of the present invention can be obtained from, for example, a cDNA library derived from normal human peripheral blood mononuclear cell (PBMC) stimulated with phytohemagglutinin (PHA).

(1) Preparation of Probe

A probe for cloning a gene encoding the TARC protein from a cDNA library is prepared as follows.

Since TARC is a secreted protein, mRNA for TARC has a region encoding a signal sequence at the 5' terminus. Therefore, poly(A)$^+$RNAs are first extracted from PHA-stimulated PBMC using QuickPrep mRNA Purification Kit (Pharmacia). Single-stranded DNAs are then generated from these mRNAs using random primers (GIBCO-BRL), and an oligo(dC) anchor is attached thereto at the 3' terminus.

Then, double-stranded DNAs are synthesized using an oligo(dG) primer, degraded by ultra-sonication, and restored with T4 polymerase. The material is attached to Uni-amp adapter (Clontech), subjected to an agarose electrophoresis followed by extracting 300–600 bp fragments highly containing the 5' terminal sequences. The fragments thus obtained are inserted into a signal sequence trap vector pDREF-CD4ST (Yoshida et al., FEBS Letters 360: 155–159, 1995). This vector is a shuttle vector containing a replication origin of Epstein-Barr virus (EBV), and is capable of self-replicating in the presence of the EBNA-1 protein. This vector also contains a DNA encoding human CD4 lacking its signal sequence inserted downstream from a strong EF-1α promoter so that it allows the expression of CD4 in transfected Raji cells, when an unknown cDNA fragment encoding a signal sequence is inserted correctly and in frame between the two regions and used to transfect Raji cells.

Raji cells are transfected with the vector pDREF-CD4ST to which the above fragments have been inserted, and the transfected Raji cells which became CD4-positive are enriched by sorting, and then plasmids are recovered therefrom. Individual plasmid is then re-introduced into Raji cells, and after confirming the expression of CD4, plasmids which contains the inserted cDNA fragments potentially encoding a signal sequence are finally separated. The base sequences of the cDNAs inserted in these plasmids are determined and compared with the data bases to select a cDNA fragment encoding a sequence characteristic of type CC chemokines. The resultant cDNA which potentially encodes a desired novel protein is labeled with, for example, $^{32}$P, and used as a probe in the screening of a cDNA library derived from PHA-stimulated human PBMC to obtain a full length cDNA.

The cDNA library is constructed in a conventional manner according to, for example, the following method. Poly (A)$^+$RNAs are extracted from PHA-stimulated human PBMC using QuickPrep Micro mRNA Purification Kit (Pharmacia), and cDNAs are synthesized from these poly (A)$^+$RNAs using an oligo(dT) as a primer together with reverse transcriptase, and then inserted into, for example, a vector pSPORT1 (GIBCO-BRL). Screening of the library using the probe obtained in the above section is achieved in any one of the methods known to those skilled in the art, such as a recombinant phage plaque hybridization or a recombinant *E. coli* colony hybridization.

The inserted cDNA in the recombinant plasmid so obtained is then sequenced. The sequencing is achieved, for example, in the following manner. Firstly, the inserted fragment is cleaved at the restriction enzyme sites located in said fragment, and each cDNA fragment is subcloned into an appropriate sequencing vector such as pBluescript (Stratagene). Then, the base sequences of the cloned fragments are determined using, for example, the method of Sanger (F. Sanger et al., Proc. Natl. Acad. Sci. USA, 74: 5463–5467, 1977).

II. Expression of a Recombinant TARC Protein

A DNA encoding the TARC protein of the present invention is incorporated into an appropriate expression vector, and the expression vector so obtained is introduced into an appropriate host cell, such as a bacterial, yeast, insect, or animal cell, to obtain a transformant.

Examples of a vector suitable for the expression of TARC DNA of the present invention include, but not limited to, pRSET, pGEMEX and pKK233-2 for bacterial host cells, pYES2 for yeast host cells, pVL1393 for insect host cells, and pEF-BOS, pSRα and pDR2 for animal host cells.

In the case of prokaryotic microorganisms such as *E. coli*, DNA encoding TARC can be expressed under the control of a strong promoter (such as a T7 promoter) as a precursor protein which comprises of a signal sequence derived from a natural precursor of a protein secreted from a prokaryotic microorganism (for example, a signal peptide OMPa) and TARC protein of mature form.

In the case of yeast, it can be expressed as a precursor protein which comprises of a sequence derived from a natural precursor substance of a protein secreted from yeast (for example, the prepro-sequence of pheromone α) and the mature TARC protein.

In the case of animal cells, a gene encoding TARC protein can be inserted downstream from a strong promoter (for example, a EF-1α promoter) in an appropriate expression vector, and introduced into an animal cell (for example, a CHO dhfr-cell) together with an effective selection marker (such as dihydrofolate reductase), and the transformants resistant against an agent (in this case, methotrexate) are selected to establish a cell line with high expression ability.

In the case of human cells, a gene encoding TARC protein is incorporated into a virus or retrovirus, and the human cells are infected with the recombinant virus. When the transformants so obtained are cultured under the condition suitable for the expression of TARC, the TARC protein is produced by the transformants. Alternatively, the mature TARC protein can also be totally synthesized by a known method using, for example, solid phase reactions and taking necessary account of the presence of two disulfide bondings.

Thus, the present invention includes a TARC synthesized chemically or by genetic engineering as described above.

III. Generation of an Anti-TARC Antibody

As described above, antibodies specific for TARC of the present invention is useful in the elucidation of physiological events, as well as in the treatment, prophylaxis or diagnosis of diseases or disorders associated with the TARC activity. Thus, the present invention also provides an antibody against the TARC protein.

Methods for generating an antibody (polyclonal and monoclonal) against a protein are well known in the art.

For example, a peptide synthesized using a conventional peptide synthesizer on the basis of a part of the amino acid sequence shown in SEQ ID NO: 2 or 4, or a TARC protein which is produced in cells such as bacterial, yeast, animal, or insect cells transformed with a TARC-expressing vector and purified by conventional protein-chemical methods, can be used as an immunogen for immunizing an animal such as a mouse, rat, hamster, or rabbit. A polyclonal anti-TARC antibody is then prepared from the serum of the immunized animal.

Alternatively, hybridoma may be produced by removing cells from spleen or lymph node of an immunized mouse or rat and fusing them with myeloma cells, according to the method of Kohler and Milstein [Nature, 256, 495–497 (1975)] or the method of Ueda [Proc. Natl. Acad. Sci. USA, 79, 4386–4390(1982)] which is an improved method of the former. Then, a monoclonal anti-TARC antibody may be produced from the hybridoma. Steps for preparing a monoclonal antibody is exemplified below:

(a) immunization of a mouse with a TARC protein;
(b) removal of spleen from the immunized mouse and separation of spleen cells;
(c) fusion between the separated spleen cells and mouse myeloma cells according to the method described by Kohler et al. (see above) in the presence of a fusogenic agent (for example, polyethylene glycol);
(d) cultivation of the resultant hybridoma cells in a selective medium in which unfused myeloma cells do not grow;
(e) selection of a hybridoma cell producing a desired antibody by means of, for example, an ELISA or immunoelectroblotting, and cloning thereof by, for example, a limiting dilution method; and
(f) cultivation of the hybridoma cell producing a monoclonal anti-TARC antibody, and separation of the monoclonal antibody from the culture.

(IV) Detection of TARC mRNA and TARC Protein

The TARC mRNA and TARC protein of the present invention can be detected by any one of conventional methods for specifically detecting a mRNA or a protein.

For example, mRNA can be detected by Northern blotting or in situ hybridization using an antisense RNA or cDNA as a probe. Alternatively, mRNA can also be detected by a polymerase chain reaction (hereinafter, referred to as PCR) using an appropriate combination of primers, after conversion into cDNA using reverse transcriptase.

The presence of the protein may be confirmed by a conventional immunoprecipitation method or Western blotting using a TARC-specific antibody obtained in the above section (III).

V. Immunological Assay for the TARC Protein

For example, to a fixed amount of the TARC labeled with radioisotope, enzyme such as peroxidase or alkaline phosphatase, fluorescent dye, or the like, are added an unlabeled TARC of known concentration and a monoclonal or serum-derived polyclonal anti-TARC antibody, and the antigen-antibody competitive reaction is allowed to proceed. The assay is carried out using different concentrations of the unlabeled antigen. The labeled antigen bound to the antibody is separated from the unbound labeled antigen by an appropriate method, and the radioactivity, enzyme activity, or fluorescence intensity bound to the antibody is measured. As the amount of the unlabeled antigen increases, the amount of the labeled antigen bound to the antibody decreases. This relationship is plotted to obtain a standard curve. Alternatively, a so-called sandwich method is also availabe, in which one of two different monoclonal antibodies each recognizing different epitopes on a TARC protein is immobilized and the other is labeled by any one of the above methods, and the amount of the TARC bound to the immobilized antibody is detected and determined.

In the next step, a sample containing unknown amount of antigen is added to the above-mentioned reaction system instead of the unlabeled antigen of known concentration. After the reaction, the radioactivity, enzyme activity, or fluorescence intensity is obtained and compared to the standard curve to determine the amount of the antigen (i.e., the TARC protein) in the sample. In such a way, a new method of monitoring inflammatory or immune response, or differentiation and maturation of T-cells can be provided.

VI. Verification of Chemokine Activity of TARC Protein

The chemokine activity of the TARC protein of the present invention can be verified by, for example, the following procedures. For in vitro verification of the chemokine activity, TARC can be introduced into one side of a cultivation container partitioned with an intervening porous filter having a constant pore size. The target cells are introduced into the other side, and the number of cells migrated through the filter pore into the side containing TARC after a definite period is then compared with that due to random migration. For in vivo verification of the chemokine activity, a purified TARC protein can be subcutaneously administrated into an animal, and the infiltration and accumulation of the cells can be detected using histological methods The present invention will be further illustrated in the following Examples.

EXAMPLE 1

Isolation of a DNA Encoding Human TARC

I. Cloning of Human TARC cDNA (1) Preparation of a cDNA Library Derived from Phytohemagglutinin-stimulated Human Peripheral Blood Mononuclear Cells A cDNA library of normal human peripheral blood mononuclear cells stimulated with phytohemagglutinin (PHA) was prepared as follows, according to a conventional method known in a literature (J. Sambrook et al., Molecular Cloning: A Laboratory Manual, second edition, Cold Spring Harbor Laboratory, New York (1989)) and using a cDNA synthesis system and a cDNA cloning system manufactured by GIBCO-BRL.

Firstly, poly(A)$^+$RNAs were extracted from normal human peripheral blood mononuclear cells stimulated with PHA, using QuickPrep Micro mRNA Purification Kit (Pharmacia). Human peripheral blood mononuclear cells ($2 \times 10^7$ cells) stimulated with PHA for 72 hours were lysed with cell lysis solution appended to the kit. An oligo-dT resin was then added thereto, and mixed for 3 minutes for allowing poly(A)$^+$RNAs to bind to the resin. The resin was then centrifuged for 1 minute at 12,000 rpm in a TOMY centrifuge MRX-150 (TOMY Seiko). The precipitation formed was washed three times with a high salt washing solution, and five times with a low salt washing solution, and then eluted with an eluent. To the eluate were added 0.1 volume of 3M sodium acetate and 2 volumes of ethanol. The mixture was cooled for 1 hour at −80° C., and centrifuged for 5 minutes at 12,000 rpm in a TOMY centrifuge MRX-150 (TOMY Seiko) to precipitate the poly(A)$^+$RNAs, which were then dissolved in sterile distilled water. The amount of recovered poly(A)$^+$RNAs was calculated from the absorbance at 260 nm. Ten $\mu$g of poly(A)$^+$RNAs was obtained from the PHA-stimulated human peripheral blood mononuclear cells.

Synthesis of cDNA was carried out using the purified poly(A)$^+$RNAs as templates in the following manner. Single-stranded DNAs were first synthesized by reacting 4 $\mu$g of poly(A)$^+$RNAs as a template using a reverse transcriptase SUPER SCRIPT II RT (GIBCO-BRL) for 1 hour at 37° C. in a reaction buffer (50 mM Tris-HCl, pH 8.3, 75 mM KCl, 3 mM MgCl$_2$, 10 mM DTT, 500 $\mu$M dNTPs (dATP, dGTP, dCTP, dTTP), 50 $\mu$g/ml NotI primer-adapter (GIBCO-BRL) and 20,000 U/ml reverse transcriptase SUPER SCRIPT II RT). The sequence of the NotI primer-adapter is shown as SEQ ID NO: 5. These single-stranded DNAs were reacted as templates for 2 hours at 16° C. in a reaction buffer (25 mM Tris-HCl, pH 7.5, 100 mM KCl, 5 mM MgCl$_2$, 10 mM (NH$_4$)$_2$SO$_2$, 1.2 mM DTT, 0.15 mM β-NAD+, 250 $\mu$M dNTPs (dATP, dGTP, dCTP, dTTP), 65 U/ml DNA ligase, 250 U/ml DNA polymerase I, and 13 U/ml RNase H) to synthesize cDNAs. T4 DNA polymerase was then added thereto at a final concentration of 65 U/ml, and further reacted for 5 minutes at 16° C. to obtain double-stranded DNAs. These double-stranded DNAs were reacted for 16 hours at 16° C. in a reaction buffer (50 mM Tris-HCl, pH 7.6, 10 mM MgCl$_2$, 1 mM DTT, 1 mM ATP, 5% PEG 8000, 200 $\mu$g/ml SalI adapter (GIBCO-BRL), and 100 U/ml T4 DNA ligase) to ligate them to a SalI adapter. The SalI adapter is a double-stranded DNA in which the DNAs shown as SEQ ID NOS: 6 and 7 have annealed. The resultant cDNAs were inserted between the NotI and SalI sites in a vector pSPORT1 to obtain a cDNA library.

(2) Preparation of a cDNA Library for Signal Sequence Trapping

The cDNAs enriched in those corresponding to the 5' terminal regions of mRNA were prepared from PHA-stimulated human peripheral blood mononuclear cells, and used for preparation of a signal sequence trap library according to a conventional method described in a literature (J. Sambrook et al., Molecular Cloning: A Laboratory Manual, second edition, Cold Spring Harbor Laboratory, New York (1989)) using a cDNA synthesis system, a 5' RACE system and a cDNA cloning system manufactured by GIBCO-BRL.

Firstly, the cDNAs enriched in those corresponding to the 5' terminal regions of mRNA were synthesized in the following manner, using the poly(A)$^+$RNAs derived from PHA-stimulated human peripheral blood mononuclear cells. Using a reverse transcriptase SUPER SCRIPT II RT (GIBCO-BRL), 5 $\mu$g of the poly(A)$^+$RNAs as a template was reacted for 1 hour at 37° C. in a reaction buffer (50 mM Tris-HCl, pH 8.3, 75 mM KCl, 3 mM MgCl$_2$, 10 mM DTT, 500 $\mu$M dNTPs (dATP, dGTP, dCTP, dTTP), 150 ng random primers (GIBCO-BRL), and 20,000 U/ml reverse transcriptase SUPER SCRIPT II RT) to synthesize single-stranded DNAs. To this reaction was added 6N NaOH at a final concentration of 0.4 N, and further reacted for 30 minutes at 65° C. After hydrolysis of the template poly(A)$^+$RNAs, 6N acetic acid was added at a final concentration of 0.4 N to neutralize the mixture. To the mixture was added an equal volume of a phenol/chloroform (1:1) mixture saturated with 10 mM Tris-HCl (pH 8.0), and the mixture was stirred, and centrifuged for 5 minutes at 12,000 rpm in a TOMY centrifuge MRX-150 (TOMY Seiko). The aqueous layer was removed, 0.2 volumes of 3M sodium acetate and 2 volumes of ethanol were added thereto, and cooled for 1 hour at −80° C. After centrifuging for 5 minutes at 12,000 rpm in a TOMY centrifuge MRX-150 (TOMY Seiko), the precipitate was dissolved in sterile distilled water. These single-stranded DNAs were reacted for 10 min at 37° C. in a reaction buffer (20 mM Tris-HCl, pH 8.4, 50 mM KCl, 1.5 mM MgCl$_2$, 200 $\mu$M dCTP, and 400 U/ml terminal deoxynucleotidyl transferase) to attach an oligo-dC tail at the 3' termini. Then, the terminal deoxynucleotidyl transferase was inactivated by heating at 70° C. for 5 minutes. These single-stranded DNAs having oligo-dC tail were reacted for 2 hours at 16° C. in a reaction buffer (25 mM Tris-HCl, pH 7.5, 100 mM KCl, 5 mM MgCl$_2$, 10 mM (NH$_4$)$_2$SO$_4$, 1.2 mM DTT, 0.15 mM β-NAD+, 250 $\mu$M dNTPs (dATP, dGTP, dCTP, dTTP), 500 ng anchor primer (SEQ ID NO: 8), 65 U/ml DNA ligase, 250 U/ml DNA polymerase I, and 13 U/ml RNase H) to synthesize double-stranded DNAs. The anchor primer was synthesized with a DNA synthesizer (Cyclone Plus DNA Synthesizer, Miligen/Biosearch). β-Linked beta-cyanoethylphosphoamidite reagents from Miligen/Biosearch were used in the synthesis. After the synthesis was completed, the resultant oligonucleotide was eluted from the synthesis column with 2 ml of aqueous ammonia (28%, Nacalai Tesque), and treated for 5 hours at 60° C. to detach the protective groups. To the deprotected oligonucleotide was added 10 volumes of butanol, and the mixture centrifuged for 10 minutes at 3,000 rpm in a TOMY centrifuge (TOMY Seiko) to precipitate and recover the product. The recovered oligonucleotide was dissolved in sterile distilled water, and determined by measuring the absorbance at 260 nm.

The double-stranded DNAs were partially degraded for 150 seconds under cooling with a TOMY sonicator UD-201 (TOMY Seiko) at the maximum output. T4 DNA polymerase was then added thereto at a final concentration of 65

U/ml and allowed the reaction to proceed for 5 minutes at 16° C., and for 16 hours at 16° C. in a reaction buffer (50 mM Tris-HCl, pH 7.6, 10 mM MgCl$_2$, 1 mM DTT, 1 mM ATP, 5% PEG 8000, 200 µg/ml UNI-Amp adapter, and 100 U/ml T4 DNA ligase) to ligate the DNAs to the UNI-Amp adapter (Ciontech). The UNI-Amp adapter is an adapter in which the DNAs shown as SEQ ID NOS: 9 and 10 have annealed. The partially-degraded double-stranded DNAs so obtained were used as templates in a PCR reaction conducted in a reaction buffer (10 mM Tris-HCl, pH 8.3, 50 mM KCl, 1.5 mM MgCl$_2$, 0.1% gelatin, 200 µM dNTPs (dATP, dGTP, dCTP, dTTP), 400 nM UAP primer (GIBCO-BRL), 400 nM UNI-Amp primer (Clontech), and 100 U/ml Ampli-Taq DNA polymerase I). The sequences of the UAP primer and the UNI-Amp primer are shown as SEQ ID NOS: 11 and 12, respectively. The PCR was conducted on a DNA Thermal Cycler (Perkin-Elmer) using AmpliTaq Kit purchased from Takara Shuzo. The reaction was conducted as follows: a pretreatment for 3 minutes at 94° C.; 30 cycles of 45 seconds at 94° C., 45 seconds at 58° C., and 2 minutes at 72° C.; and the final treatment for 3 minutes at 72° C.

The cDNAs enriched in those corresponding to the 5' terminal regions of mRNA were inserted between the SalI and XbaI sites of pDREF-CD4ST separately constructed (Yoshida et al., FEBS Letters 360: 155–159, 1995) to obtain a signal sequence trap library. The resultant signal sequence trap library was introduced into a human B-cell line Raji, and a clone capable of expressing CD4 on the surface was identified to select a gene fragment which comprises a signal sequence, in the following manner.

(3) Signal Sequence Trapping

Ten µg of the signal sequence trap cDNA library prepared in the above (2) consisting of the cDNAs enriched in the 5' terminal regions of mRNA and derived from PHA-stimulated human peripheral blood mononuclear cells was introduced into 1×10$^7$ Raji cells suspended in 500 µl of PBS by electroporation. The electroporation was conducted on a Gene Pulser from BioRad set at a voltage of 250V and a capacitance of 500 µF. Raji cells in which the cDNA library has been introduced were obtained by cultivating the cells for one week in the presence of hygromycin (200 µg/ml) and by selecting the cells exhibiting resistance to the agent. Those cells exhibiting resistance to the agent were reacted with a mouse anti-human CD4 antibody (OKT4, obtained from ATCC) for 30 minutes at 4° C., and, after washing, further reacted with a magnetic beads-labeled sheep anti-mouse IgG antibody (Dynabeads, purchased from Dynal) for 30 minutes at 4° C. The cells expressing CD4 on their cellular surface labeled with the magnetic beads were separated using a magnetic separator. This magnetic separation was repeated three times, finally providing a cell population, 45% of which is expressing CD4 on their cellular surface.

From this cell population, plasmid DNAs were recovered using Magic Minipreps DNA Purification System (Promega), and introduced again into E. coli DH10B. These E. coli cells were plated onto LB-ampicillin-agar plates (10 g tryptone, 5 g yeast extract, 10 g NaCl, 15 g agar, 50 µg/ml ampicillin per one liter distilled water), and incubated overnight at 37° C. Individual colony of E. coli generated on the plates was incubated overnight at 37° C. in 5 ml LB-ampicillin medium (10 g tryptone, 5 g yeast extract, 10 g NaCl, 50 µg/ml ampicillin per one liter distilled water). From these cultured medium, plasmid DNAs were purified using Magic Minipreps DNA Purification System (Promega), and introduced again into 1×10$^7$ Raji cells suspended in 500 µL PBS by electroporation. These Raji cells were reacted with a mouse anti-CD4 antibody (OKT4, obtained form ATCC) for 30 minutes at 4° C., and, after washing, further reacted with a FITC-labeled rabbit anti-mouse IgG (Fab')2 antibody (purchased from Dako) for 30 minutes at 4° C. The cells expressing CD4 on their cellular surface which was labeled with FITC were identified using FacStar Plus (Becton-Dickinson). A hundred colonies of E. coli were checked, and 42 clones inducing the expression of CD4 on the cellular surface were finally obtained.

The base sequences of these clones were determined by the Sanger method using A.L.F. II Automated Sequencer and Autoread Sequence Kit manufactured by Pharmacia. Comparison of the sequences of these clones to existing data bases revealed that clone 98 contains two contiguous cysteines at 9 amino acids downstream from the putative signal sequence cleavage site, and has a structural property consistent with that of type CC chemokine, one of the cell migratory cytokines.

(4) Cloning of a Full-length cDNA for Human TARC

In order to obtain a full-length cDNA of clone 98, the 207 bp cDNA fragment of clone 98 was labeled with $^{32}$P using Multiprime DNA Labeling System (Amersham Japan), and used as a probe for screening the cDNA library of PHA-stimulated human peripheral blood mononuclear cells prepared in the above (1) by a colony hybridization method. The colony hybridization was conducted by a known procedure described in a literature (J. Sambrook et al., Molecular Cloning: A Laboratory Manual, second edition, Cold Spring Harbor Laboratory, New York (1989)).

E. coli DH10B cells containing the human PHA-activated peripheral blood mononuclear cell cDNA library were plated onto LB-ampicillin-agar plates (10 g tryptone, 5 g yeast extract, 10 g NaCl, 15 g agar, 50 µg/ml ampicillin per one liter distilled water), and incubated overnight at 37° C. The colonies of E. coli generated on the plates were transferred onto nylon membranes (Hybond-N$^+$, Amersham Japan), and then subjected to SDS treatment (10% SDS), alkaline-denaturation (0.5 N NaOH, 1.5M NaCl), and washing (2×SSC). These membranes were subjected to hybridization using the $^{32}$P-labeled clone 98 as a probe. The hybridization was conducted overnight at 42° C. using 6×SSC (1×SSC consists of 0.15 M NaCl, 0.015 M sodium citrate), 50% formamide, 0.5% SDS, 5-fold Denhardt's solution, and 100 µg/ml salmon sperm DNA as the hybridization buffer. After washing the membranes with a buffer consisting of 2×SSC and 0.1% SDS for 10 minutes at room temperature, and twice with a buffer consisting of 0.2×SSC and 0.1% SDS for 30 minutes at 60° C., X-ray films (Kodak) were exposed to the membranes, and developed. From the developed films, colonies which reacted with the probe were identified, and one cDNA clone (clone D3A) was finally obtained. The cDNA inserted in this clone D3A was sequenced by the Sanger method using A.L.F. II Automated Sequencer and Autoread Sequence Kit manufactured by Pharmacia, and further subjected to various examinations described below. In result, said cDNA proved to encode an objective novel type CC chemokine-like protein (TARC).

II. Determination the Structure of Human TARC (1) Analysis of the Base Sequence of the hTARC cDNA and the Amino Acid Sequence Encoded Thereby The base sequence of clone D3A obtained in the above I. (4) was determined by the Sanger method using A.L.F. II Automated Sequencer and Autoread Sequence Kit manufactured by Pharmacia. The base sequence of the cDNA clone D3A and the amino acid sequence of the open reading frame which does not internally contain any translational termination codon are shown in FIG. 1.

As shown in FIG. 1, it was revealed that the gene inserted in clone D3A contains an open reading frame consisting of 94 amino acids, and that, at the N-terminus, it has a highly hydrophobic amino acid sequence characteristic of signal peptides. The calculated molecuar weight of the 94 a.a. protein is 10,507. The putative cleavage site of the signal peptide is between Ala-23 and Ala-24 according to a calculation, and indicated in FIG. 1 by a vertical bar. The two contiguous cysteines characteristic of type CC chemokines are shown at 9 amino acids downstream from this cleavage site.

In addition, the putative mature protein consisting of 71 amino acid generated by cleavage of the signal peptide is presumed to be a secreted protein. The molecular weight of the putative mature secreted protein 71 amino acids is calculated to be 8,082, and the calculated isoelectric point is 9.7.

(2) Similarity in Sequence to Type CC Chemokines

The amino acid sequence of hTARC was compared with those of the known type CC chemokines using FASTA and Clustal V programs. The results are shown in FIG. 2. In FIG. 2, the amino acids conserved in all of the type CC chemokines including hTARC are shadowed and boxed with a bold line, whereas the amino acids conserved in most of the chemokines are merely shadowed. The numbers at the right margin indicate the degrees of homology of hTARC to each of the other type CC chemokines in percentage.

From FIG. 2, it has been shown that the amino acid sequence of hTARC protein of the mature secreted form has 29%, 26%, 28%, 24%, 24%, 24%, and 28% homology to RANTES, MIP-1α, MIP-1β, I-309, MCP-1, MCP-2, and MCP-3, respectively, which are all classified as the type CC chemokine. In addition, it has been shown that the four cysteines conserved in all of the CC chemokines are also conserved in hTARC. The above results suggest that the resultant amino acid sequence represents a novel human type CC chemokine.

III. Analysis of the Expression of hTARC mRNA by Northern Blotting

Multiple tissue blots were purchased from Clontech, which have been prepared by electrophoresing 2 µg each of poly(A)+RNAs isolated from various human tissues and transferring them onto a nylon membrane. In addition, poly(A)+RNAs were extracted from human peripheral blood mononuclear cells at 0, 4, 24, and 72 hours after stimulation with PHA, using QuickPrep Micro mRNA Purification Kit (Pharmacia). One µg of the isolated poly(A)+RNAs was electrophoresed on a 1% agarose gel containing 0.66 M formaldehyde, and transferred onto a nylon membrane (Hybond-N+, Amersham Japan). These membranes were subjected to hybridization using, as a probe, the SmaI-PstI fragment of the hTARC cDNA clone D3A labeled with $^{32}P$ by means of Multiprime DNA Labeling System (Amersham Japan). The hybridization was conducted overnight at 42° C. using, as a hybridization solution, 5×SSPE (1×SSPE consists of 0.18 M NaCl, 0.01 M sodium phosphate, pH 7.5, 1 mM EDTA), 50% formamide, 2% SDS, 10×Denhardt's solution, 100 µg/ml salmon sperm DNA. The membranes were washed with a buffer consisting of 2×SSC and 0.1% SDS for 10 minutes at room temperature, and twice with a buffer consisting of 0.2×SSC and 0.1% SDS for 30 minutes at 60° C. Then, X-ray films (Kodak) were exposed to the membranes, and developed for analysis. The results of TARC mRNA expression at various times after the PHA-stimulation are shown in FIG. 3A, and the expression of TARC mRNA in each of various human tissues is shown in FIG. 3B.

FIG. 3A indicates that the expression of mRNA for hTARC in human peripheral blood mononuclear cells is not detectable in the absence of stimulation. When stimulated with PHA, the expression of mRNA was not detected 4 hours after the stimulation, but reached almost maximal 24 hours after the stimulation, and was maintained even 72 hours after the stimulation, although at a lower level.

In addition, it can be seen from FIG. 3B that mRNA for hTARC is highly expressed in thymus, and at a lower level in lung, large and small intestines, whereas it is hardly detected in other tissues.

These results indicate that, as opposed to the other type CC chemokines, hTARC is constitutively expressed only in thymus, and its production is induced by an immunological stimulus.

EXAMPLE 2

Figure 4:
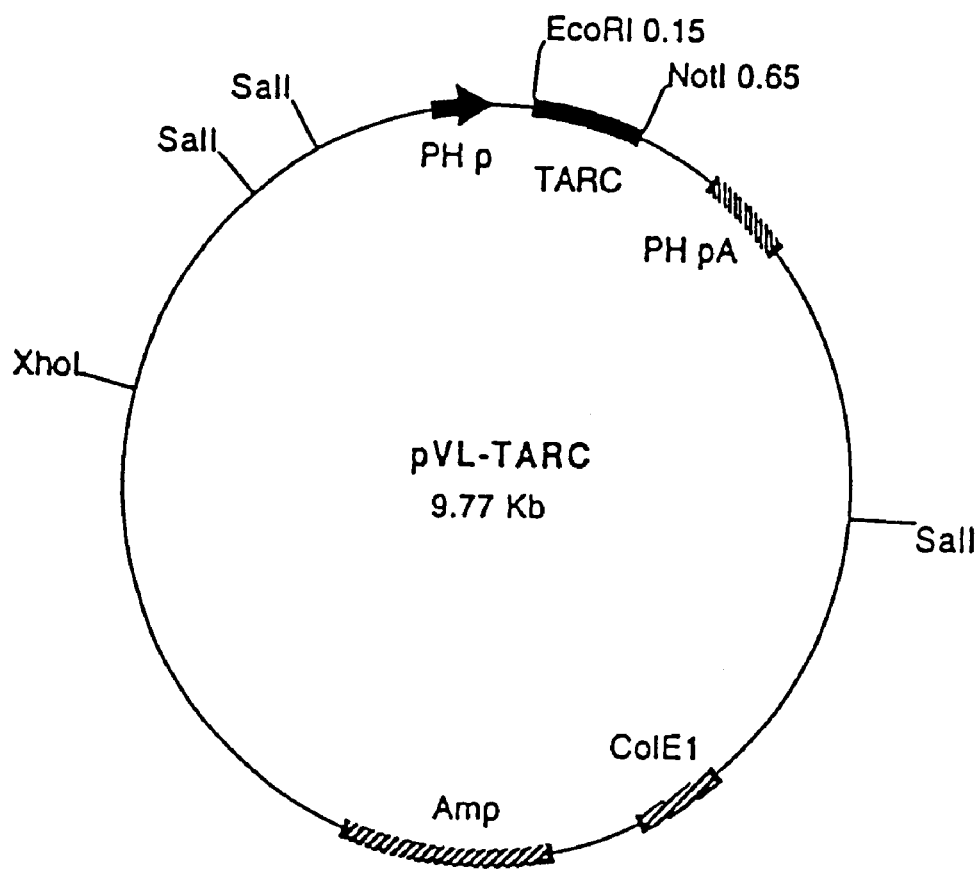
FIG. 4 is a gene map of a recombinant vector pVL-TARC.

Expression of a Recombinant Human TARC in Silkworm Cells (1) Construction of a Recombinant Vector pVL-TARC for Expression of hTARC DNA in Silkworm Cells A 0.5 kb DNA fragment which has EcoRI and NotI sites at the both termini and which contains the hTARC sequence spanning from the translational initiation codon to the translational termination codon was obtained by simultaneously digesting clone D3A described in Example 1 with EcoRI and NotI. This DNA fragment was inserted between the EcoRI site and the NotI site in pVL1393 (Invitrogen) used for preparation of a recombinant baculovirus to obtain a recombinant vector pVL-TARC. The gene map of the recombinant vector pVL-TARC is shown in FIG. 4.

(2) Culture of Transformants

The recombinant vector pVL-TARC and a linear DNA of AcNPV having a lethal deletion were then concurrently introduced into Sf9 insect cells to obtain a recombinant baculovirus. The recombinant baculovirus obtained was refined by a limiting dilution, and further infected to Sf9 insect cells at M.O.I=0.1 to obtain a seed virus. This seed virus was then infected to Tn5B-4 insect cells (Invitrogen) ($1.2×10^7$ cells per 150 $cm^2$ flask) at M.O.I=10–20, and incubated in a EX-CELL 400 serum-free medium (JRH Blosciences) (30 ml per 150 $cm^2$ flask) for 2 days at 27° C.

(3) Isolation and Purification of the Product

Figure 5:
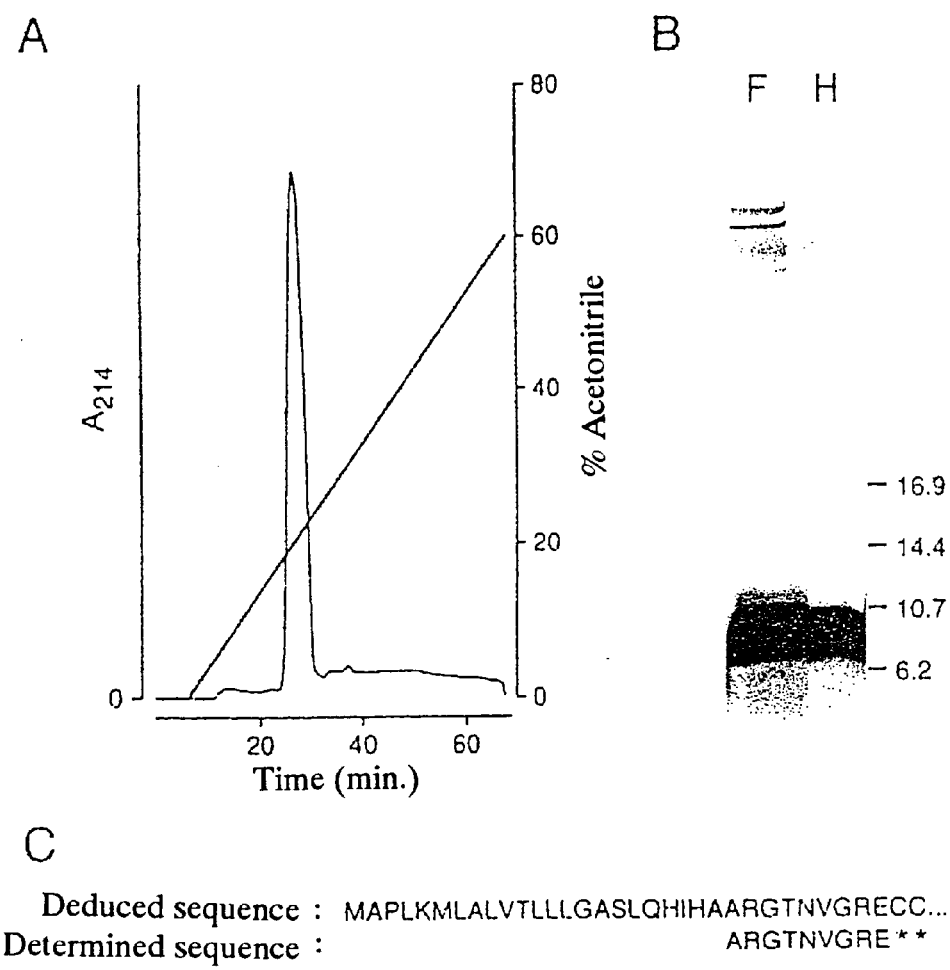
FIG. 5, panel A shows an elution pattern of purified final product of the human TARC produced in insect cells from a Cosmosil 5C4-300 column (Nacalai Tesque), and panel B is a photograph showing the result of SDS-PAGE.

The cultured supernatant was recovered, and filtered through a 0.22 µm filter membrane. To the resulting filtrate was added 1/10 volume of 500 mM MES (pH 6.5), and the mixture was applied to a 1 ml Resouce-S column (Pharmacia) equilibrated with Buffer A (50 mM MES (pH 6.5)/100 mM NaCl). This column to which the hTARC protein has been bound was washed with Buffer A, and then eluted with a salt concentration gradient of NaCl using Buffer A and Buffer B (50 mM MES (pH 6.5)/1.0 M NaCl). Fractions containing the hTARC protein were identified using SDS-PAGE and silver staining. The result of the SDS-PAGE is shown in FIG. 5B. In FIG. 5B, "F" indicates the result for a FPLC fraction (a purification step just before the final step), and "H" indicates that for a HPLC fraction.

To this fraction containing the hTARC protein was added TFA at a final concentration of 0.1%. The mixture was then applied to a Cosmosil 5C4-300 column (Nacalai Tesque) equilibrated with Buffer A (0.1% TFA), and eluted with an acetonitrile concentration gradient using Buffer A and Buffer B (0.1% TFA, 60% acetonitrile).

The elution pattern of the hTARC protein is shown in FIG. 5A. Fractions containing the hTARC protein were combined, and the acetonitrile was evaporated by drying in vacuo. The residue was then dialyzed against endotoxin-free PBS to obtain a purified final product. The concentration of protein was determined using BCA Kit (Pierce) and BSA as a control. The expression was good enough in amount, providing 300 μg of the purified hTARC protein from 300 ml of the cultured supernatant. The amount of contaminating endotoxin was below 4 pg/μg as assayed using a Limulus amoebocyte lysate assay (QCL-1000, Bio Whitaker). The N-terminal amino acid sequence of the purified hTARC protein was determined using an amino acid sequencer (Shimazu), and proved to be ARGTNVGRE (amino acids 24–32 of SEQ ID NO: 2). As shown in FIG. 5C, this amino acid sequence agreed with the N-terminal amino acid sequence of the mature secreted form of the protein consisting of 71 amino acids which can be generated by cleavage of the signal peptide predicted from the base sequence.

Figure 18:
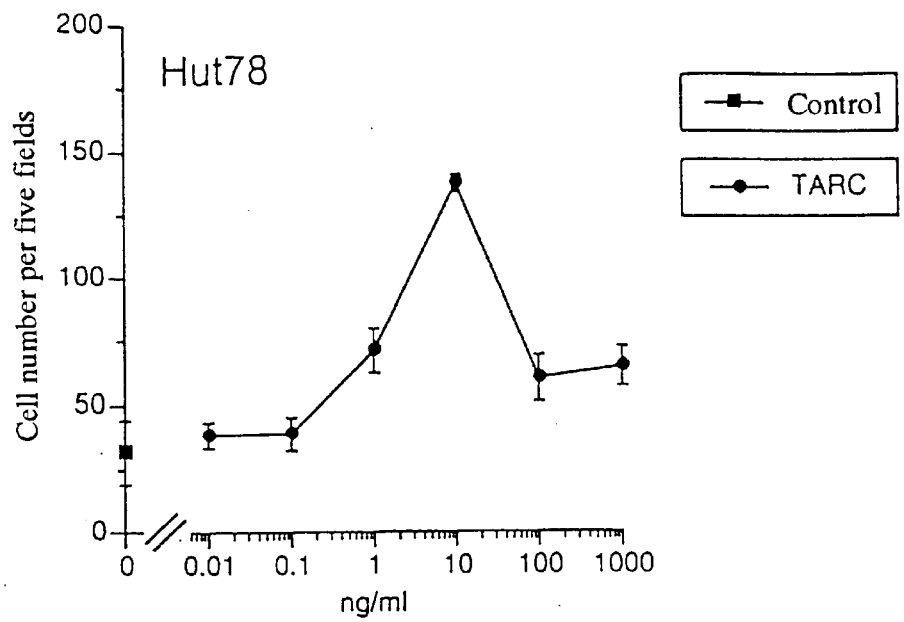
FIG. 18 is a graph showing the effect of concentration of TARC on the migration activity of HUT78 cells.
Figure 19:
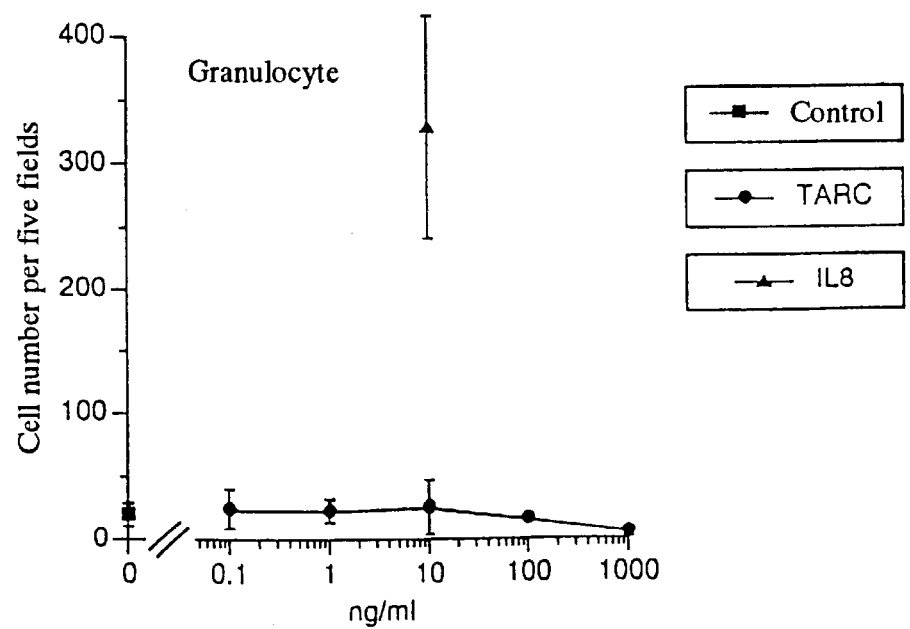
FIG. 19 is a graph showing the effect of concentration of TARC on the migration activity of granulocytes.
Figure 20:
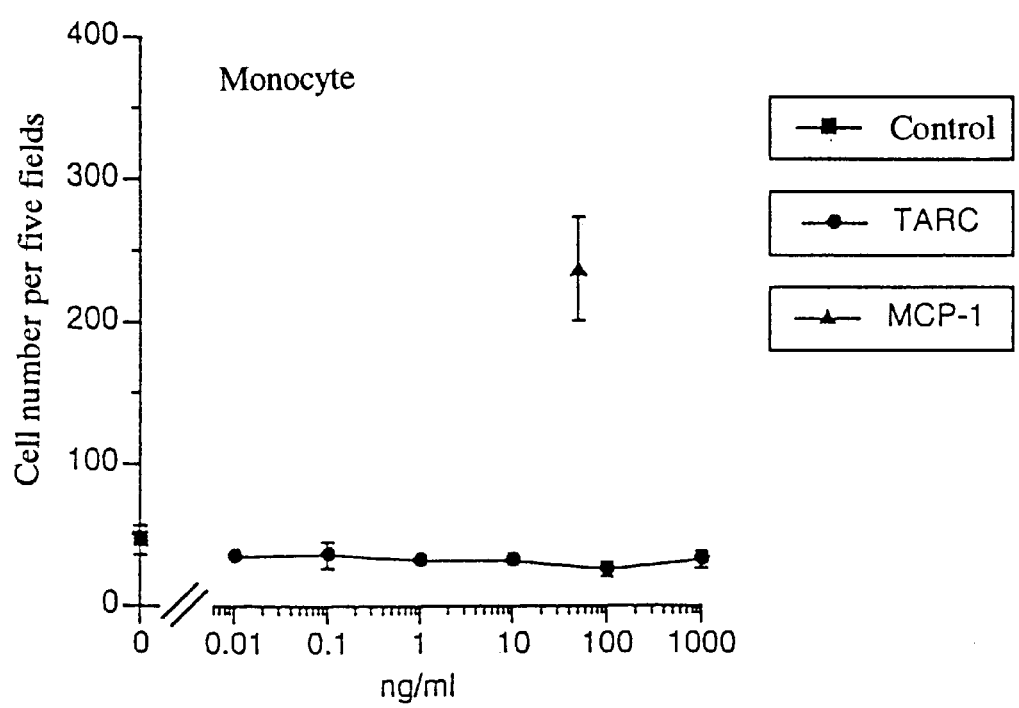
FIG. 20 is a graph showing the effect of concentration of TARC on the migration activity of monocytes.

The activity of the purified TARC protein was evaluated by cell migration tests. The results obtained using HUT78 cells, granulocytes and monocytes are shown in FIGS. 18, 19 and 20, respectively. These results indicate that the purified TARC protein shows a migration activity on T-cell line HUT78.

EXAMPLE 3

Expression of a Recombinant Human TARC in *E. coli*

(1) Construction of a Recombinant Vector pGEMEX-TARC for Expression of hTARC DNA in *E. coli*

Figure 6:
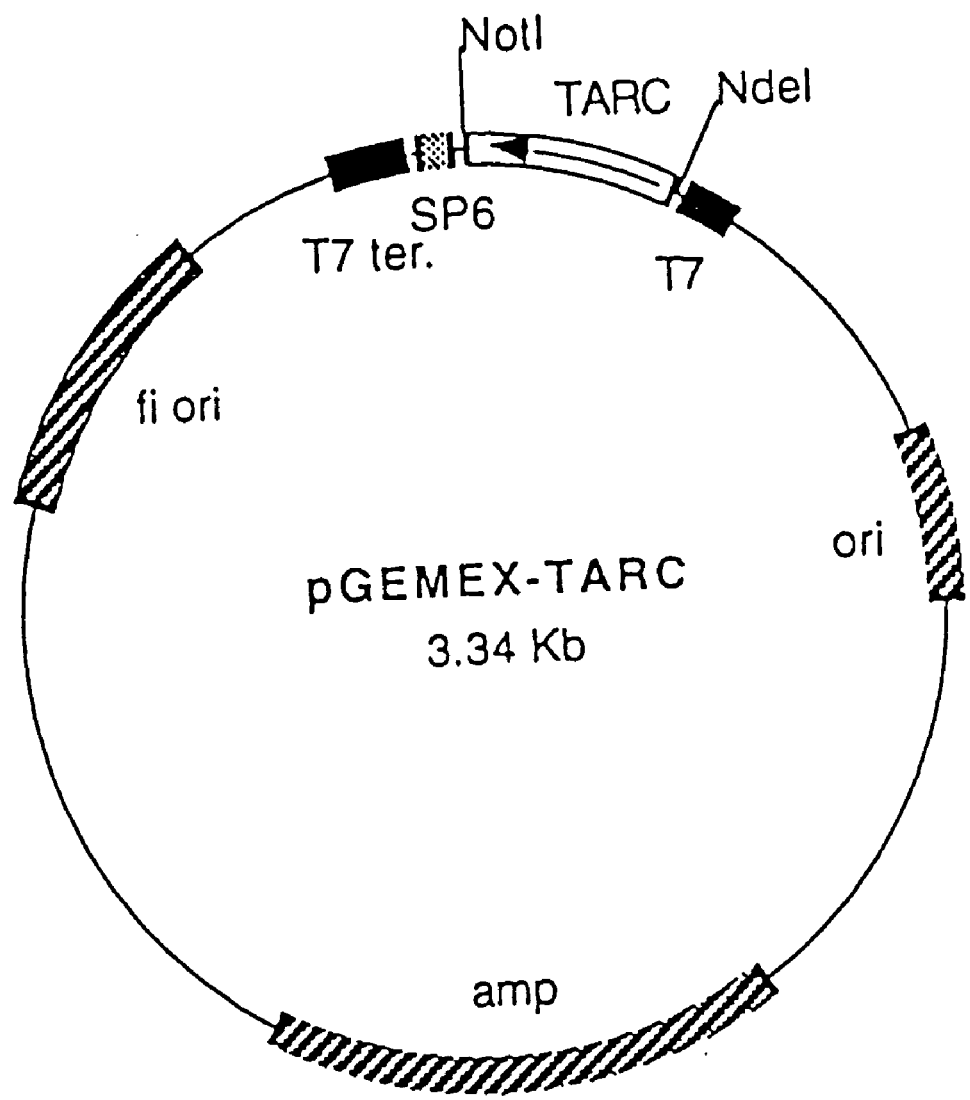
FIG. 6 is a gene map of an expression vector pGEMEX-TARC.

A 0.2 kb DNA fragment which has NdeI and NotI sites at its termini and which contains the sequence of the mature hTARC from its initiation codon to its translational termination codon was obtained by PCR using as a template clone D3A described in Example 1. The sequences of the two oligonucleotides used in the PCR are shown as SEQ ID NOS: 13 and 14. The PCR was conducted on a DNA Thermal Cycler (Perkin-Elmer) using AmpliTaq Kit purchased from Takara Shuzo. The reaction was carried out using the DNA of clone D3A as a template in a reaction buffer (10 mM Tris-HCl, pH 8.3, 50 mM KCl, 1.5 mM $MgCl_2$, 0.1% gelatin, 200 μM dNTPs (dATP, dGTP, dCTP, dTTP), 400 μM primers, and 100 U/ml AmpliTaq DNA polymerase). The reaction was performed as follows; pretreatment at 94° C. for 3 minutes; 15 cycles of 45 seconds at 94° C., 45 seconds at 55° C., and 1 minute at 72° C.; and a final treatment for 3 minutes at 72° C. The reaction product was then digested simultaneously with NdeI and NotI, and inserted between the NdeI site and the NotI site in pGEMEX1 (Promega) to obtain an expression vector pGEMEX-TARC. The gene map of this vector is shown in FIG. 6.

(2) Culture of Transformants

The mature hTARC protein having a methionine residue at the amino terminus was expressed from *E. coli* strain BL21 transformed with the expression vector pGEMEX-TARC. Culture of *E. coli* strain BL21 was carried out for 3 hours at 37° C. in a LB medium containing 1 mM IPTG.

(3) Isolation and Purification of the Product

Figure 7:
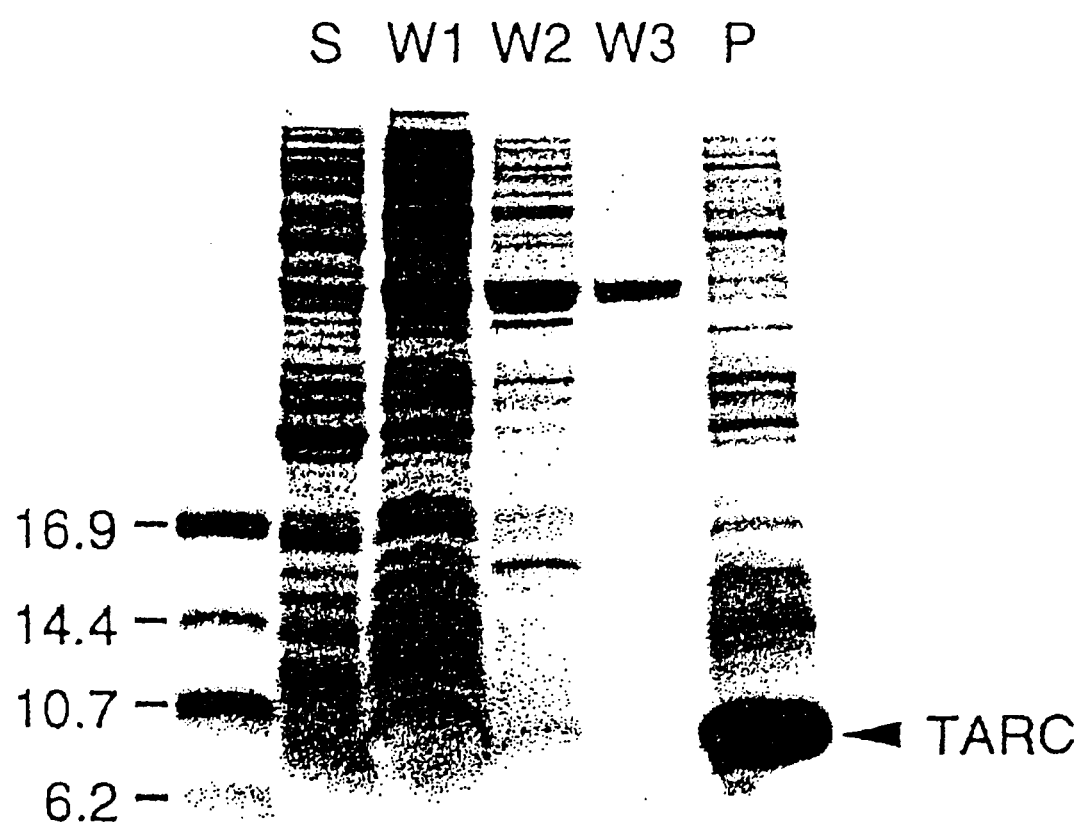
FIG. 7 is a photograph showing the results of SDS-PAGE at various stages in the purification of human TARC expressed in *Escherichia coli*.

The *E. coli* cells were suspended in a Tris buffer (50 mM Tris-HCl, pH 8.0, 1 mM EDTA, 1 mM 2-ME, 50 mM NaCl, 0.2 mM PMSF), and subjected to 5 cycles of freeze and thaw. To the mixture were then added DNase I and $MgCl_2$ at final concentrations of 10 μg/ml and 10 mM, respectively, and the mixture allowed to stand for 10 minutes at room temperature. After centrifuging for 15 minutes at 4° C. and at 10,000 rpm, the precipitated hTARC protein was washed three times with a washing solution (0.5% Triton X-100, 10 mM EDTA) to obtain a partially purified recombinant hTARC protein. The results of SDS-PAGE demonstrating the purification of hTARC are shown in FIG. 7. In FIG. 7, "S" indicates the result for the supernatant obtained by the centrifugation, "W1", "W2", and "W3" indicate the results for the substances eluted in the first, second, and third washings, respectively, of the precipitate obtained by the centrifugation, and "P" indicates the result for the washed precipitate containing the hTARC.

EXAMPLE 4

Isolation of a DNA Encoding Mouse TARC

I. Cloning of Mouse Genomic TARC DNA

To obtain a mouse TARC genomic DNA, the SmaI-PstI fragment of the human TARC cDNA clone D3A described in Example 1 was labeled with $^{32}P$ using Multiprime DNA Labeling System (Amersham Japan), and used as a probe to screen a genomic DNA library derived from Balb/c mouse (Clontech) by plaque hybridization. The plaque hybridization was conducted according to the procedure described in a literature (Sambrook et al., Molecular Cloning: A Laboratory Manual, second edition, Cold Spring Harbor Laboratory, New York (1989)).

The phage solution of the genomic DNA library derived from Balb/c mouse and *E. coli* LE392 were plated onto a LB-plate (10 g tryptone, 5 g yeast extract, 10 g NaCl, 15 g agar per 1 L distilled water), and incubated overnight at 30° C. Plaques of phage generated on the plate were transferred onto a nylon membrane (Hybond-N$^+$, Amersham Japan), and subjected to SDS treatment (10% SDS), alkaline-denaturation (0.5 N NaOH, 1.5 M NaCl), and washing (2×SSC). This membrane was then subjected to hybridization using as a probe the SmaI-PstI fragment of the hTARC cDNA clone D3A labeled with $^{32}P$. The hybridization was conducted overnight at 42° C. in a hybridization solution consisting of 5×SSPE (1×SSPE consists of 0.18 M NaCl, 0.01 M sodium phosphate, pH 7.5, 1 mM EDTA), 30% formamide, 2% SDS, 10×Denhardt's solution, 100 μg/ml salmon sperm DNA. The membrane was washed with 2×SSC, 0.1% SDS for 10 minutes at room temperature, and twice with 2×SSC, 0.1% SDS for 30 minutes at 60° C. Then, a X-ray film (Kodak) was exposed to the membrane, and developed for identification of plaques which react with the probe. Finally, 8 genomic DNA clones were obtained.

The sequence of the 4234 bases in one of the resultant genomic DNA clones (clone #3) was determined by the Sanger method using A.L.F II Automated Sequencer and Autoread Sequence Kit manufactured by Pharmacia. A high homology to the human TAJKC was found in three regions. These three regions were presumed to be exons. Conjunction of these three regions generated a base sequence which contains an open reading frame consisting of 93 amino acids, and which is highly homologous (64.4%) to that of the human TARC. Accordingly, the resultant DNA was identified as a genomic DNA for a mouse TARC.

II. Cloning of a Mouse TARC cDNA (1) Preparation of cDNA Library Derived From PHA-stimulated Balb/c Mouse Spleen Cell A cDNA library derived from PHA-stimulated Balb/c mouse spleen cell was prepared in the following manner according to the descriptions in a literature (Sambrook et al., Molecular Cloning: A Laboratory Manual, second edition, Cold Spring Harbor Laboratory, New York (1989)) using a cDNA synthesis system and a cDNA cloning system manufactured by GIBCO-BRL.

Poly(A)$^+$RNAs were first extracted from Balb/c mouse spleen cells stimulated with PHA using QuickPrep Micro mRNA Purification Kit (Pharmacia). Balb/c mouse spleen cells (2×10$^7$) stimulated with PHA for 24 hours were lysed with cell lysis solution appended to the kit. Oligo-dT resins were added and mixed for 3 minutes to allow to bind to poly(A)+RNAs, followed by centrifugation for 1 minute at 12,000 rpm in a TOMY centrifuge MRX-150 (TOMY Seiko). The precipitates were washed with a high salt washing solution (3×), and a low salt washing solution (5×), and eluted with an eluent. To the eluate were added 0.1 volume of 3M sodium acetate and 2 volumes of ethanol, and the mixture cooled for 1 hour at −80° C., and centrifuged for 5 minutes at 12,000 rpm in a TOMY centrifuge MRX-150 (TOMY Seiko) to precipitate the poly(A)+RNAs. The precipitates were then dissolved in sterile distilled water. The amount of recovered poly(A)+RNAs was calculated from the absorbance at 260 nm. Ten µg of poly(A)+RNAs was obtained from the PHA-stimulated Balb/c mouse spleen cells.

cDNAs were then synthesized using the purified poly(A)+ RNAs as templates in the following manners. Single stranded DNAs were first synthesized using a reverse transcriptase SUPER SCRIPT II RT (GIBCO-BRL) by reacting 4 µg of poly(A)+RNAs as templates for 1 hour at 37° C. in a reaction buffer (50 mM Tris-HCl, pH 8.3, 75 mM KCl, 3 mM $MgCl_2$, 10 mM DTT, 500 µM dNTPs (dATP, dGTP, dCTP, dTTP), 50 µg/ml NotI primer-adapter (GIBCO-BRL) and 20,000 U/ml reverse transcriptase SUPER SCRIPT II RT). The sequence of the NotI primer-adapter is shown as SEQ ID NO: 3. These single-stranded DNAs were reacted as templates for 2 hours at 16° C. in a reaction buffer (25 mM Tris-HCl, pH 7.5, 100 mM KCl, 5 mM $MgCl_2$, 10 mM $(NH_4)_2SO_2$, 1.2 mM DTT, 0.15 mM β-NAD+, 250 µM dNTPs (dATP, dGTP, dCTP, dTTP), 65 U/ml DNA ligase, 250 U/ml DNA polymerase I, and 13 U/ml RNase H) to synthesize cDNAs. After the addition of T4 DNA polymerase at a final concentration of 65 U/ml, the reaction was continued for 5 minutes at 16° C. to obtain double-stranded DNAs. The resultant double-stranded DNAs were reacted for 16 hours at 16° C. in a reaction buffer (50 mM Tris-HCl, pH 7.6, 10 mM $MgCl_2$, 1 mM DTT, 1 mM ATP, 5% PEG 8000, 200 µg/ml EcoRI adapter (Pharmacia), and 100 U/ml T4 DNA ligase) to ligate them to the EcoRI adapter. The EcoRI adapter is a double-stranded one in which the DNAs shown as SEQ ID NOS: 15 and 16 have annealed. The resultant cDNAs thus completed were inserted between the NotI and EcoRI sites in λExCell vectors to obtain a cDNA library.

(2) Preparation of a Probe

Using as a template the cDNA library derived from the PHA-stimulated Balb/c mouse spleen cell which was prepared in the above (1), a polymerase chain reaction (PCR) was conducted in a reaction buffer (10 mM Tris-HCl, pH 8.3, 50 mM KCl, 1.5 mM $MgCl_2$, 0.1% gelatin, 200 µM dNTPs (dATP, dGTP, dCTP, dTTP), 400 nM mG98 exon upper primer, 400 nM mG98 exon lower primer, and 100 U/ml AmpliTaq DNA polymerase I). The mG98 exon upper primer and the mG98 exon lower primer were designed on the basis of the mouse genomic DNA obtained in the above (I). The sequences of these primers are shown as SEQ ID NOS: 17 and 18. The mG98 exon upper primer and the mG98 exon lower primer were synthesized on a DNA synthesizer (Cyclone Plus DNA Synthesizer, Miligen/Biosearch). In the synthesis, β-linked beta-cyanoethylphosphoamidite reagents from Miligen/Biosearch were used. After the synthesis was completed, the synthesized oligonucleotide was eluted from the synthesis column with 2 ml of aqueous ammonia (28%, Nacalai Tesque), and treated for 5 hours at 60° C. to detach the protective groups. The deprotected oligonucleotide was then added to 10 volumes of butanol, and centrifuged for 10 minutes at 3,000 rpm in a TOMY centrifuge (TOMY Seiko) to precipitate and recover the product. The recovered oligonucleotide was dissolved in sterile distilled water, and the amount thereof was determined by measuring the absorbance at 260 nm. The PCR was carried out on a DNA Thermal Cycler (Perkin-Elmer) using AmpliTaq Kit purchased from Takara Shuzo. The reaction was conducted as follows: a pretreatment for 3 minutes at 94° C.; 40 cycles of 45 seconds at 94° C., 45 seconds at 60° C., and 1 minute at 72° C.; and a final treatment for 3 minutes at 72° C. The 321 bp DNA fragment so obtained was used as a probe for obtaining a full-length cDNA for mouse TARC.

(3) Cloning of a Full-length cDNA for Mouse TARC

In order to obtain a full-length cDNA for mouse TARC, the 321 bp DNA fragment obtained in the above (2) was labeled with $^{32}P$ using Multiprime DNA Labeling System (Amersham Japan), and used as a probe to screen the cDNA library derived from PHA-stimulated Balb/c mouse spleen cell prepared in the above (1) by a plaque hybridization method. The plaque hybridization was conducted in the following manner according to a method described in a literature (J. Sambrook et al., Molecular Cloning: A Laboratory Manual, second edition, Cold Spring Harbor Laboratory, New York (1989)).

The phage solution of the cDNA library derived from PHA-stimulated Balb/c mouse spleen cell and E. coli LE392 were plated onto a LB-plate (10 g tryptone, 5 g yeast extract, 10 g NaCl, 15 g agar per 1 L distilled water), and incubated overnight at 30° C. Plaques of phage generated on the plate were transferred onto a nylon membrane (Hybond-N+, Amersham Japan), and subjected to SDS treatment (10% SDS), alkaline-denaturation (0.5 N NaOH, 1.5 M NaCl), and washing (2×SSC). The membrane was then subjected to a hybridization procedure using as a probe the 321 bp DNA fragment labeled with $^{32}P$. The hybridization was conducted overnight at 42° C. in a hybridization solution consisting of 5×SSPE (1×SSPE consists of 0.18 M NaCl, 0.01 M sodium phosphate, pH 7.5, 1 mM EDTA), 50% formamide, 2% SDS, 10×Denhardt's solution and 100 µg/ml salmon sperm DNA. The membrane was washed with 2×SSC, 0.1% SDS for 10 minutes at room temperature, and twice with 2×SSC, 0.1% SDS for 30 minutes at 60° C. Then, a X-ray film (Kodak) was exposed to the membrane, and developed for identification of plaques which react with the probe. Finally, one cDNA clone (clone #1) was obtained. The cDNA inserted in this clone #1 was sequenced by the Sanger method using A.L.F II Automated Sequencer and Autoread Sequence kit manufactured by Pharmacia, and further subjected to various examinations described below. In result, it was confirmed that said cDNA encoded an objective novel type CC chemokine-like protein (mTARC).

II. Determination of the Structure of Mouse TARC (1) Analysis of the Base Sequence of the mTARC cDNA and the Amino Acid Sequence Encoded Thereby The base sequence of the mouse cDNA clone #1 obtained in the above II. (3) and the amino acid sequence of the open reading frame which does not internally contain any translational termination codon are shown in FIG. 8.

As shown in FIG. 8, it was revealed that the gene inserted in clone #1 contains an open reading frame consisting of 93 amino acids, and that, at the N-terminus, it has a highly hydrophobic amino acid sequence characteristic of signal peptides. The calculated molecuar weight of the 93 a.a. protein is 10,466. The putative cleavage site of the signal peptide is between Ala-23 and Ala-24 according to a calculation, and indicated in FIG. 8 by a vertical bar. Two contiguous cysteines characteristic of type CC chemokines are shown at 9 amino acids downstream from this cleavage site.

In addition, the putative mature protein consisting of 70 amino acids generated by cleavage of the signal peptide is presumed to be a secreted protein. The molecular weight of the putative mature secreted protein of 70 amino acids is calculated to be 7,916, and the calculated isoelectric point is 10.2.

(2) Similarity to Human TARC

The amino acid sequence of mouse TARC protein of mature secreted form proved to be 65% homologous to that of human TARC. Similarly, the base sequence of the open reading frame of the mouse TARC proved to be 74% homologous to that of human TARC. It was demonstrated that the four cysteines conserved in all of the type CC chemokines are also conserved in the mouse TARC. The above results suggest that the mouse TARC is a mouse homolog of the human TARC gene or protein.

EXAMPLE 5

Figure 9:
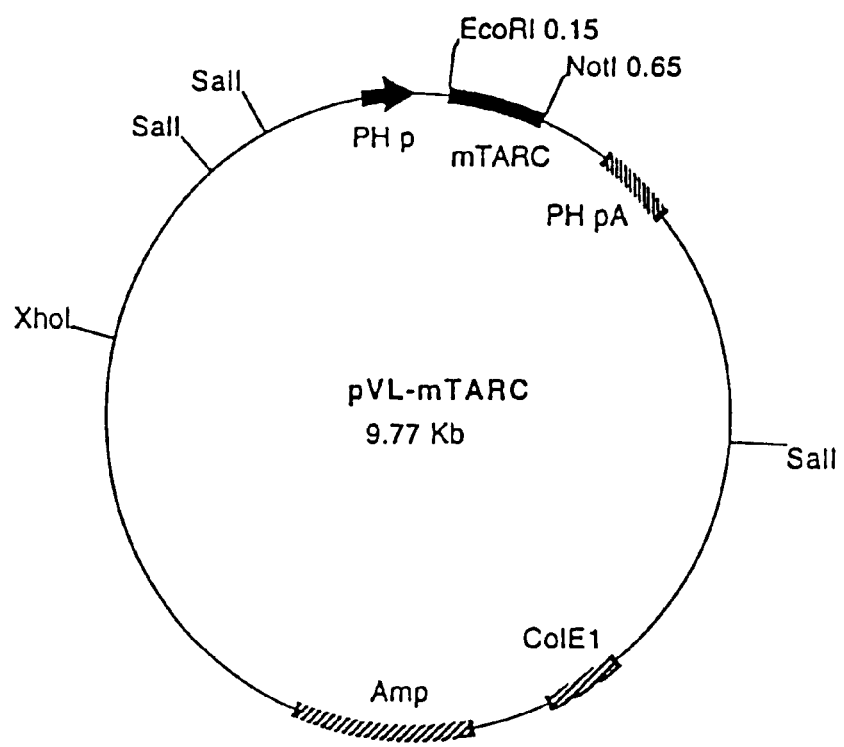
FIG. 9 is a gene map of a recombinant vector pVL-mTARC.

Expression of Recombinant Mouse TARC in Silkworm Cell (1) Construction of a Recombinant Vector pVL-mTARC for Expression of the mTARC DNA in Silkworm Cell A 0.5 kb DNA fragment which has EcoRI and NotI sites at its both termini and which contains the mTARC sequence spanning from the translational initiation codon to its translational termination codon was obtained by simultaneously digesting clone #1 with EcoRI and NotI. This DNA fragment was inserted between the EcoRI and the NotI sites in pVL1393 (Invitrogen), which is used for the preparation of a recombinant baculovirus, to obtain a recombinant vector pVL-mTARC. The gene map of this recombinant vector is shown in FIG. 9.

(2) Culture of Transformant

The recombinant vector pVL-mTARC and a linear DNA of AcNPV having a lethal deletion were then concurrently introduced into Sf9 insect cells to obtain a recombinant baculovirus. The resultant recombinant baculovirus was refined by limiting dilution, and infected to Sf9 insect cells at M.O.I=0.1 to obtain a seed virus. The seed virus was then infected to Tn5B-4 insect cells (Invitrogenj (1.2×10$^7$ cells per 150 cm$^2$ flask) at M.O.I=10–20. The infected cells were incubated in a EX-CELL 400 serum-free medium (JRH BIosciences) (30 ml per 150 cm$^2$ flask) for 2 days at 27° C.

(3) Isolation and Purification of the Product

Figure 10:
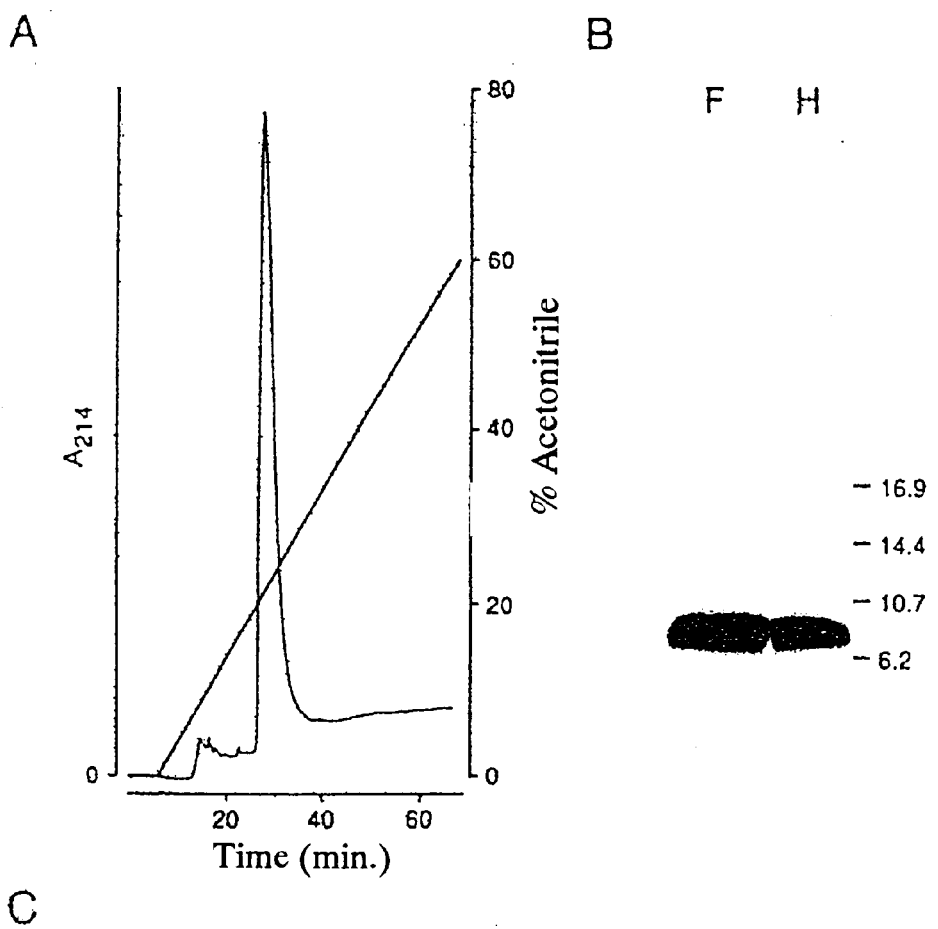
FIG. 10, panel A shows an elution pattern of a purified final product of mouse TARC produced in insect cells from a Cosmosil 5C4-300 column (Nacalai Tesque), and panel B is a photograph which shows a result of SDS-PAGE.

The cultured supernatant was recovered, and filtered through a 0.22 μm filter membrane. To the resulting filtrate was added 1/10 volume of 500 mM MES (pH 6.5), and the mixture applied to a 1 ml Resouce-S column (Pharmacia) equilibrated with Buffer A (50 mM MES (pH 6.5)/100 mM NaCl). This column to which the mTARC protein has been bound was washed with Buffer A, and eluted with a gradient of NaCl using Buffer A and Buffer B (50 mM MES (pH 6.5)/1.0 M NaCl). Fractions containing the mouse TARC protein were identified using SDS-PAGE and silver staining. The result of the SDS-PAGE is shown in FIG. 10. In FIG. 10B, "F" indicates the result for a FPLC fraction (a purification step just before the final step), and "H" indicates that for a HPLC fraction.

To the fraction containing the mouse TARC protein was added TFA at a final concentration of 0.1%. The mixture was then applied to a Cosmosil 5C4-300 column (Nacalai Tesque) equilibrated with Buffer A (0.1% TFA), and eluted with an acetonitrile concentration gradient using Buffer A and Buffer B (0.1% TFA, 60% acetonitrile). The elution pattern of the mouse TARC protein is shown in FIG. 10A. Fractions containing the mouse TARC protein were combined and dried in vacuo to remove acetonitrile. The residue was then dialyzed against endotoxin-free PBS to obtain a purified final product. The concentration of protein was determined using BCA Kit (Pierce) and BSA as a control. From 300 ml of the cultured supernatant, 168 μg of the purified mouse TARC protein was obtained. The amount of contaminating endotoxin was below 2 pg/μg as assayed using a Limulus amoebocyte lysate assay (QCL-1000, Bio Whitaker). The N-terminal amino acid sequence of the purified mTARC protein was determined using an amino acid sequencer (Shimazu), and proved to be ARATNVGRE**LDYF (SEQ ID NO: 35). As shown in FIG. 10C, the amino acid sequence agreed with the N-terminal amino acid sequence of the protein of mature secreted form consisting of 70 amino acids, which may have been generated by cleavage of the signal peptide predicted from the base sequence.

EXAMPLE 6

Leukocyte Infiltration Induced by Mouse TARC

The infiltration of leukocytes by mouse TARC obtained in Example 5 was studied in mouse which received the TARC intradermally.

The purified mouse TARC protein was intradermally administered into the dorsa of Balb/c mice, and the presence of leukocyte infiltration was examined to confirm the chemokine-like activity of the mTARC. In particular, 50 ng of the purified mouse TARC was dissolved in endotoxin-free PBS to 50 μl, and intradermally administered into the dorsa of Balb/c mice. As a negative control, 50 μl of endotoxin-free PBS was used. After 4 and 24 hours of the administration, the mouse was sacrificed by dislocation of the jugular vertebra, and the skin at the administration site was excised and fixed with 10% formaldehyde. The fixed skin was then embedded in paraffin, sectioned in 5 μm thickness with a microtome, and stained with hematoxylin-eosin. The results are shown in FIG. 11 for the mTARC, and in FIG. 12 for the control. In FIGS. 11 and 12, panel A and panel B are microphotographs after 24 hours of the administration at magnifying powers of 100 and 400, respectively. As shown in FIGS. 11A and B, infiltration of lymphocytes and monocytes was observed after 24 hours of the TARC administration in the subcutis to which the mouse TARC has been administrated. In contrast, as shown in FIG. 12A and B, PBS alone did not cause such a change.

EXAMPLE 7

Detection of Cells Expressing TARC Receptor

Cells expressing TARC receptor were detected using human TARC labeled with iodine. The human TARC protein expressed and purified from insect cells as described in Example 2 was labeled with $^{125}$I using $^{125}$I-labeled Bolton-Hunter reagent (Amersham Japan). The $^{125}$I-labeled hTARC was purified by gel-filtration using Bio-Gel P6 (BioRad), and the specific activity was determined to be 81.6 μCi/μg. The labeled hTARC was used in the binding tests on cells of various types.

Cells (1×10$^6$–8×10$^6$) to be tested were washed with a binding buffer (PRMI-1640, 20 mM HEPES (pH 7.4), 1% BSA, 0.02% NaN$_3$), and suspended in 100 μl of the binding buffer. To the cell suspension was added 100 μl of the binding buffer to which the $^{125}$I-labeled hTARC has been added at a final concentration of 0.66 nM, and the binding reaction was allowed to proceed for 1 hour at room temperature. After the completion of the reaction, the mixture was then overlaid onto 300 μl of a dibutyl phthalate: olive oil (4:1) mixture, and centrifuged to separate the $^{125}$I-labeled TARC bound to the cells from the unbound $^{125}$I-labeled TARC. The radioactivity of the $^{125}$I-labeled TARC bound to the cells was then determined using a gamma-counter. The specific binding of hTARC to the cells was calculated by subtracting the value for the $^{125}$I-labeled TARC nonspecifically bound in the presence of 200 nM unlabeled hTARC from the value for the $^{125}$I-labeled TARC bound in the absence of unlabeled TARC. The specific bindings of the $^{125}$I-labeled TARC per $10^6$ cells of various types are shown in FIG. 13.

Figure 13:
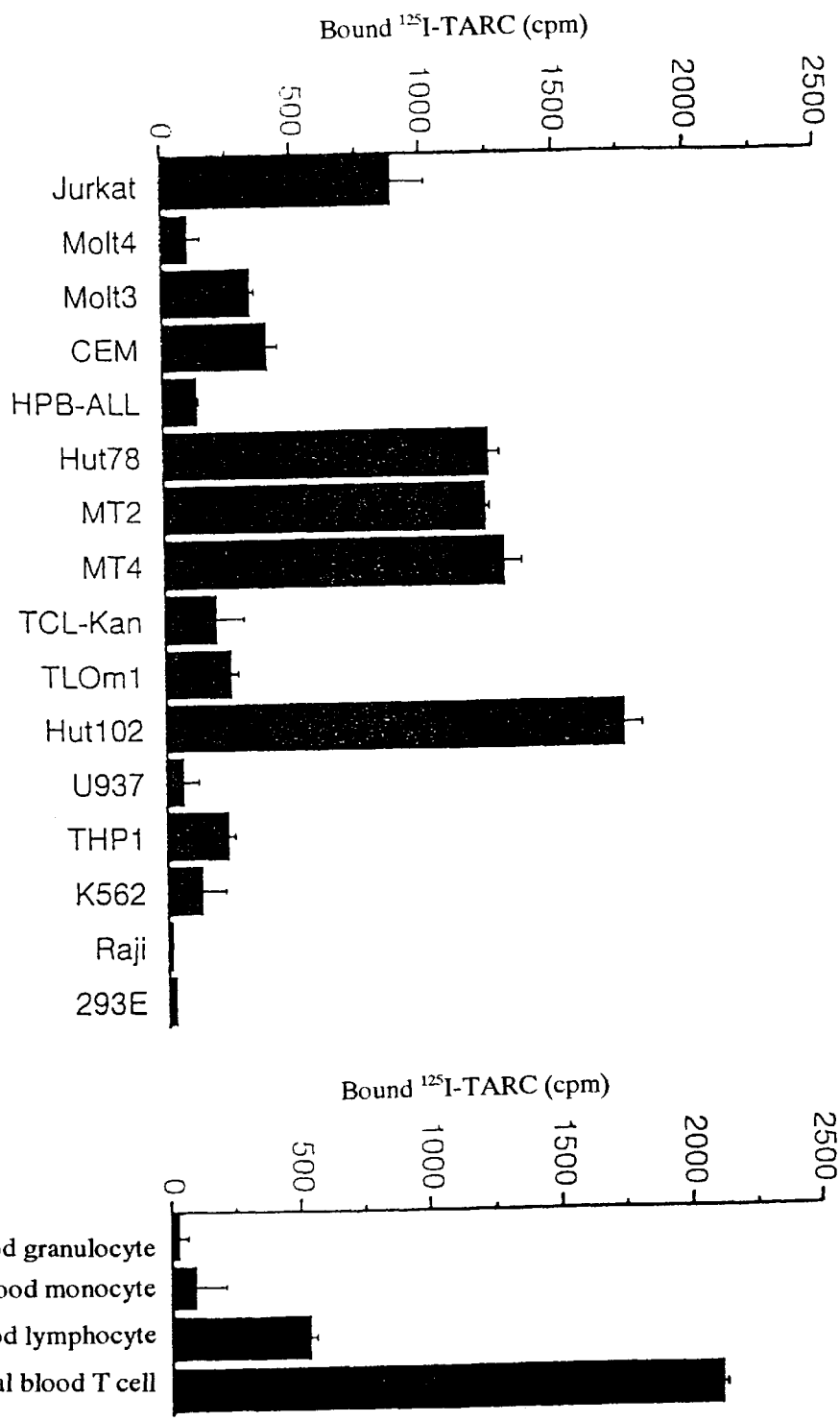
FIG. 13 is a bar graph showing the specific binding of $^{125}$I-labeled TARC to various types of cell.

As apparent from FIG. 13, a considerable specific binding can be observed in certain T-cell lines (Jurkat, Molt3, CEM, Hut78, MT2, MT4, Hut102), peripheral blood lymphocytes, and activated peripheral blood T-cells. However, specific binding is hardly observed in the rest of T-cell lines (Molt4, HPB-ALL, TCL-Kan, TLOml), monocyte lines (U937, THP1), an erythroblast cell line (K562), and peripheral blood monocytes. Almost no specific binding is observed in a B-cell line (Raji), a cell line derived from fetal kidney (293E), and peripheral blood granulocytes.

The above results indicate that receptors for TARC are highly expressed on certain kinds of T-cells.

EXAMPLE 8

Binding Property Between TARC and the Receptor

TARC receptor was analyzed in more detail using a T-cell line Jurkat.

(1) Binding Constant and the Number of Receptor

To determine the binding constant and the number of receptor, conditions under which the binding reaches equilibrium were examined. In result, the specific binding of $^{125}$I-labeled human TARC to Jurkat cells proved to reach equilibrium in 1 hour at 15° C. The change in the specific binding of TARC to 4×10$^6$ Jurkat cells was tested using $^{125}$I-labeled TARC of different concentration. The amount of the specific binding was calculated by subtracting the value for the $^{125}$I-labeled TARC nonspecifically bound in the presence of 1 μM unlabeled TARC from the value for the $^{125}$I-labeled TARC bound in the absence of unlabeled TARC. The result is shown in FIG. 14A. The specific binding of the $^{125}$I-labeled TARC to Jurkat cells gave a saturation curve. FIG. 14B shows the result of the Scatchard analysis of the measurement. Only a single kind of specific binding sites for the $^{125}$I-labeled TARC was found on Jurkat cells, and the binding constant and the number of the binding sites per cell were calculated to be 2.1 nM and 603, respectively.

Figure 15:
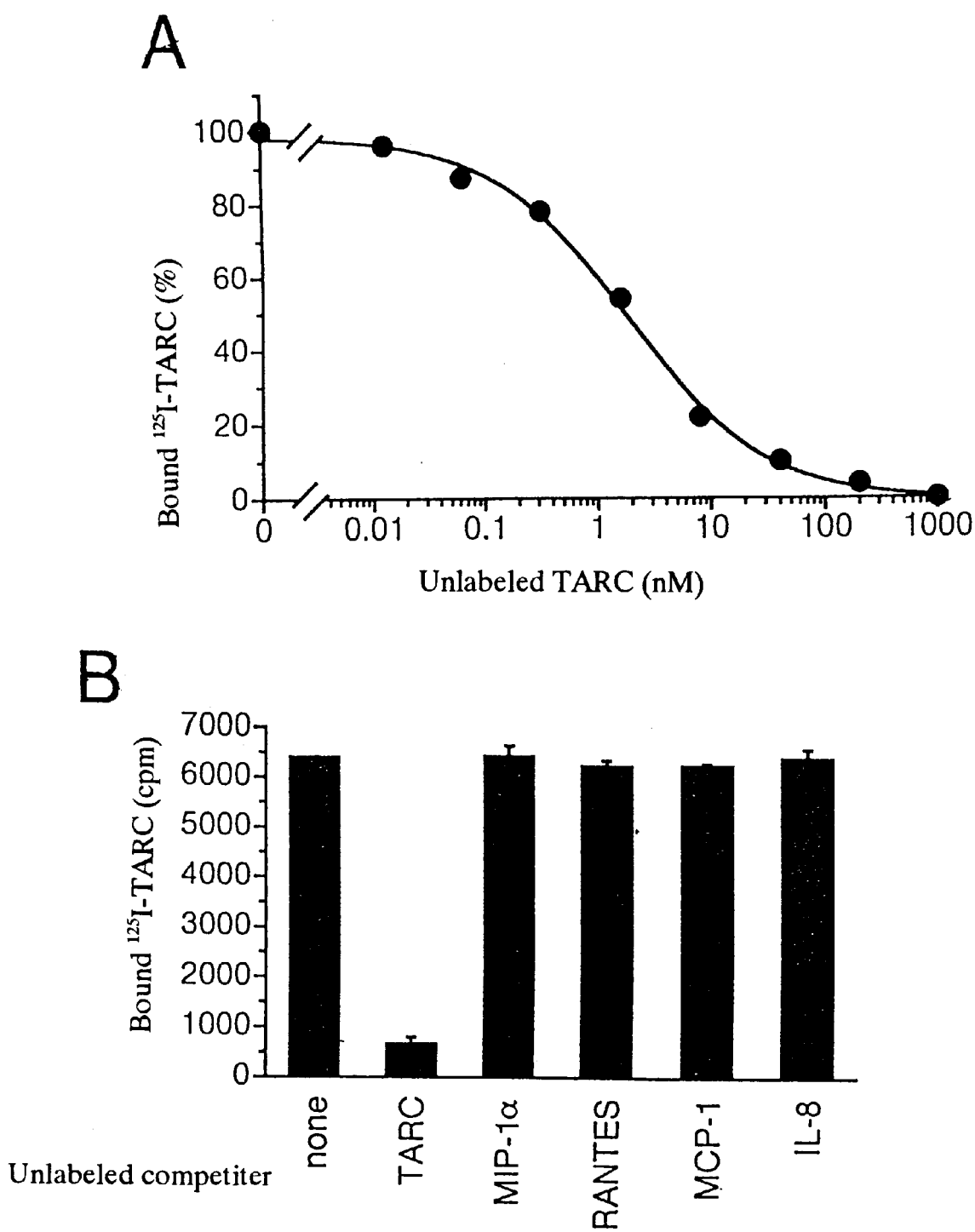
FIG. 15, panel A is a graph showing the specific binding of $^{125}$I-labeled TARC to Jurkat cells, which was obtained at a fixed concentration of $^{125}$I-labeled TARC while increasing the concentration of unlabeled TARC, and panel B is a graph showing the binding of $^{125}$I-labeled TARC to Jurkat cells, which was obtained at a fixed concentration of $^{125}$I-labeled TARC in the absence of unlabeled chemokines, or in the presence of 200 nM of TARC or other chemokines.

The change in the specific binding of TARC to 4×10$^6$ Jurkat cells was then evaluated by changing the concentration of unlabeled TARC at a fixed concentration (2 nM) of the $^{125}$I-labeled TARC. The amount of the specific binding was calculated by subtracting the value for the $^{125}$I-labeled TARC nonspecifically bound in the presence of 1 μM unlabeled TARC from the values for the $^{125}$I-labeled TARC bound in the presence of various concentrations of unlabeled TARC, and expressed in percentage considering the amount of the specific binding in the absence of unlabeled TARC as 100%. The result is shown in FIG. 15A. Based on the Scatchard analysis, a single kind of specific binding sites for the $^{125}$I-labeled TARC was found on Jurkat cell, and the binding constant and the number of the binding site were calculated to be 2.1 nM and 948, respectively.

(2) Inhibition of Binding by Other Type CC Chemokines

The competition between TARC and other type CC chemokines in the biding to Jurkat cells was evaluated as follows. The binding reaction to 4×10$^6$ Jurkat cells was conducted for 1 hour at room temperature at a fixed concentration (0.66 nM) of the $^{125}$I-labeled hTARC in the absence of unlabeled chemokines or in the presence of 200 nM IL-8, RANTES, MCP-1, MIP-1α (all from PeproTech), or TARC. The result is shown in FIG. 15B. The binding of the $^{125}$I-labeled TARC was competitively inhibited only by unlabeled TARC, but not by other chemokines, indicating that the receptor for TARC on Jurkat cell is distinct from and independent of those for other chemokines.

(3) Binding Activity to Receptors on Erythrocyte

Figure 16:
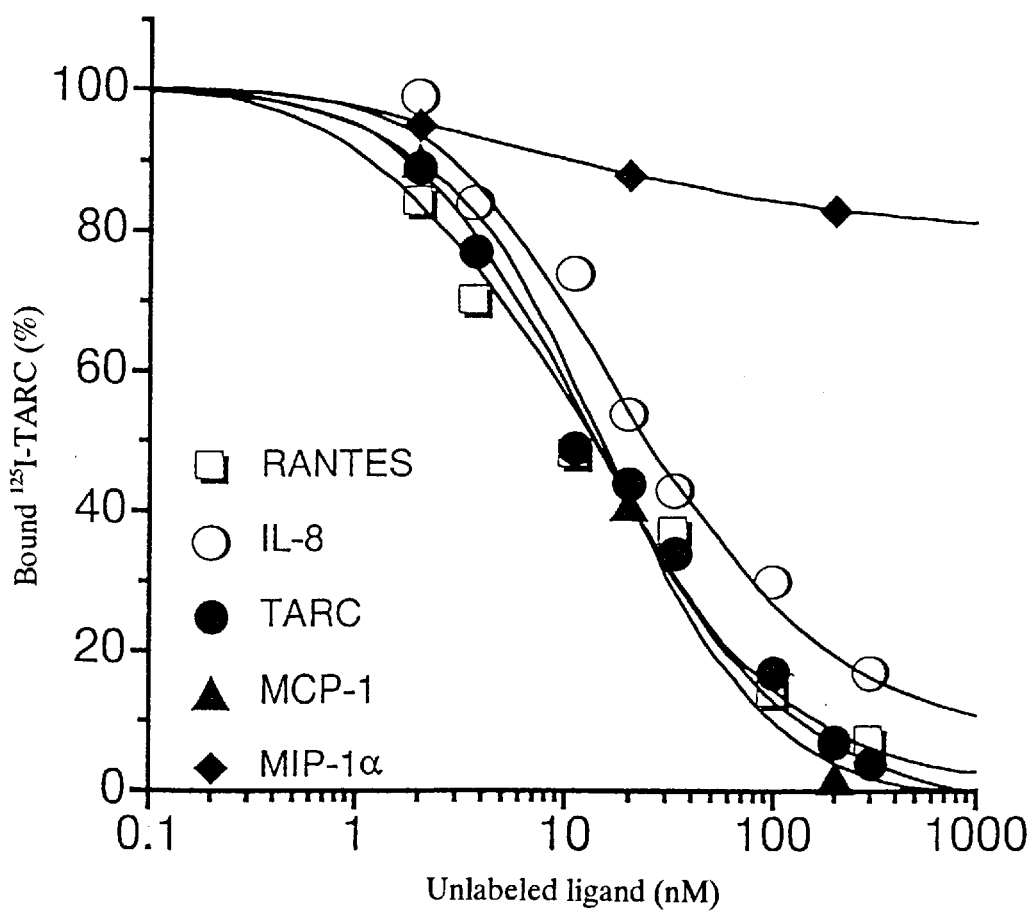
FIG. 16 is a graph showing the change in the amount of specific binding of $^{125}$I-labeled TARC to erythrocytes, which was obtained at a fixed concentration of $^{125}$I-labeled TARC and increasing concentrations of unlabeled TARC or other chemokines.
Figure 17:
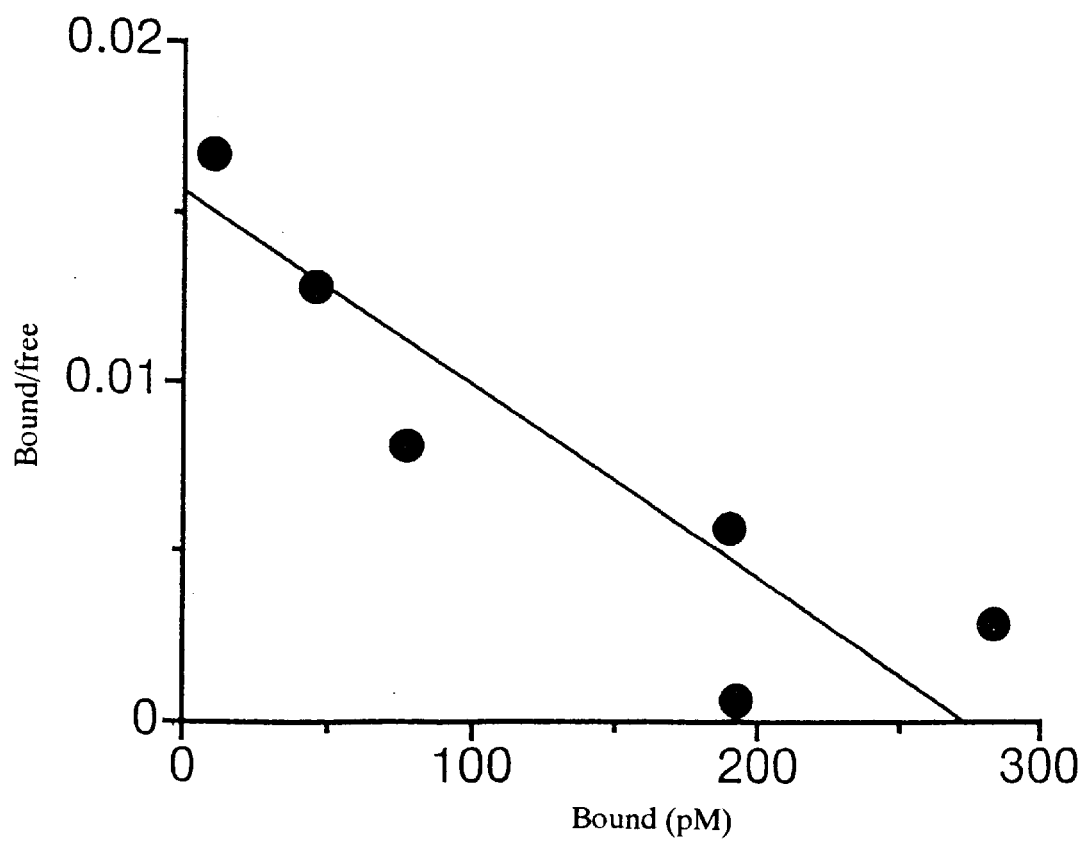
FIG. 17 is a Scatchard plot of the results shown in FIG. 16.

It has been known that erythrocyte expresses a Duffy antigen/receptor for chemokine (DARC) to which various chemokines can be bound. The change in amount of the specific binding to 10$^8$ erythrocytes was studied at a fixed concentration (0.66 nM) of the $^{125}$I-labeled TARC in the presence of various concentrations of unlabeled TARC or other chemokines (IL-8, RANTES, MCP-1, MIP-1α). The amount of the specific binding was calculated by subtracting the value for the $^{125}$I-labeled TARC nonspecifically bound in the presence of 1 μM unlabeled TARC from the values for the $^{125}$I-labeled TARC bound in the presence of various concentrations of unlabeled chemokines, and expressed in percentage considering the amount of the specific binding in the absence of unlabeled TARC as 100%. The results are shown in FIG. 16. The binding of the $^{125}$I-labeled TARC was competitively inhibited by unlabeled TARC, IL-8, RANTES, and MCP-1, but hardly by MIP-1α. The Scatchard analysis of the results are shown in FIG. 17. A single kind of specific binding sites for the $^{125}$I-labeled TARC was found on erythrocyte, and the binding constant was calculated to be 17 nM. TARC shares a similar binding constant and the competitive inhibition pattern with other chemokines. For example, the binding constant and the competitive inhibition pattern is similar to those observed when IL-8 binds to DARC. Accordingly, TARC proved to bind DARC on erythrocytes.

EXAMPLE 9

Immunological Assay for TARC

I. Preparation of Immobilized Anti-TARC Antibody (1) Preparation of a Fused Protein Between Glutathione-S-transferase and TARC A fused protein of glutathione-S-transferase (GST) and TARC was prepared using an expression vector pGEX-TARC.

A 0.2 kb DNA fragment which having BamHI and NotI sites at the termini, and containing the mature TARC sequence from the initiation codon to the translational termination codon was obtained by PCR using as a template clone D3A described in Example 1. The two oligonucleotide primers used in the PCR are shown as SEQ ID NOS: 19 and 20. The PCR was conducted on a DNA Thermal Cycler (Perkin-Elmer) using AmpliTaq Kit purchased from Takara Shuzo. The reaction was performed in a reaction buffer (10 mM Tris-HCl, pH 8.3, 50 mM KCl, 1.5 mM MgCl$_2$, 0.1% gelatin, 200 μM dNTPs (dATP, dGTP, dCTP, dTTP), 400 μM primers, and 100 U/ml AmpliTaq DNA polymerase I) using the DNA of clone D3A as a template. The reaction was carried out as follows: a pretreatment for 3 minutes at 94° C.; 15 cycles of 45 seconds at 94° C., 45 seconds at 57° C., and one minute at 72° C.; and a final treatment for 3 minutes at 72° C. The reaction product was then simultaneously digested with BamHI and NotI, and inserted between the BamHI site and the NotI site in pGEX 4T-3 (Pharmacia) to obtain the expression vector pGEX-TARC.

*E. coli* strain JM109 was transformed with the expression vector pGEX-TARC so as to obtain a fused protein in which GST is linked to the amino terminus of TARC of mature secreted form. *E. coli* strain JM109 was cultured for 4 hours at 37° C. in a 2×YT medium containing 0.2% glucose and 0.1 mM IPTG, suspended in a STE buffer (10 mM Tris-HCl, pH 8.0, 1 mM EDTA, 100 mM NaCl, 1 mM PMSF, 100 µg/ml lysozyme), and left for 15 minutes on ice. To the suspension were added DTT and sarkosyl at final concentrations of 5 mM and 1.4%, respectively. The mixture was treated for 300 seconds using a TOMY sonicator UD-201 (TOMY Seiko) at the maximum output while cooling on ice. The mixture was then centrifuged for 5 minutes at 10,000 rpm, 4° C. To the supernatant was added Triton X-100 at a final concentration of 2.5%, and glutathione Sepharose 4B resin, and the binding reaction was allowed to proceed overnight at 4° C. The resin to which the GST-TARC fused protein has been bound was washed five times with PBS, mixed with an equal volume of PBS containing 1% SDS, and treated for 5 minutes at 100° C. to release the GST-TARC fused protein. To the solution of GST-TARC fused protein so obtained was added 9 volumes of PBS, and the resultant solution was used as an antigen.

(2) Preparation of an Anti-TARC Antibody

A mixture of equal volume of 100 µg of GST-TARC fusion protein and Freund's complete adjuvant was administered hypodermally to a guinea pig to prepare anti-TARC antibody. Boosters were hypodermically administrated every two weeks using 100 µg of GST-TARC fused protein mixed with an equal volume of Freund's incomplete adjuvant. After three times of immunization in total, the serum was harvested.

(3) Purification and Labeling of an Anti-TARC Antibody

Preparation of a biotinylated anti-TARC antibody was carried out as follows. Affi-Gel 15 resin (BioRad) was mixed with 3 volumes of a solution of purified GST-TARC fused protein or GST protein and allowed to stand overnight at 4° C. The protein solution was removed, and blocking solution (10 mM ethanolamine, pH 8.0) was added to the resin. The resin was allowed to stand for one hour at 4° C., washed with 20 volumes of PBS, and combined with a binding buffer (20 mM TRis-HCl, pH 7.2, 0.5 M NaCl). To the resultant serum was added an equal volume of saturated ammonium sulfate. The serum was allowed to stand overnight at 4° C., and centrifuged for 20 minutes at 12,000 rpm, 4° C. The resultant precipitates were dissolved in PBS, and an equal volume of saturated ammonium sulfate was added again. After leaving for 2 hours at 4° C., the mixture was centrifuged for 20 minutes at 12,000 rpm, 4° C. The resultant precipitates were dissolved in PBS, dialyzed against the binding buffer, and applied to the GST protein-bound resin and left for 2 hours at room temperature to remove antibodies against GST. The flow-through fraction so obtained was applied to the GST-TARC fused protein-bound resin, and left overnight at 4° C. After washing the resin with 20 volumes of the binding buffer, the antibodies against TARC were eluted with 0.1 M glycine. To the antibody solution was added 1 M Tris-HCl, pH 9.5, and the mixture was dialyzed against 0.1 M NaHCO$_3$. The dialyzed material was mixed with NHS-LC-Biotin (Pierce) and left for 2.5 hours at 4° C. The biotinylated antibody was dialyzed against 50 mM Tris-HCl, pH 7.5, and then against PBS.

The anti-TARC antibody to be immobilized was purified as follows. To the anti-sera was added Tris-HCl, pH 8.0 to 100 mM, and applied to a Hitrap-protein A column. The column was washed with 10 column volumes of 100 mM Tris-HCl, pH 8.0, and then with 10 column volumes of 10 mM Tris-HC, pH 8.0. The bound antibody was eluted with 0.1 M glycine, and after adding 1 M Tris-HCl, pH 9.5, dialyzed against PBS.

II. Immunological Assay for TARC Protein

TARC protein was assayed in the following manner using a so-called sandwich method in which the amount of the TARC bound to an immobilized antibody is quantified with a biotinylated antibody. The antibody to be immobilized was first dissolved in a 50 mM Tris-HCl pH 8.0 buffer to 10 µg/ml and placed in wells on a 96-well plate (Maxisorb, Nunc) in an amount of 50 µl per well, and left overnight at 4° C. After removing the antibody solution, 100 µl PBS containing 1 mg/ml BSA was added. The plate was left for 1 hour at room temperature and washed once with PBS containing 0.02% Tween-20. Triton X-100 was added to 0.5% to a sample containing a recombinant TARC of known concentration, which was expressed and purified from insect cells, or a sample containing an unknown amount of the antigen. The mixture was then added in an amount of 50 µl per well, and left for 1 hour at room temperature. After washing three times with a Tx-PBS solution (0.5% Triton X-100), the biotinylated anti-TARC antibody diluted 1000 times with the Tx-PBS solution was added in an amount of 50 µl per well, and left for 30 minutes at room temperature. After washing three times with the Tx-PBS solution, a peroxidase-labeled streptavidin (Vector) diluted 4000 times with the Tx-PBS solution was added in an amount of 50 µl per well, and left for 30 minutes at room temperature. After washing three times with the Tx-PBS solution, and once with PBS, 100 µl of a substrate solution (100 mM NaOAc, pH 5.5, 1 mM EDTA, 6.72 mg/ml TMBZ, 0.03% H$_2$O$_2$) was added for the color developing reaction. The reaction was stopped by adding 50 µl of 1N H$_2$SO$_4$, and the absorbance at 450 nm was measured. A standard curve was then prepared using the recombinant human TARC of known concentration. The amount of the TARC-protein in a sample can be determined using the standard curve. The detection sensitivity was 50 pg/ml.

EXAMPLE 10

Figure 21:
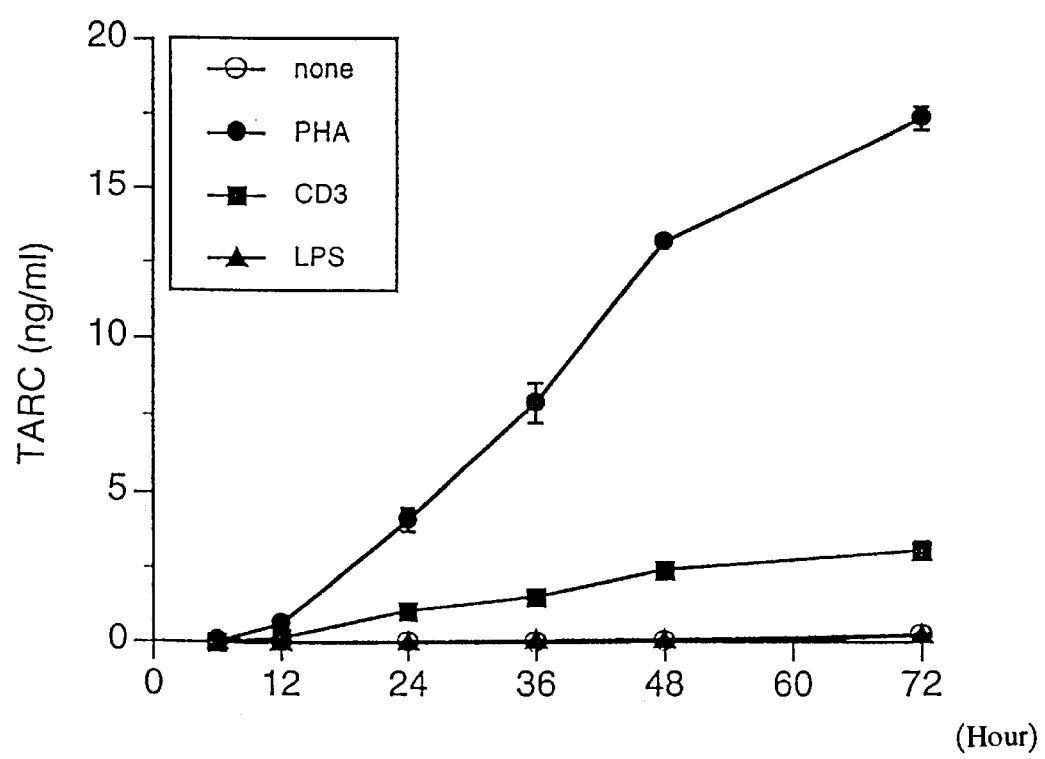
FIG. 21 is a graph showing a time course of the TARC expression from normal human peripheral blood mononuclear cell under the stimulation with PHA, an anti-CD3 antibody, or LPS.

Substances Having TARC-inducing Activity (1) Identification of Stimuli Inducing TARC Protein Normal human peripheral blood mononuclear cells (2.5× 10$^5$ cells per well) were placed in a 96-well plate (Coaster) and incubated in 250 µl of RPMI-1640/10% FCS in the absence of a stimulus, or in the presence of a stimulus, i.e., 100-fold diluted (final) PHA (GIBCO-BRL), 10 µg/ml (final) of an anti-CD3 antibody (OKT3), or 100 ng/ml (final) LPS (L4391, Sigma). After 6, 12, 24, 36, 48, and 72 hours, the cultured medium was harvested, filtrated through a 0.45 µm filter, and the resultant filtrate was used to assay the TARC protein. The results are shown in FIG. 21. As shown in FIG. 21, the TARC protein was expressed under the simulation of PHA, and anti-CD3 antibody in time-dependent manner, and the amount increased linearly until 72 hours. The expression became detectable from 12 hours after the stimulation with PHA, and 24 hours after the stimulation with anti-CD3 antibody. The expression at 72 hours from the stimulation was 16 ng/ml and 2.5 ng/ml when stimulated by PHA and anti-CD3 antibody, respectively. In the case of LPS or no stimuli, the expression was hardly detectable.

(2) Identification of Cytokines Capable of Inducing the TARC Protein

The fact that PHA induces TARC expression more strongly than anti-CD3 antibody suggests that some cytokine may be involved in this induction.

Figure 22:
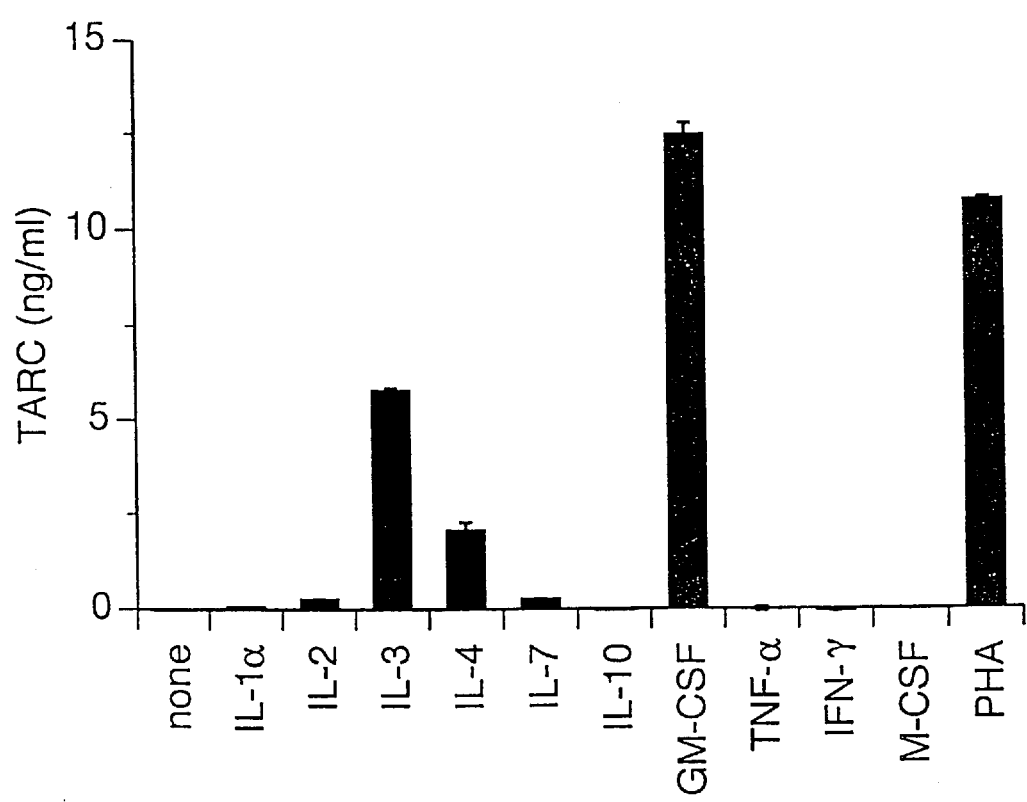
FIG. 22 is a graph showing the levels of the TARC expression from normal human peripheral blood mononuclear cells under the stimulation with various cytokines [IL-1α (R & D), IL-2 (Sionogi Pharmaceutical Co.), IL-3 (Genzyme), IL-4 (PeproTech, Inc.), IL-7 (PeproTech, Inc.), IL-10 (Genzyme), GM-CSF (Genzyme), TNF-α (PeproTech, Inc.), IFN-γ (Sionogi Pharmaceutical Co.), M-CSF and PHA (R & D)].

Normal human peripheral blood mononuclear cells (2.5× 10$^5$cells per well) were placed in a 96-well plate (Coaster) and incubated in 250 µl of RPMI-1640/10% FCS without cytokines or in the presence of a cytokine selected from 10 ng/ml IL-1α (R & D), 100 U/ml IL-2 (Sionogi Pharmaceutical Co.), 50 ng/ml IL-3 (Genzyme), 50 ng/ml IL-4 (PeproTech), 50 ng/ml IL-7 (PeproTech), 50 ng/ml IL-10 (Genzyme), 10 ng/ml GM-CSF (Genzyme), 50 ng/ml TNFα (PeproTech), 1000 U/ml IFN-γ (Sionogi Pharmaceutical Co.), or 10 ng/ml M-CSF (R & D). After 48 hours, the cultured medium was harvested, and filtered through a 0.45 μm filter. The resulting filtrate was then used to assay the TARC protein. The results are shown in FIG. 22. As shown in FIG. 22, the TARC protein was induced by GM-CSF, IL-3 and IL-4, giving the expression amount of about 12, 6 and 2 ng/ml, respectively.

Similarly, the concentration dependency was studied for GM-CSF, IL-3, and IL-4. The results are shown in FIG. 23. As shown in FIG. 23, $ED_{50}$ for GM-CSF was 0.7 ng/ml, and the expression reached to the maximum at 3.3 ng/ml, and decreased at a higher concentration. IL-3 and IL-4 gave saturation curves, and their $ED_{50}$ were 0.5 and 0.8 ng/ml, respectively.

The above results indicate that the expression of TARC is highly distinctive in contrast with those of many chemokines induced by TNFα or IFN-γ.

EXAMPLE 11

Figure 24:
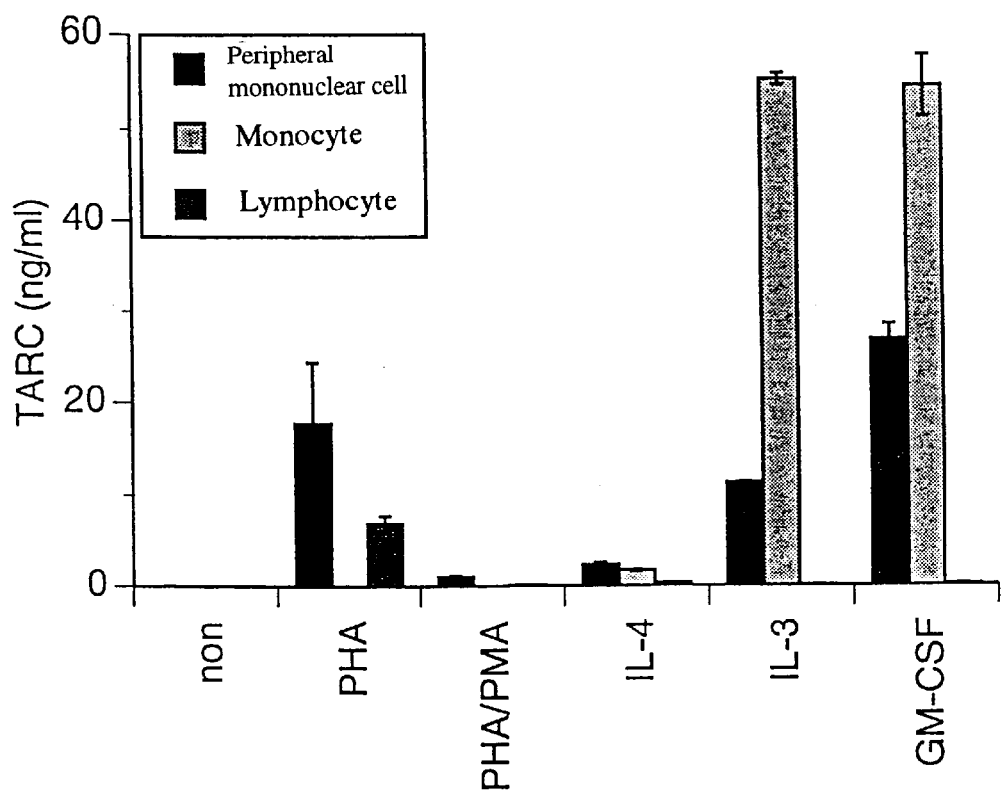
FIG. 24 is a graph showing the inductive effects of PHA, PHA/PMA, GM-CSF, IL-3, or IL-4 on the TARC expression in CD14-positive monocytes and CD14-negative lymphocytes separated from normal human peripheral blood mononuclear cells.

Identification of Cells Expressing the TARC Protein (1) To identify cells expressing TARC, normal human peripheral blood mononuclear cells were separated into CD14-positive monocytes and CD14-negative lymphocytes, and stimulated with PHA, PHA/PMA, GM-CSF, IL-3, or IL-4. Normal human peripheral blood mononuclear cells were suspended in an ice-cooled separation buffer (5 mM EDTA, 1% FCS, PBS) at $2\times10^7$ cells/ml. To the suspension was added 1/50 volume of a FITC-labeled anti-CD14 antibody (Becton-Dickinson). The cells were allowed to stand for 30 minutes on ice, washed with the separation buffer, and suspended in the separation buffer at $10^7$ cells/80 μl. To the cells were added magnetic beads-labeled anti-mouse IgG antibody (Miltenyi-Biotec) in an amount of 20 μl per $10^7$ cell, and left for 15 minutes at 4° C. The cells were washed with the separation buffer, suspended in 500 μl of the separation buffer, and separated into CD14-positive monocytes and CD14-negative lymphocytes using MACS (Miltenyi-Biotec). Normal human peripheral blood mononuclear cells ($2.5\times10^5$ cells per well), CD14-negative lymphocytes ($2.5\times10^5$ cells per well), or CD14-positive monocytes ($1.8\times10^5$ cells per well) were placed in 96-well plate (Coaster) and incubated in 250 μl RPMI-1640/10% FCS, in the absence or presence of a stimulus selected from 100-fold diluted PHA (GIBCO-BRL), 100-fold diluted PHA (GIBCO-BRL) with 50 ng/ml PMA, 50 ng/ml IL-4 (PeproTech), 50 ng/ml IL-3 (Genzyme) or 10 ng/ml GM-CSF (Genzyme). After 48 hours, the cultured medium was harvested, filtered though a 0.45 μm filter, and the resulting filtrate was used to assay the TARC protein. The results are shown in FIG. 24. As shown in the graph of FIG. 24, TARC was secreted only from the monocytes when stimulated with GM-CSF, IL-3, or IL-4. On the contrary, TARC was secreted only from the lymphocytes when stimulated with PHA, or PHA/PMA and the expression under the PHA-stimulation was remarkably inhibited by PMA.

(2) Analysis of Expression of TARC mRNA by Northern Blotting

Figure 25:
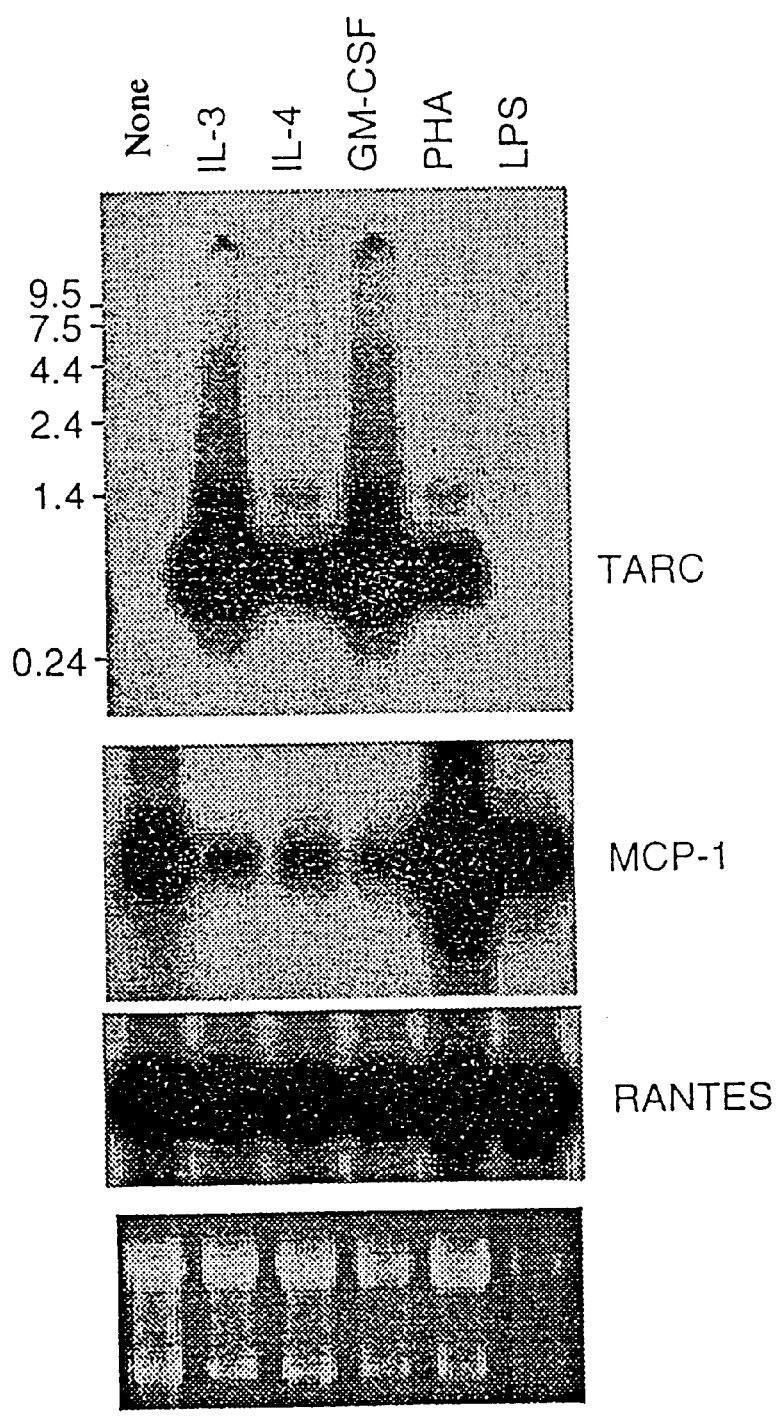
FIG. 25 is a result of Northern blotting showing the expression of TARC mRNA expression in human peripheral blood mononuclear cells stimulated by PHA (GIBCO-BRL), LPS (L4391, Sigma Chemical Co.), IL-4 (PeproTech, Inc.), IL-3 (Genzyme) or GM-CSF (Genzyme).

Human peripheral blood mononuclear cells were unstimulated, or stimulated with 100-fold diluted PHA (GIBCO-BRL), 100 ng/ml LPS (LA391, Sigma), 10 ng/ml IL-4 (PeproTech), 10 ng/ml IL-3 (Genzyme), or 4 ng/ml GM-CSF (Genzyme). After 24 hours, RNAs were extracted from the mononuclear cells using TRIZOL RNA Purification Reagent (GIBCO-BRL). Five μg each of the isolated RNAs was electrophoresed on a 1.2% agarose gel containing 0.66 M formaldehyde, and transferred onto a nylon membrane (Hybond-N+, Amersham Japan). These membranes were subjected to a hybridization procedure using as a probe the SmaI-PstI fragment of the cDNA clone D3A labeled with $^{32}P$ by means of Multiprime DNA Labeling System (Amersham Japan). The hybridization was conducted for 1.5 hours at 68° C. in a QuickHyb solution (Stratagene) containing 100 μg/ml salmon sperm DNA. After washing the membranes with a buffer consisting of 2×SSC and 0.1% SDS for 10 minutes at room temperature and twice with a buffer consisting of 0.2×SSC and 0.1% SDS for 30 minutes at 55° C., X-ray films (Kodak) were exposed thereto, and developed for analysis. It was revealed from the results shown in FIG. 25 that mRNA for TARC was hardly expressed in the unstimulated or LPS-stimulated human peripheral blood mononuclear cells, whereas expression of the mRNA was induced by the GM-CSF or IL-3 stimulation by a factor of about 400, and by the IL-4 stimulation by a factor of about 40.

The above results indicate that the expression of TARC from peripheral blood mononuclear cells stimulated with GM-CSF, IL-3, or IL-4 is not due to the release of proteins accumulated in secretory granules or the like, but is mainly due to the increase in the amount of mRNA.

EXAMPLE 12

Migration Activity of Human PBMC-derived TARC on a T-cell Line

Migration activity of the TARC secreted from normal human peripheral blood monocytes stimulated by cytokine was studied on a T-cell line in the following manner.

The cell migration activity was measured using a 48-well chemotaxis chamber (Neuro Probe). Human peripheral blood monocytes were unstimulated or stimulated with 50 ng/ml IL-4 (PeproTech), 50 ng/ml IL-3 (Genzyme), or 10 ng/ml GM-CSF (Genzyme). After 36 hours, the cultured medium was harvested, filtered through a 0.45 μm filter, and the filtrate was used for measurement of its cell migration activity. The culture filtrate was put into the lower well, while a T-cell line HUT78 ($4\times10^5$ cells) suspended in a buffer [RPMI-1640, 20 mM HEPES (pH 7.4), 1% BSA] were added in the upper well.

The upper and lower wells were separated using a polyvinylpyrrolidone-free polycarbonate membrane (5 μm pore size, Neuro Probe) coated with a Type IV collagen solution (5 μg/ml aqueous solution) for 1 hour at room temperature. After incubation for 2 hours at 37° C., the membrane was removed and the upper side was washed with PBS, fixed, and stained.

The number of migrated cells were microscopically counted in 5 fields (HPF) selected at random per well at a magnifying power of 800. The results are shown in FIG. 26. As shown in the graphs in FIG. 26, the cultured medium stimulated by IL-3 or GM-CSF induced strong migration of HUT78 cells, while cultured medium unstimulated or stimulated with IL-4 did not.

In addition, the migration activity of GM-CSF-treated cultured supernatant on Hut78 cells almost disappeared when treated with 10 μg/ml of guinea pig anti-TARC antibody (TARC Ab).

These results indicate that TARC having a migration activity is secreted from monocytes by stimulation with cytokines.

EXAMPLE 13

Inhibition of Expression of TARC by Cytokines

Figure 27:
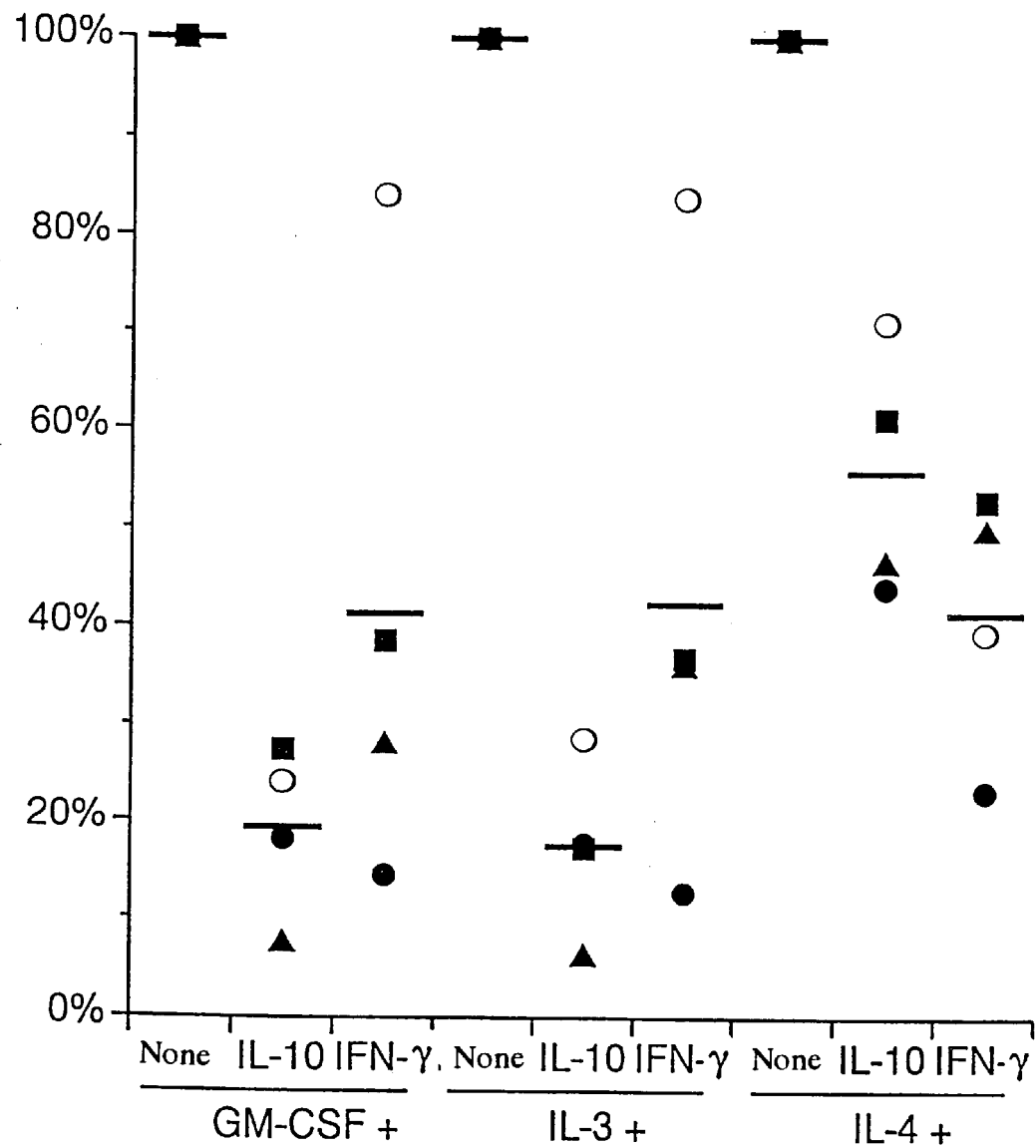
FIG. 27 is a graph showing the suppressive effects of cytokines IFN-γ and IL-10 on the TARC expression from normal human peripheral blood mononuclear cells under the stimulation with cytokines.

In the light of the fact that TARC is induced by IL-4, a type Th2 cytokine involved in the induction of humoral immunity, the effects of IFN-γ (a type Th1 cytokine which suppresses the induction of Th2) and IL-10 (a cytokine which suppresses the immune response generally) on the induction of TARC expression were studied. Normal human peripheral blood mononuclear cells ($2.5 \times 10^5$ cells/well) were placed in a 96-well plate (Coaster). To the well was added a cytokine (10 ng/ml IL-4 (PeproTech), 10 ng/ml IL-3 (Genzyme) or 5 ng/ml GM-CSF (Genzyme)), and the mixture incubated in 250 μl RPMI-1640/10% FCS in the presence of 50 ng/ml IL-10 (Genzyme) or 1000 U/ml IFN-γ (Sionogi Pharmaceutical Co.) for 48 hours. The cultured medium was then recovered, filtered through a 0.45 μm filter, and the resulting filtrate was used to assay the TARC protein. The results are shown in FIG. 27. As shown in the graph in FIG. 27, the induction of the TARC expression under the stimulation with GM-CSF, IL-3 or IL-4 was suppressed by IFN-γ and IL-10. It is thus believed that the secretion of TARC is induced by stimulating the induction of humoral immunity, and suppressed under the condition in which the cellular immunity is induced.

EXAMPLE 14

Binding Activity of TARC to 293/FB1NA-1 Cell Expressing CCR4

The binding activity of TARC to CCR4 receptor expressed on the 293/EBNA-1 cell surface was evaluated using a fused protein of TARC and secreted alkaline phosphatase (SEAP)-(Histidine)$_6$.

(1) Preparation of the Fused Protein (TARC-SEAP)

Figure 28:
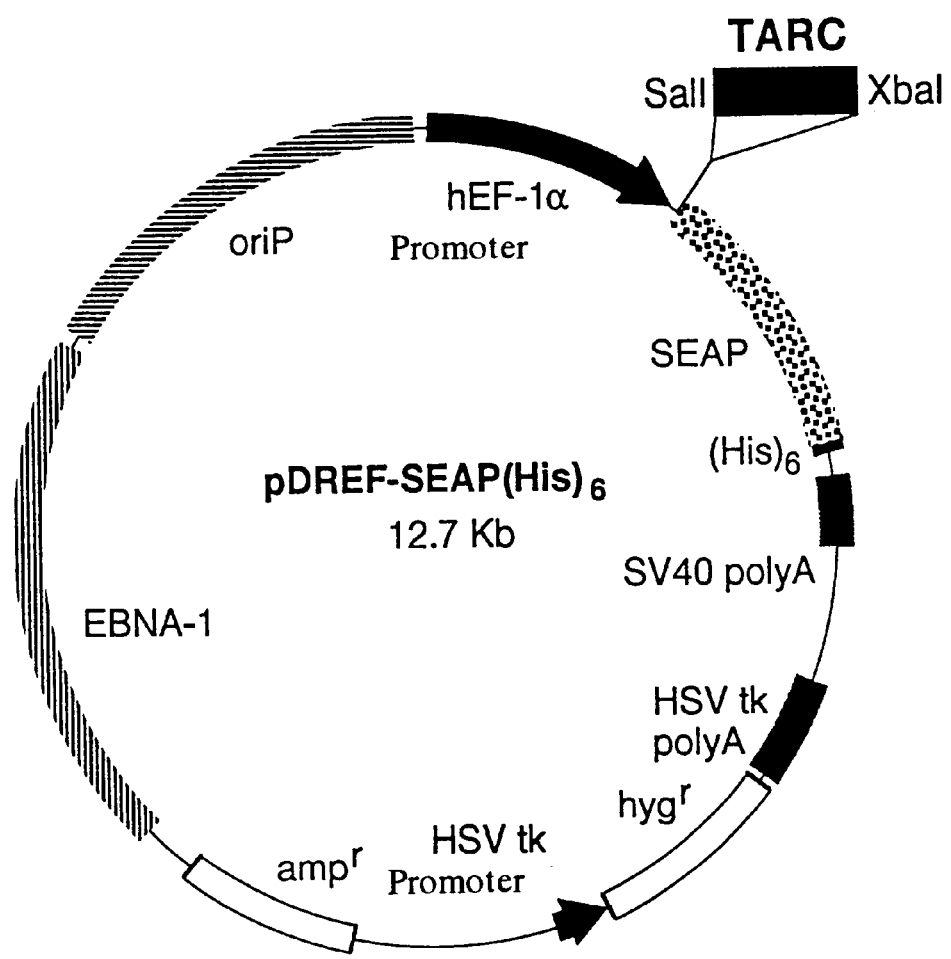
FIG. 28 is a gene map of a recombinant vector pDREF-TARC-SEAP(His)$_6$ used for the expression of a fused protein of TARC and SEAP.

A vector pDREF-SEAP(His)$_6$ for expressing TARC as a fused protein with SEAP is shown in FIG. 28. The said vector was constructed as follows. A region encoding a sequence wherein six histidine residues are linked, i.e., (His)$_6$ region SEQ ID NO: 36, was amplified by PCR using plasmid pSEAP-Enhancer manufactured by Clontech as a template, and 5'-XbaI-AP primer (SEQ ID NO: 21) and 3'-AP(HIS)$_6$-NotI primer (SEQ ID NO: 22). The resultant PCR product was digested with restriction enzymes XbaI and NotI, and inserted between the XbaI and NotI sites in pDREF-Hyg (Yoshida et al, FEBS Letters 360: 155–159, 1995) to obtain pDREF-SEAP(HIS)$_6$.

The ORF of the TARC cDNA was then inserted between the SalI and XbaI sites in the pDREF-SEAP(His)$_6$ to obtain a vector pDREF-TARC-SEAP(HIS)$_6$ which encodes a protein in which TARC is fused to SEAP-(HIS)$_6$ via a linker consisting of 5 amino acids (Ser-Arg-Ser-Ser-Gly) as shown in FIG. 28. Preparation of this vector is described below.

The base sequence encoding TARC was amplified by PCR using the TARC cDNA as a template, and TY98F primer (SEQ ID NO: 21) and TY98R primer (SEQ ID NO: 22). The resultant PCR product was digested with restriction enzymes SalI and XbaI, and then inserted between the SalI and XbaI sites in pDREF-SEAP(HIS)$_6$ to obtain pDREF-TARC-SEAP(HIS)$_6$. 293/EBNA-1 cells (Invitrogen) were transformed with the vector using lipofectamin (Gibco-BRL), and incubated for 3–4 days. The cultured supernatant was recovered, filtered through a filter having 0.45 μm pore size. 20 mM HEPES (pH 7.4) and 0.02% sodium azide were then added to the filtrate, and stored at 4° C.

(2) Assay for the Fused Protein (TARC-SEAP)

Analysis of the produced fused protein (TARC-SEAP) was performed by a sandwich type enzyme-linked immunosorbent assay (ELISA).

Thus, a 96-well micro test plate (Maxsorb, Nunc) was coated with a monoclonal anti-placental alkaline phosphatase (anti-PLAP, Medix Biotech) (2 μg/ml, 50 mM Tris-HCl, pH 9.5), and blocked with bovine serum albumin (BSA, 1 mg/ml in phosphate buffered saline). Samples diluted with a dilution buffer (PBS containing 0.02% Tween-20) were added to the microplate, and reacted for 1 hour at room temperature. After washing with the dilution buffer, a 500-fold diluted biotinylated rabbit anti-PLAP antibody was added, and reacted for 1 hours. After washing, a peroxidase-conjugated streptavidin (Vector) was added, and reacted for 30 minutes. After washing, the activity of the bound peroxidase was detected with 3,3'-5,5'-tetramethylbenzidine. The reaction was stopped with 1N $H_2SO_4$, and the absorbance at 450 nm was measured.

The activity of alkaline phosphatase (AP) was measured by a chemiluminescence method using Great EscApe Detection Kit (Clontech), and expressed in relative light unit (RLU)/s. Preparation of the AP standard curve was achieved using a purified PLAP (Cosmo Bio). The SEAP and TARC-SEAP used provided $8.7 \times 10^7$ RLU/s and $1.2 \times 10^8$ RLU/s, respectively, per pmol.

(3) Preparation of 293/EBNA-1 Cells Expressing CCR4

A region encoding CCR4 was amplified by PCR using a human placental genomic DNA (Clontech) as a template, and CKR4-XbaF primer (SEQ ID NO: 25) and CKR4-XbaR primer (SEQ ID NO:26). The resultant PCR product was digested with a restriction enzyme XbaI, and introduced into the XbaI site of pBluescript SK$^+$ (Stratagene). The CCR4-encoding region was recovered from the resultant plasmid through the digestion with SalI and NotI, and inserted between the SalI and NotI sites in pDREF-Hyg (Yoshida et al., FEBS Letters 360: 155–159, 1995) to obtain pDREF-CCR4. 293/EBNA-1 cells (Invitrogen) were transformed with the vector using lipofectamin (Gibco-BRL), and incubated for one week in the presence of hygromycin (200 μg/ml). 293/EBNA-1 cells exhibiting the drug-resistance were selected to obtain cells to which CCR4 has been introduced.

(4) Specific Binding of the TARC-SEAP Fused Protein to 293/EBNA-1 Cells Expressing CCR4

Figure 29:
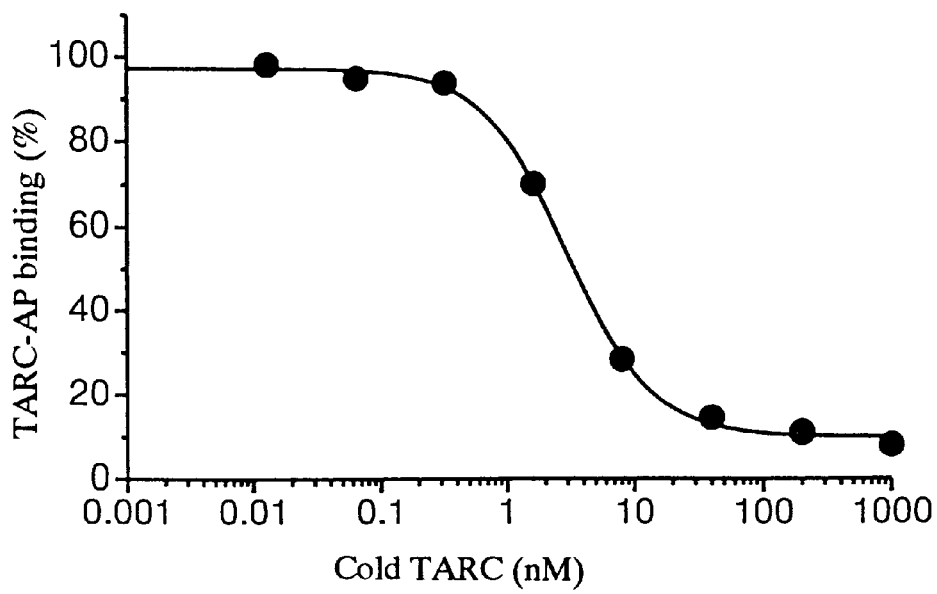
FIG. 29 is a graph showing the change in the specific binding of TARC-SEAP to 293/EBNA-1 cells expressing CCR4, which was measured at a fixed concentration of TARC-SEAP at 1 nM while increasing the concentration of unlabeled TARC.

The change in the specific binding of TARC-SEAP to 293/EBNA-1 cells expressing CCR4 was studied at a fixed concentration of TARC-SEAP (1 nM) while changing the concentration of unlabeled TARC. The binding experiment was conducted in 200 μl RPMI-1640 containing 20 mM HEPES (pH 7.4), 1% BSA, and 0.02% sodium azide. For the competitive binding experiment, 1 nM TARC-SEAP and various concentrations of unlabeled TARC were added to $4 \times 10^5$ cells and allowed to react for 1 hour at room temperature. Cells were washed and dissolved in 50 μl 10 mM Tris-HCl (pH 8.0) containing 1% Triton X-100, and treated at 65° C. for 10 minutes to inactivate the phosphatase originated from the cells. After centrifugation, the AP activity in 25 μl of the supernatant was measured. The nonspecific binding was measured using 1 nM SEAP. The amount of the specific binding was calculated by subtracting the value for the SEAP nonspecifically bound from the value for the TARC-SEAP bound in the presence of various concentrations of unlabeled TARC, and expressed in percentage considering the amount of the specific binding in the absence of unlabeled TARC as 100%. The results are shown in FIG. 29. The 50% inhibitory concentration, which represents the binding strength, of TARC proved to be about 3 nM, showing that TARC binds to CCR4 strongly.

(5) The Effects of Other Chemokines on the Specific Binding of the TARC-SEAP Fused Protein to 293/EBNA-1 Cells Expressing CCR4

The competitive effect of other chemokines on the binding of TARC to 293/EBNA-1 cells expressing CCR4 was evaluated as follows.

Figure 30:
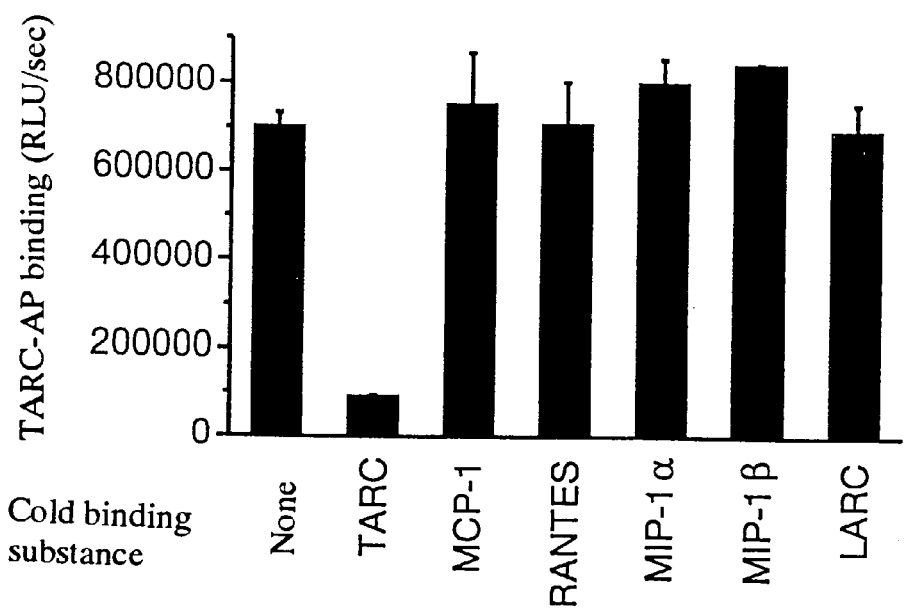
FIG. 30 is a graph showing the inhibitory effects of 200 nM of unlabeled human chemokine of various kinds including TARC on the TARC-SEAP binding to 293/EBNA-1 cells expressing CCR4, which was measured at a fixed concentration of TARC-SEAP at 1 nM.

Binding reaction between 1 nM TARC-SEAP and 4×10⁵ 293/EBNA-1 cells expressing CCR4 was conducted for 1 hour at room temperature, in the absence of unlabeled chemokines or in the presence of 200 nM MCP-1, RANTES, MIP-1α, MIP-1β (all manufactured by PeproTech), LARC, or TARC. The results are shown in FIG. 30. The binding of TARC-SEAP was competitively inhibited only by unlabeled TARC, and not by any other chemokines. These results indicate that CCR4 is a receptor which does not strongly bind the chemokines other than TARC.

EXAMPLE 15

Migration Activity of hTARC on 293/EBNA-1 Cells Expressing CCR4

The cell migration activity of human TARC on 293/EBNA-1 cells expressing CCR4 was measured using a 48-well chemotaxis chamber (Neuro Probe). Human TARC which was expressed in and purified from insect cells according to the procedures described in Example 2 was diluted with a buffer [RPMI-1640, 20 mM Hepes (pH 7.4), 1% BSA], and put into the lower well. 1×10⁵ 293/EBNA-1 cells expressing CCR4 were put into the upper well. The upper and lower wells were separated with a polyvinylpyrrolidone-free polycarbonate membrane (8 μm pore size, Neuro Probe) which was coated with Type IV collagen solution (20 μg/ml aqueous solution) for 4 hours at 37° C. After incubating for 4 hours at 37° C., the membrane was removed, the upper side was washed with PBS, fixed, and stained.

Figure 31:
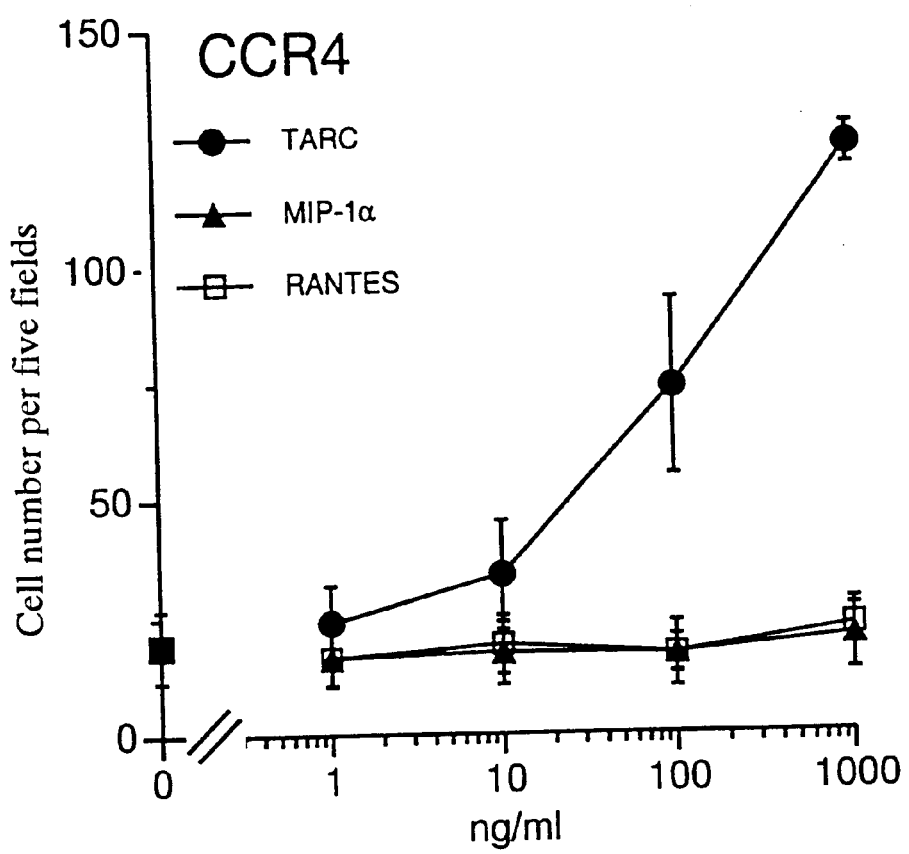
FIG. 31 is a graph showing the effects of concentration of TARC, RANTES, and MIP-1α on the migration activity of 293/EBNA-1 cells expressing CCR4.

The number of migrated cells were microscopically counted in 5 fields (HPF) selected at random per well at a magnifying power of 400. The results are shown in FIG. 31. As shown in the graph in FIG. 31, the 293/EBNA-1 cells expressing CCR4 migrated towards TARC in concentration-dependent manner. In the Figure, the filled box on the axis of ordinates indicates the result for a control which does not contain TARC. RANTES and MIP-1α, which are chemokines of different type from TARC, did not exhibit any significant migration activity on 293/EBNA-1 cells expressing CCR4.

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 582 base pairs
      (B) TYPE: nucleic acid
      (C) STRANDEDNESS: double
      (D) TOPOLOGY: linear (ii) MOLECULE TYPE: cDNA to mRNA (ix) FEATURE:
      (A) NAME/KEY: CDS
      (B) LOCATION: 53..334

(xi) SEQUENCE DESCRIPTION: SEQ ID NO:1:

```
CCCTGAGCAG AGGGACCTGC ACACAGAGAC TCCCTCCTGG GCTCCTGGCA CC ATG          55
                                                         Met
                                                         1

GCC CCA CTG AAG ATG CTG GCC CTG GTC ACC CTC CTC CTG GGG GCT TCT      103
Ala Pro Leu Lys Met Leu Ala Leu Val Thr Leu Leu Leu Gly Ala Ser
              5                  10                  15

CTG CAG CAC ATC CAC GCA GCT CGA GGG ACC AAT GTG GGC CGG GAG TGC      151
Leu Gln His Ile His Ala Ala Arg Gly Thr Asn Val Gly Arg Glu Cys
         20                  25                  30

TGC CTG GAG TAC TTC AAG GGA GCC ATT CCC CTT AGA AAG CTG AAG ACG      199
Cys Leu Glu Tyr Phe Lys Gly Ala Ile Pro Leu Arg Lys Leu Lys Thr
     35                  40                  45

TGG TAC CAG ACA TCT GAG GAC TGC TCC AGG GAT GCC ATC GTT TTT GTA      247
Trp Tyr Gln Thr Ser Glu Asp Cys Ser Arg Asp Ala Ile Val Phe Val
 50                  55                  60                  65
```

```
ACT GTG CAG GGC AGG GCC ATC TGT TCG GAC CCC AAC AAC AAG AGA GTG    295
Thr Val Gln Gly Arg Ala Ile Cys Ser Asp Pro Asn Asn Lys Arg Val
             70                  75                  80

AAG AAT GCA GTT AAA TAC CTG CAA AGC CTT GAG AGG TCT TGAAGCCTCC     344
Lys Asn Ala Val Lys Tyr Leu Gln Ser Leu Glu Arg Ser
             85                  90

TCACCCCAGA CTCCTGACTG TCTCCCGGGA CTACCTGGGA CCTCCACCGT TGGTGTTCAC  404

CGCCCCCACC CTGAGCGCCT GGGTCCAGGG GAGGCCTTCC AGGGACGAAG AAGAGCCACA  464

GTGAGGGAGA TCCCATCCCC TTGTCTGAAC TGGAGCCATG GGCACAAAGG GCCCAGATTA  524

AAGTCTTTAT CCTCAAAAAA AAAAAAAAAA AAAAAAAAAA AAAAAAAAAA AAAAAAA    582

(2) INFORMATION FOR SEQ ID NO:2:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Pro Leu Lys Met Leu Ala Leu Val Thr Leu Leu Leu Gly Ala
 1               5                  10                  15

Ser Leu Gln His Ile His Ala Ala Arg Gly Thr Asn Val Gly Arg Glu
             20                  25                  30

Cys Cys Leu Glu Tyr Phe Lys Gly Ala Ile Pro Leu Arg Lys Leu Lys
         35                  40                  45

Thr Trp Tyr Gln Thr Ser Glu Asp Cys Ser Arg Asp Ala Ile Val Phe
     50                  55                  60

Val Thr Val Gln Gly Arg Ala Ile Cys Ser Asp Pro Asn Asn Lys Arg
 65                  70                  75                  80

Val Lys Asn Ala Val Lys Tyr Leu Gln Ser Leu Glu Arg Ser
             85                  90

(2) INFORMATION FOR SEQ ID NO:3:

(i) SEQUENCE CHARACTERISTICS:
        (A) LENGTH: 558 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 2..280

(xi) SEQUENCE DESCRIPTION: SEQ ID NO:3:

C ATG AGG TCA CTT CAG ATG CTG CTC CTG GCT GCT CTG CTT CTG GGG     46
  Met Arg Ser Leu Gln Met Leu Leu Leu Ala Ala Leu Leu Leu Gly
   1               5                  10                  15

ACT TTT CTG CAG CAT GCC AGA GCT GCT CGA GCC ACC AAT GTA GGC CGA   94
Thr Phe Leu Gln His Ala Arg Ala Ala Arg Ala Thr Asn Val Gly Arg
             20                  25                  30

GAG TGC TGC CTG GAT TAC TTC AAA GGG GCC ATT CCT ATC AGG AAG TTG   142
Glu Cys Cys Leu Asp Tyr Phe Lys Gly Ala Ile Pro Ile Arg Lys Leu
         35                  40                  45

GTG AGC TGG TAT AAG ACC TCA GTG GAG TGT TCC AGG GAT GCC ATC GTG   190
Val Ser Trp Tyr Lys Thr Ser Val Glu Cys Ser Arg Asp Ala Ile Val
     50                  55                  60
```

-continued

```
TTT CTG ACT GTC CAG GGC AAG CTC ATC TGT GCA GAC CCC AAA GAC AAA      238
Phe Leu Thr Val Gln Gly Lys Leu Ile Cys Ala Asp Pro Lys Asp Lys
         65                  70                  75

CAT GTG AAG AAG GCC ATC AGA TTG GTG AAA AAC CCA AGG CCG              280
His Val Lys Lys Ala Ile Arg Leu Val Lys Asn Pro Arg Pro
 80              85                  90

TGACCTTCCC GCTGAGGCAT TGGAGACGC CAGGGCTGCT GTCCATGGTT TCAACATAAA     340

GCGGCCTGTG ACCAGCAGAG CCCAAGAGCA GCCACAGAGC AGAAGTCCCT GTTCCCTTTT    400

TTATGGACTC TTATGCACTA CAGGCGAACA CAAAAAAAAG CAACGGAATA AAGCCTTCCT    460

CCCTCAAAAA AAAAAAAAAA AAAAAAAAAA AAAAAAAAAA AAAAAAAAAA AAAAAAAAAA    520

AAAAAAAAAA AAAAAAAAAA AAAAAAAAAA AAAAAAA                             558
```

(2) INFORMATION FOR SEQ ID NO:4:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO:4:

```
Met Arg Ser Leu Gln Met Leu Leu Ala Ala Leu Leu Gly Thr
 1               5                  10                  15

Phe Leu Gln His Ala Arg Ala Ala Arg Ala Thr Asn Val Gly Arg Glu
             20                  25                  30

Cys Cys Leu Asp Tyr Phe Lys Gly Ala Ile Pro Ile Arg Lys Leu Val
         35                  40                  45

Ser Trp Tyr Lys Thr Ser Val Glu Cys Ser Arg Asp Ala Ile Val Phe
     50                  55                  60

Leu Thr Val Gln Gly Lys Leu Ile Cys Ala Asp Pro Lys Asp Lys His
 65                  70                  75                  80

Val Lys Lys Ala Ile Arg Leu Val Lys Asn Pro Arg Pro
             85                  90
```

(2) INFORMATION FOR SEQ ID NO:5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:5:

```
GATTAGTTCT AGATCGCGAC GCGGCCGCCC TTTTTTTTTT TTTTT              45
```

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:6:

```
TCGACCCACG CGTCCG                                              16
```

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:7:

CGGACGCGTG GG                                          12

(2) INFORMATION FOR SEQ ID NO:8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:8:

CTACTACTAC TAGGCCACGC GTCGACTAGT ACGGGGGGGG GGGGGGGG      48

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:9:

CCTCTGAAGG TTCCAGAATC GATAGTCTAG A                       31

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:10:

CTCTAGACTA TCGATTCTGG AACCTTCAGA GGTTT                  35

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:11:

-continued

CTACTACTAC TAGGCCACGC GTCGACTAGT AC                          32

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:12:

CCTCTGAAGG TTCCAGAATC GATAG                                  25

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:13:

CGCCATATGG CTCGAGGGAC CAATGTG                                27

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:14:

CGCGCGGCCG CTCAAGACCT CTCAAGGCT                              29

(2) INFORMATION FOR SEQ ID NO:15:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:15:

AATTCGGCAC GAGG                                              14

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:16:

```
GGAGCACGGC                                                              10

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:17:

CTCTGCTTCT GGGGACTTTT CTGC                                              24

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:18:

GGTCACAGGC CGCTTTATGT TGAA                                              24

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:19:

CGCGGATCCG CTCGAGGGAC CAATGTG                                           27

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:20:

CGCGCGGCCG CTCAAGACCT CTCAAGGCT                                         29

(2) INFORMATION FOR SEQ ID NO:21:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"
```

(xi) SEQUENCE DESCRIPTION: SEQ ID NO:21:

CGCTCTAGAA GCTCCGGAAT CATCCCAGTT GAGGAGGAGA AC					42

(2) INFORMATION FOR SEQ ID NO:22:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:22:

CGCGCGGCCG CTCAGTGATG GTGATGGTGA TGACCCGGGT GCGCGGCGTC GGT					53

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:23:

CGCGTCGACG GCACCATGGC CCCACTG					27

(2) INFORMATION FOR SEQ ID NO:24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:24:

CGCTCTAGAA GACCTCTCAA GGCTTTG					27

(2) INFORMATION FOR SEQ ID NO:25:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:25:

GCTCTAGAGC CACCATGAAC CCCACGGATA TAGCAGAT					38

(2) INFORMATION FOR SEQ ID NO:26:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

```
           (xi) SEQUENCE DESCRIPTION: SEQ ID NO:26:

CGTCTAGACT ACAGAGCATC ATGGAGATCA TG                                      32

(2) INFORMATION FOR SEQ ID NO:27:

(i) SEQUENCE CHARACTERISTICS:
              (A) LENGTH: 68 amino acids
              (B) TYPE: amino acid
              (C) STRANDEDNESS:
              (D) TOPOLOGY: linear (ii) MOLECULE TYPE: protein (xi) SEQUENCE DESCRIPTION: SEQ ID NO:27:

Ser Pro Tyr Ser Ser Asp Thr Thr Pro Cys Cys Phe Ala Tyr Ile Ala
1               5                  10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65

(2) INFORMATION FOR SEQ ID NO:28:

(i) SEQUENCE CHARACTERISTICS:
              (A) LENGTH: 70 amino acids
              (B) TYPE: amino acid
              (C) STRANDEDNESS:
              (D) TOPOLOGY: linear (ii) MOLECULE TYPE: protein (xi) SEQUENCE DESCRIPTION: SEQ ID NO:28:

Ala Ser Leu Ala Ala Asp Thr Pro Thr Ala Cys Cys Phe Ser Tyr Thr
1               5                  10                  15

Ser Arg Gln Ile Pro Gln Asn Phe Ile Ala Asp Tyr Phe Glu Thr Ser
            20                  25                  30

Ser Gln Cys Ser Lys Pro Gly Val Ile Phe Leu Thr Lys Arg Ser Arg
        35                  40                  45

Gln Val Cys Ala Asp Pro Ser Glu Glu Trp Val Gln Lys Tyr Val Ser
    50                  55                  60

Asp Leu Glu Leu Ser Ala
65                  70

(2) INFORMATION FOR SEQ ID NO:29:

(i) SEQUENCE CHARACTERISTICS:
              (A) LENGTH: 69 amino acids
              (B) TYPE: amino acid
              (C) STRANDEDNESS:
              (D) TOPOLOGY: linear (ii) MOLECULE TYPE: protein (xi) SEQUENCE DESCRIPTION: SEQ ID NO:29:

Ala Pro Met Gly Ser Asp Pro Pro Thr Ala Cys Cys Phe Ser Tyr Thr
1               5                  10                  15

Ala Arg Lys Leu Pro Arg Asn Phe Val Val Asp Tyr Tyr Glu Thr Ser
            20                  25                  30
```

```
Ser Leu Cys Ser Gln Pro Ala Val Val Phe Gln Thr Lys Arg Ser Lys
        35                  40                  45

Gln Val Cys Ala Asp Pro Ser Glu Ser Trp Val Gln Glu Tyr Val Tyr
 50                  55                  60

Asp Leu Glu Leu Asn
 65
```

(2) INFORMATION FOR SEQ ID NO:30:

(i) SEQUENCE CHARACTERISTICS:
        (A) LENGTH: 73 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:30:

```
Lys Ser Met Gln Val Pro Phe Ser Arg Cys Cys Phe Ser Phe Ala Glu
 1               5                  10                  15

Gln Glu Ile Pro Leu Arg Ala Ile Leu Cys Tyr Arg Asn Thr Ser Ser
            20                  25                  30

Ile Cys Ser Asn Glu Gly Leu Ile Phe Lys Leu Lys Arg Gly Lys Glu
        35                  40                  45

Ala Cys Ala Leu Asp Thr Val Gly Trp Val Gln Arg His Arg Lys Met
 50                  55                  60

Leu Arg His Cys Pro Ser Lys Arg Lys
 65                  70
```

(2) INFORMATION FOR SEQ ID NO:31:

(i) SEQUENCE CHARACTERISTICS:
        (A) LENGTH: 76 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:31:

```
Gln Pro Asp Ala Ile Asn Ala Pro Val Thr Cys Cys Tyr Asn Phe Thr
 1               5                  10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
 50                  55                  60

Asp His Leu Asp Lys Gln Thr Gln Thr Pro Lys Thr
 65                  70                  75
```

(2) INFORMATION FOR SEQ ID NO:32:

(i) SEQUENCE CHARACTERISTICS:
        (A) LENGTH: 76 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:32:

```
Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75
```

(2) INFORMATION FOR SEQ ID NO:33:

(i) SEQUENCE CHARACTERISTICS:
        (A) LENGTH: 76 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:33:

```
Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
                20                  25                  30

Ser Ser His Cys Pro Arg Glu Ala Val Ile Phe Lys Thr Lys Leu Asp
            35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75
```

(2) INFORMATION FOR SEQ ID NO:34:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:34:

```
Ser Arg Ser Ser Gly
1               5
```

(2) INFORMATION FOR SEQ ID NO:35:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Modified-site
        (B) LOCATION: 10..11
        (D) OTHER INFORMATION: /note= "Xaa is undetermined"

(xi) SEQUENCE DESCRIPTION: SEQ ID NO:35:

```
Ala Arg Ala Thr Asn Val Gly Arg Glu Xaa Xaa Leu Asp Tyr Phe
1               5                   10                  15
```

(2) INFORMATION FOR SEQ ID NO:36:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:36:

```
His His His His His His
1               5
```

(2) INFORMATION FOR SEQ ID NO:37:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:37:

```
CAYCAYCAYC AYCAYCAYCG CGCGGCCGCT CAGTGATGGT GATGGTGATG ACCCGGGTGC      60
GCGGCGTCGG T                                                          71
```

What is claimed is:

1. An isolated or purified protein having migration activity on cells expressing CCR4 receptor and comprising an amino acid sequence selected from the group consisting of:

i) residue 24 to 94 of SEQ ID NO:2;

ii) residue 1 to 94 of SEQ ID NO:2;

iii) residue 24 to 93 of SEQ ID NO:4; and iv) residue 1 to 93 of SEQ ID NO:4.

2. A pharmaceutical composition comprising the protein as claimed in claim 1 in association with a carrier therefor.

3. An isolated or purified DNA encoding a protein having migration activity on cells expressing CCR4 receptor and comprising an amino acid sequence selected from the group consisting of:

i) residue 24 to 94 of SEQ ID NO:2;

ii) residue 1 to 94 of SEQ ID NO:2;

iii) residue 24 to 93 of SEQ ID NO:4; and iv) residue 1 to 93 of SEQ ID NO:4.

4. An expression vector comprising the DNA of claim 3.

5. A host cell transformed with the expression vector of claim 4.

6. The cell of claim 5, which is a silkworm cell.

7. A process for producing a protein capable of inducing a migration of cells expressing CCR4 receptor, comprising cultivating the transformant of claim 5, and recovering the protein with said activity from the cultured medium.

8. A recombinant protein produced according to the method of claim 7.

9. An isolated or purified DNA encoding a protein having migration activity on cells expressing CCR4 receptor, wherein the DNA has a sequence selected from the group consisting of:

i) residue 53 to 334 of SEQ ID NO:1;

ii) residue 122 to 334 of SEQ ID NO:1;

iii) residue 71 to 280 of SEQ ID NO:3; and iv) residue 2 to 280 of SEQ ID NO:3.

\* \* \* \* \*

UNITED STATES PATENT AND TRADEMARK OFFICE
CERTIFICATE OF CORRECTION

PATENT NO. : 6,793,917 B1
DATED : September 21, 2004
INVENTOR(S) : Toshio Imai, Tetsuya Yoshida and Osamu Yoshie It is certified that error appears in the above-identified patent and that said Letters Patent is hereby corrected as shown below:

Title page,
Item [*] Notice, should be -- 61 days --, not "1826" days.

Signed and Sealed this

Twenty-eighth Day of June, 2005

JON W. DUDAS
*Director of the United States Patent and Trademark Office*